United States Patent
Cabiri et al.

(10) Patent No.: US 11,197,789 B2
(45) Date of Patent: Dec. 14, 2021

(54) REGULATOR DEVICE FOR DRUG PATCH

(71) Applicant: ALMA THERAPEUTICS LTD., Petach-Tikva (IL)

(72) Inventors: Oz Cabiri, Hod-HaSharon (IL); Yossi Gross, Moshav Mazor (IL); Ran Hezkiahu, Herzlia (IL)

(73) Assignee: Alma Therapeutics Ltd., Petach Tikva (IL)

( * ) Notice: Subject to any disclaimer, the term of this patent is extended or adjusted under 35 U.S.C. 154(b) by 510 days.

(21) Appl. No.: 16/104,526

(22) Filed: Aug. 17, 2018

(65) Prior Publication Data
US 2018/0353740 A1    Dec. 13, 2018

Related U.S. Application Data

(63) Continuation of application No. PCT/IL2017/050211, filed on Feb. 19, 2017.
(Continued)

(51) Int. Cl.
*A61M 35/00* (2006.01)
*A61F 17/00* (2006.01)
(Continued)

(52) U.S. Cl.
CPC .......... *A61F 17/00* (2013.01); *A61F 13/0283* (2013.01); *A61M 35/10* (2019.05);
(Continued)

(58) Field of Classification Search
CPC ................. A61F 13/0283; A61F 17/00; A61F 2013/0296; A61M 2037/0023;
(Continued)

(56) References Cited

U.S. PATENT DOCUMENTS 5,190,558 A    3/1993 Ito
5,498,235 A    3/1996 Flower
(Continued)

FOREIGN PATENT DOCUMENTS

EP    0848937 A2    6/1998
GB    2448493 A    10/2008
(Continued)

OTHER PUBLICATIONS

Harapanhalli "Scientific and Regulatory Challenges of Transdermal Drug Delivery Systems (TDDS) and Relevance of Quality-by-Design (QbD) Approach to Their Development", Presented to the Advisory Committee for Pharmaceutical Science and Clinical Pharmacology, FDA, U.S, Food and Drug Administration, Silver Spring, MD, USA, Aug. 5, 2009, p. 1-38, Aug. 2009.
(Continued)

*Primary Examiner* — Kai H Weng
(74) *Attorney, Agent, or Firm* — Dekel Patent Ltd.; David Klein

(57) ABSTRACT

Embodiments are disclosed of a method of controlling timing and/or dosage of a transdermal drug patch. For example, a control device operative to move the patch to one or more of a plurality of operational relationships with a skin of a patient, including being fully engaged with the skin, partially engaged with the skin, and disengaged with the skin. The device may include a roller that peels a patch on and off the skin. Optionally a convention patch is used. In some embodiments a patch and/or an adaptor has a mobile zone and an immobile zone. In some embodiments, an active surface of the patch fully contacts the skin in an engaged state. For example the patch may be attached to the device on a passive portion thereof.

1 Claim, 32 Drawing Sheets

Related U.S. Application Data

(60) Provisional application No. 62/376,023, filed on Aug. 17, 2016.

(51) Int. Cl.
 *A61F 13/02* (2006.01)
 *A61M 37/00* (2006.01)

(52) U.S. Cl.
 CPC .. *A61F 2013/0296* (2013.01); *A61M 37/0015* (2013.01); *A61M 2037/0023* (2013.01); *A61M 2205/3303* (2013.01); *A61M 2205/3592* (2013.01); *A61M 2205/50* (2013.01); *A61M 2205/8206* (2013.01); *A61M 2207/00* (2013.01); *A61M 2207/10* (2013.01); *A61M 2209/06* (2013.01)

(58) Field of Classification Search
 CPC .. A61M 2205/3303; A61M 2205/3592; A61M 2205/50; A61M 2205/8206; A61M 2207/00; A61M 2207/10; A61M 2209/06; A61M 35/003; A61M 35/10; A61M 37/0015; A61M 39/28
 See application file for complete search history.

(56) References Cited

U.S. PATENT DOCUMENTS

| | | |
|---|---|---|
| 6,589,202 B1 | 7/2003 | Powell |
| 2003/0065294 A1 | 4/2003 | Pickup et al. |
| 2004/0087992 A1 | 5/2004 | Gartstein et al. |
| 2007/0088264 A1* | 4/2007 | Liebl ................. A61M 37/00 604/117 |
| 2007/0161964 A1 | 7/2007 | Yuzhakov |
| 2008/0208146 A1 | 8/2008 | Brandwein et al. |
| 2008/0220092 A1 | 9/2008 | Dipierro |
| 2010/0042050 A1 | 2/2010 | Chowdhury |
| 2010/0256568 A1 | 10/2010 | Frederickson et al. |
| 2012/0302942 A1 | 11/2012 | Dipierro |
| 2013/0144261 A1 | 6/2013 | Chowdhury |
| 2014/0200525 A1 | 7/2014 | Dipierro |
| 2014/0207047 A1 | 7/2014 | Dipierro et al. |
| 2014/0207048 A1 | 7/2014 | Dipierro et al. |
| 2014/0323423 A1 | 10/2014 | Dipierro et al. |
| 2015/0190628 A1* | 7/2015 | Kim ................. A61M 39/286 604/250 |
| 2016/0038434 A1 | 2/2016 | Schaller et al. |

FOREIGN PATENT DOCUMENTS

| | | |
|---|---|---|
| WO | 2014203910 A1 | 12/2014 |
| WO | 2016132368 A1 | 8/2016 |

OTHER PUBLICATIONS

Sadrien "Challenges in the Development of Transdermal Drug Delivery Systems", Presented to the Advisory Committee for Pharmaceutical Scinece and Clinical Pharmacology, FDA, U.S. Food and Drug Administration, Silver Spring, MD, USA, Aug. 5, 2009, p. 1-17, Aug. 2009.

International Search Report PCT/IL2017/050211 Completed Jun. 6, 2017; dated Jun. 7, 2017 3 pages.

Written Opinion of the International Searching Authority PCT/IL2017/050211 dated Jun. 7, 2017 8 pages.

* cited by examiner

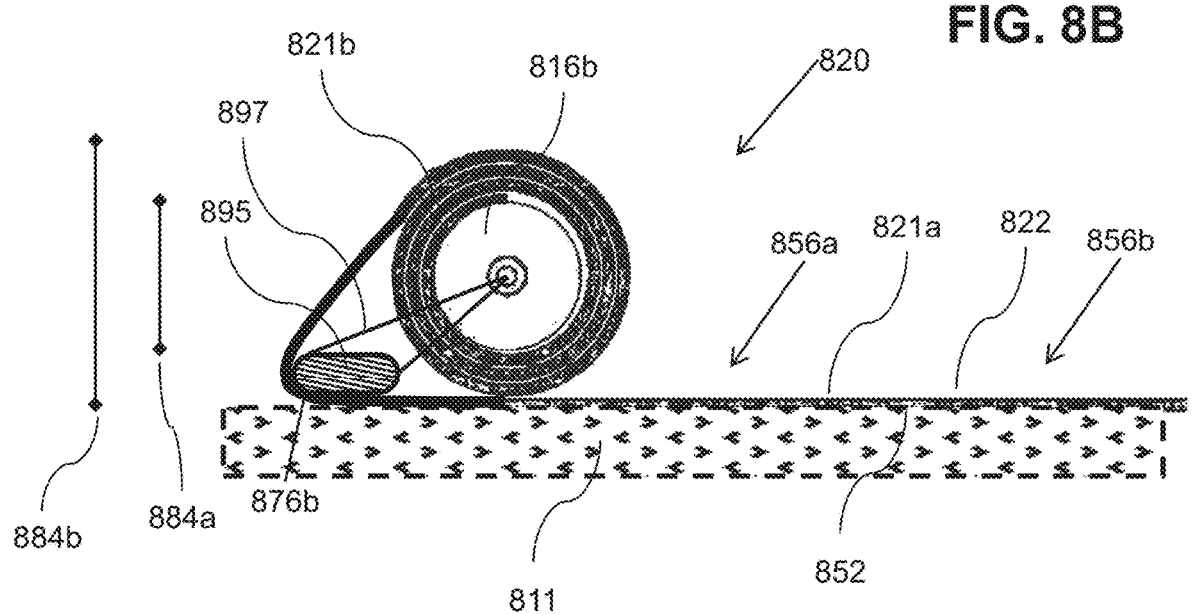
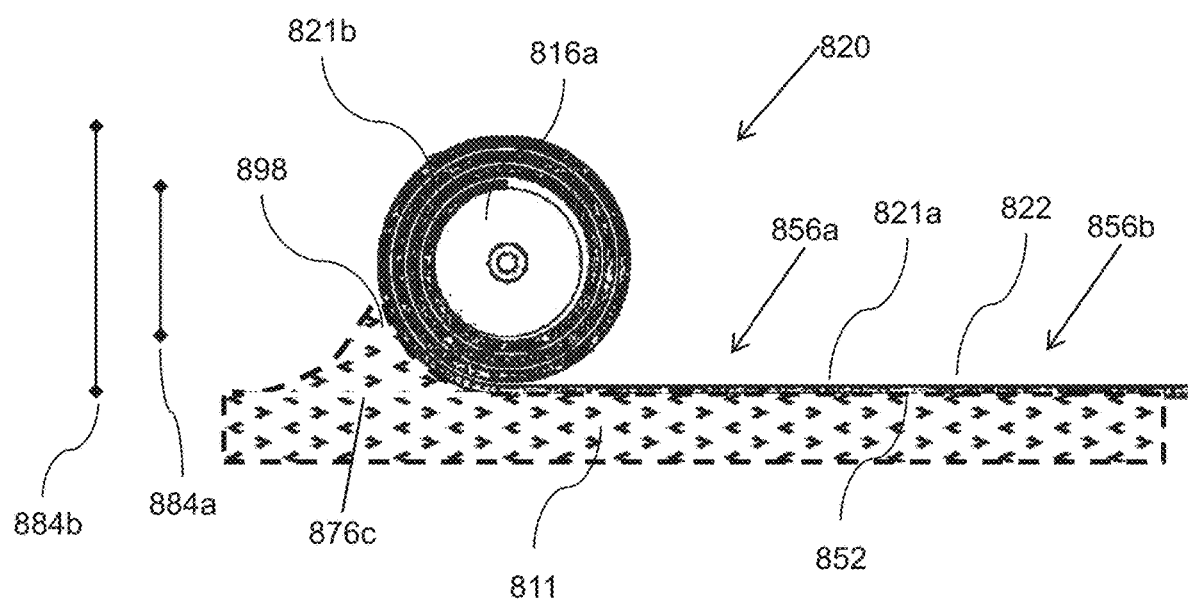

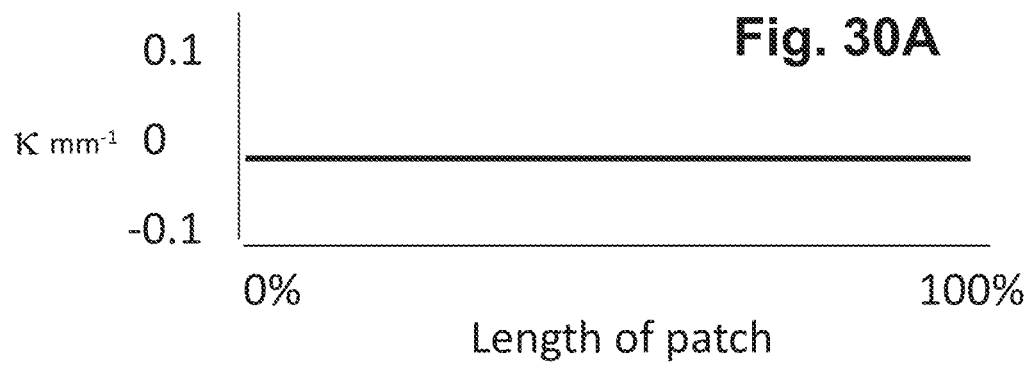
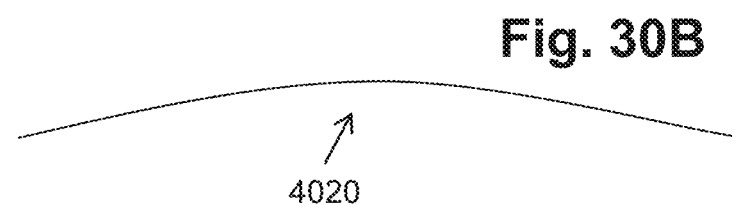
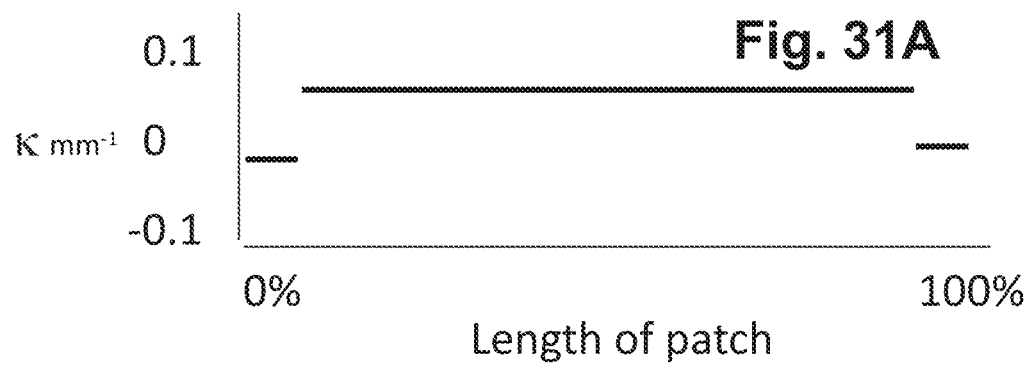
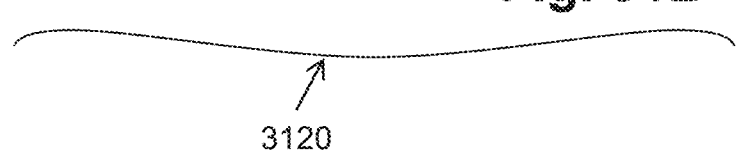

REGULATOR DEVICE FOR DRUG PATCH

RELATED APPLICATION/S

This application is a Continuation of PCT Patent Application No. PCT/IL2017/050211 having International filing date of Feb. 19, 2017, which claims the benefit of priority of U.S. Provisional Patent Application No. 62/376,023 filed Aug. 17, 2016, and PCT International Patent Application No. PCT/IL2016/050196 filed Feb. 18, 2016. PCT/IL2016/050196 is related to U.S. Utility patent application Ser. No. 14/624,721 filed Feb. 18, 2015. The contents of the above applications are all incorporated by reference as if fully set forth herein in their entirety.

FIELD AND BACKGROUND OF THE INVENTION

The present invention, in some embodiments thereof, relates to a system to control transdermal delivery and, more particularly, but not exclusively, to a system to control timing, rate and/or dosage of transdermal delivery from a conventional drug patch and/or a customized drug patch.

U.S. Patent Publication No. 2014/0323423 discloses "systems and methods for longevity, anti-aging, fatigue management, obesity, weight loss, weight management, delivery of nutraceuticals, and treating hyperglycemia, Alzheimer's disease, sleep disorders, Parkinson's disease, Attention Deficit Disorder and nicotine addiction involve synchronizing and tailoring the administration of nutraceuticals, medications and other substances (for example, stimulants) in accordance with the body's natural circadian rhythms, meal times and other factors. Improved control of blood glucose levels, extended alertness, and weight control, and counteracting of disease symptoms when they are at their worst are possible. An automated, pre-programmable transdermal administration system is used to provide pulsed doses of medications, pharmaceuticals, hormones, neuropeptides, anorexigens, pro-drugs, stimulants, plant extracts, botanicals, nutraceuticals, cosmeceuticals, phytochemicals, phytonutrients, enzymes, antioxidants, essential oils, fatty acids, minerals, vitamins, amino acids, coenzymes, or other physiological active ingredient or precursor. The system can utilize a pump, pressurized reservoir, a system for removing depleted carrier solution, or other modulated dispensing actuator, in conjunction with porous membranes or microfabricated structures."

U.S. Patent Publication No. 2014/0207048 discloses "establishing a bio-synchronous treatment protocol that incorporates individual temporal and innate biological characteristics into a pharmacological treatment plan. The bio-synchronous treatment protocol is thereafter initiated using bioactive agent delivery device. Bio-synchronous drug delivery includes continual collection of patient data such as physical, psychological, temporal and environmental characteristics. This data is analyzed so to not only determine an initial treatment protocol but to also determining whether modification to the ongoing bio-synchronous treatment protocol is required. And, responsive to determining a modification is required the system modifies the bio-synchronous treatment protocol and use of delivery device. These modifications and treatment protocols can include reactive and proactive psychological support supplied to the patient in a variety of formats."

U.S. Patent Publication No. 2014/0207047 discloses "a bioactive agent delivery device having a plurality of reservoirs wherein each reservoir houses a solvent provides a means for separable and segregated delivery of bioactive agent(s) to a patient. The device can include a plurality of absorbent materials wherein each absorbent material is pretreated with a bioactive agent and a delivery mechanism operable to deliver to any of the plurality of absorbent materials a controlled portion of solvent from any of a plurality of reservoirs. A diffusion layer interposed between the absorbent materials and an epidermis transfers the bioactive agent from the absorbent materials to the epidermis for delivery of the bioactive agent."

U.S. Patent Publication No. 2014/0200525 discloses "systems and methods for synchronizing the administration of compounds with the human body's natural circadian rhythms and addiction rhythms to counteract symptoms when they are likely to be at their worst by using an automated and pre programmable transdermal or other drug administration system."

U.S. Patent Publication No. 20130144261 appears to disclose that "A preparation for the transdermal delivery of a biologically active substance into the body of a patient comprises particles of a formulation comprising the active substance. The particles are irregular in size and shape and may be produced by a low cost manufacturing method such as grinding from a thin film. The particles are angular, i.e. they have sharp edges and corners that allow them to penetrate the outer layer of the skin when subjected to pressure from a roller or an array of blunt-tipped microstructures. Sucrose may be used as an excipient with the active substance to form suitably rigid and angular particles."

Additional background art includes U.S. Patent Publication No. 2012/0302942 U.S. Patent Publication No. 2008/0220092.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a kit for loading a dosage control device for transdermal delivery, including: an alignment jig with a patch positioned thereon a protrusion on the alignment jig positioned opposite an attachment portion of the patch; an alignment feature on the jig for fixing a position of the dosage control device with an applicator of the dosage control device contacting the attachment portion of the patch on the protrusion.

According to some embodiments of the invention, the dosage control device includes a frame and an actuator for moving the applicator with respect to the frame and wherein the patch includes a second attachment portion positioned to attach to the frame when the dosage control device is aligned to the jig.

According to some embodiments of the invention, the patch is a transdermal pharmaceutical patch.

According to some embodiments of the invention, the patch includes an adhesive skirt extending beyond an edge of the attachment portion, the adhesive skirt including an adhesive on a side facing away from the attachment surface.

According to some embodiments of the invention, the adhesive is on a ventral side of the patch and the attachment portion is on the dorsal side of the patch.

According to some embodiments of the invention, an active portion of the patch configured for delivering a drug to the skin of a subject is on a ventral side of the patch and the attachment portion is on the dorsal side of the patch.

According to some embodiments of the invention, an active portion of the patch configured for delivering a drug to the skin of a subject is on a ventral side of the patch and the attachment portion is on the dorsal side of the patch.

According to some embodiments of the invention, the dosage control device includes a sensor configured for sensing a connection to the alignment jig.

According to some embodiments of the invention, the sensor includes a switch.

According to some embodiments of the invention, the dosage control device is configured to move the patch to an inactive position when the dosage control device is placed on the jig.

According to some embodiments of the invention, the dosage control device is configured to move the patch to a inactive position when the dosage control device is removed from the jig.

According to some embodiments of the invention, the applicator includes a roller.

According to an aspect of some embodiments of the invention, there is provided a dosage control system for transdermal administration of a drug to a subject including: a housing including a skin attachment surface on a ventral side thereof; an opening in the ventral side of the housing for engaging a transdermal patch there through; a roller passing along the opening; a guide directing the passing of the roller on a path that is not parallel to the skin attachment surface.

According to some embodiments of the invention, the guide is directed at an angle to the skin attachment surface.

According to some embodiments of the invention, an angle of the guide with respect to the skin attachment surface changes along the guide.

According to an aspect of some embodiments of the invention, there is provided a dosage control system for transdermal administration of a drug to a subject including: a housing including a skin attachment surface on a ventral side thereof; an opening in the ventral side of the housing for engaging a transdermal patch therethrough; a roller passing along the opening; a guide directing the passing of the roller and changing a rate of rotation of the roller per linear movement on the guide.

According to some embodiments of the invention, the roller includes a toothed gear rotated by a toothed track of the guide and wherein a distance between teeth of the track varies to vary the rate of rotation.

According to some embodiments of the invention, the distance between teeth of the track varies nonuniformly.

According to an aspect of some embodiments of the invention, there is provided an alignment jig for mounting a patch on a dosage control device including: an alignment feature for fixing an alignment of the patch on a surface of the alignment jig; a cavity for retaining the dosage control device with an attachment surface of the dosage control device facing the surface of the alignment jig; a protrusion on the surface of the alignment jig positioned to protrude toward a recessed portion of the attachment surface of the dosage control device.

According to some embodiments of the invention, the alignment jig includes a housing including a skin attachment surface on a ventral side thereof; an opening in the ventral side of the housing for engaging the patch therethrough; and a roller passing along the opening; and wherein the recessed portion includes a surface of the roller.

According to some embodiments of the invention, when the dosage control device is retained in the cavity the protrusion of the surface of the alignment jig protrudes into the opening.

According to an aspect of some embodiments of the invention, there is provided a method of loading a patch to a dosage control device the patch having an attachment portion including: supplying an alignment jig with the patch placed with the attachment portion located on a protrusion of the alignment jig; and aligning the dosage control device to the alignment jig with an applicator of dosage control device contacting the attachment portion.

According to some embodiments of the invention, the method further includes: moving the applicator of the dosage control device to pull the attachment portion away from the protrusion.

According to some embodiments of the invention, the moving is triggered when the dosage control device is placed on the jig.

According to some embodiments of the invention, the moving is triggered when the dosage control device is removed from the jig.

According to some embodiments of the invention, a protective liner of an active zone of the patch is connected to a retainer on alignment jig and wherein pulling the attachment portion away from the protrusion includes pulling the active zone of the patch away from the retainer and further including: peeling the liner from the active zone of the patch as a result of the pulling the active zone away from the retainer.

According to some embodiments of the invention, the applicator includes a roller and wherein the moving includes rolling the patch onto the roller.

According to an aspect of some embodiments of the invention, there is provided a pharmaceutical delivery cartridge for delivering a drug to a surface of a subject including: a patch rolled into a roll with a ventral surface facing outward, the ventral surface having an adhesive coating; and a elastic biasing layer biasing the patch to extend away from the roll.

According to some embodiments of the invention, the patch further includes a dorsal surface including a layer that is non-reactive on contact with the ventral surface and the adhesive.

According to some embodiments of the invention, the patch is a transdermal drug patch and wherein the ventral surface is configured for delivering the pharmaceutical to a patient.

According to an aspect of some embodiments of the invention, there is provided a dosage control system for transdermal administration of a drug to a subject including: a housing including a skin attachment surface on a ventral side thereof; an opening in the ventral side of the housing; a roller passing along the opening; a patch biased away from the roller.

According to some embodiments of the invention, the biasing pushes the patch outward from the roller with a force of between 0.01 and 0.5 Newton.

According to some embodiments of the invention, the patch is rolled around the roller with a radius of curvature of between 1 to 10 mm and the unstressed radius of curvature of the patch biasing may be greater than 10 mm.

According to some embodiments of the invention, a stiffness biasing of the patch is small enough that bending the patch to a radius of curvature of 10 mm from its unstressed shape requires a force of less than 0.5 Newton.

According to some embodiments of the invention, a rate of release of the patch is adjusted to cause the biasing.

According to some embodiments of the invention, a rate of release of the patch is greater than a rate of deposition on the skin of a subject.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 8A-8C are a perspective side views of engaging and/or disengaging portions of a patch and/or storing disengaged portions of the patch in accordance with some embodiments of the present invention;

FIGS. 29A, 29B, 30A, 30B, 31A and 31B illustrate exemplary optional unstressed curvatures and shapes for a medicine patch in accordance with embodiments of the current invention.

DESCRIPTION OF SPECIFIC EMBODIMENTS OF THE INVENTION

Figure 1:
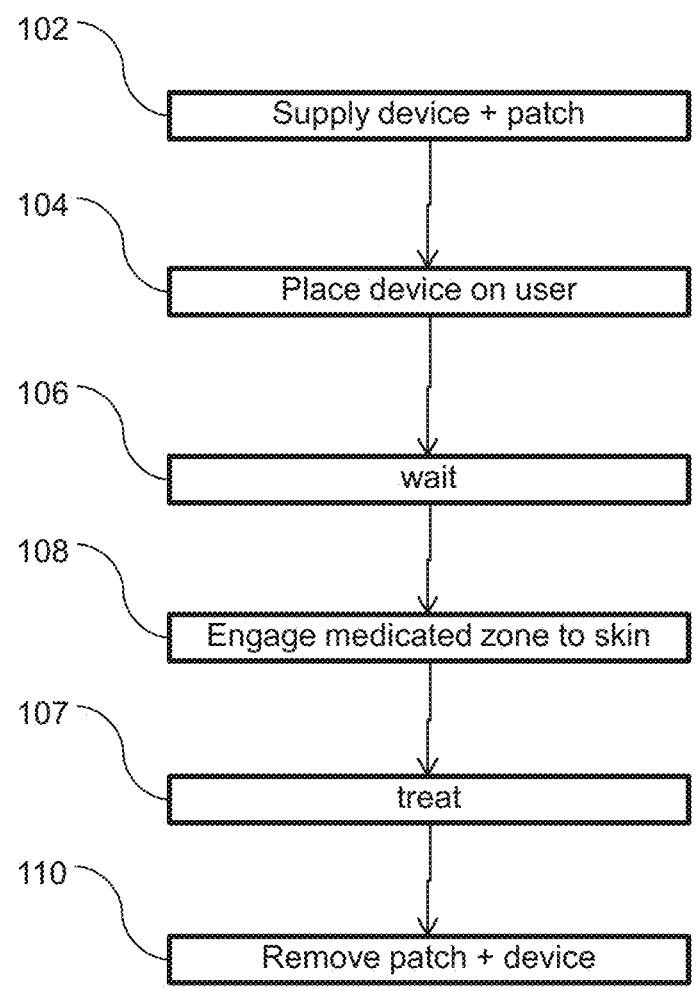
FIG. 1 is a flow chart illustrating a method of delayed engagement of a active surface of a medicine patch in accordance with some embodiments of the present invention.

The present invention, in some embodiments thereof, relates to a system to control transdermal delivery and, more particularly, but not exclusively, to a system to control timing, rate and/or dosage of transdermal delivery from a conventional drug patch and/or a customized drug patch.

Overview

An aspect of some embodiments of the current invention relates to an assembly for controlling timing and/or rate of transdermal delivery that optionally controls drug delivery from a conventional transdermal drug patch. Optionally the system may be used to automatically stop and/or slow delivery of a drug from a transdermal patch.

In some embodiments the device may control delivery from a convention patch approved by a regulatory agency (for example the U.S. Food and Drug Administration FDA and/or the European Commission CE) for a fixed and/or predetermined delivery rate schedule and/or dosage of a drug. For example, in some embodiments, a method and/or apparatus according to the current invention may facilitate use of the patch for delivery of a dose less than the approved dosage and/or at a delivery rate slower than the approved rate.

In some embodiments, delivery may be interrupted before the approved dose has been delivered. Optionally, interrupting delivery may include discontinuing delivery temporarily, discontinuing delivery permanently, and/or reducing a rate of delivery with respect a predetermined and/or fixed rate schedule of a patch. For example, delivery may be automatically interrupted after less than 1% of the approved dose has been administered and/or after delivery of between 1 to 10% and/or between 10 to 30% and/or between 30 to 50% and/or between 50 to 70% and/or between 70 to 90% of the approved dosage. For example, interrupting delivery may include stopping delivery and/or reducing delivery to a rate less than 1% of an approved rate at a given time after application and/or less than 10% and/or between 10 to 30% and/or between 30 to 50% and/or between 50 to 70% and/or between 70 to 90%.

In some embodiments, interruption of delivery is made automatically, for example, without human supervision and/or intercession after applying of the drug patch. Optionally, delivery is made automatically according to preprogramming prior to and/or during use of the device Optionally, a conventional and/or fixed dose and/or regulatory approved patch may be used to administer a drug without any material intervening between the skin and an active surface of the patch and/or without modifying the drug delivery mechanism of the patch. For example, the conventional preset and/or fixed dose and/or regulatory approved patch may be used to administer a drug without requiring any regulatory significant substance intervening between the patch and the skin and/or without compromising the approved drug delivery mechanism of the patch.

In some embodiments a dosage schedule and/or a schedule of patch engagement and/or disengagement, and/or control logic (e.g. in reaction to sensors) may be programmed into a device by a supplier of the device and/or a supplier of the drug, for example before distribution. Alternatively a device may be programmed by a medical professional and/or a personal aid and/or a pharmacist and/or the subject before use. Alternatively a device may be programmed by a medical professional and/or a personal aid and/or a pharmacist and/or the subject dynamically and/or during use.

An aspect of some embodiments of the current invention relates to initiating and/or increasing a rate of administering of a transdermal drug automatically. For example, administration may be initiated more than ½ hour and/or between ½ hour and 2 hours and/or between 2 hours and 8 hours and/or between 8 hours and 24 hours after human intercession or supervision (for example after the system has been placed on a subject). For example, administration may be initiated in response to an event and/or at a fixed time. For example, administration may be initiated while a subject is asleep and/or incapacitated. For example administration may be initiated without supervision and/or without the presence of a helper and/or medical aid.

In some embodiments transdermal drug administration may be automatically initiated from a conventional and/or preset dosage and/or fixed rate schedule patch. For example, after automated initiation of delivery, transdermal delivery may occur from the patch in accordance to convention regulatory conditions. For example, there may be no regulatory significant modification to the drug administering portion of the patch. For example, there may be no regulatory significant intervening substance between the patch and the skin of the subject. Optionally initiation of drug delivery may include switching from no significant delivery to delivery of a significant quantity of the drug. For example, a significant quantity of a drug may include administration at a regulatorily approved rate from a convention drug patch and/or between 50 to 100% of the approved rate and/or between 10 to 50% of the approved rate. In some embodiments initiating delivery may include a significant increase of a rate of delivery. Increasing a rate of delivery may include increasing a rate to between 120% to 150% and/or between 150 to 200% and/or between 200 to 400% more than 400% the rate previous to the increase. For example the rate may be defined as the rate averaged over 1 minute and/or over 5 minutes and/or over ½ hour.

In some embodiments, transdermal drug administration may be initiated and/or increased in rate and/or interrupted and/or reduced in rate in response to an event. For example, a sensor may sense an event and trigger a change in the administration. In some embodiments, the change may take place automatically. For example, the sensor may sense a medical condition, for example a change in cardiac function and/or breathing and/or temperature and/or a reaction to a drug. A patch control device may change the administration in response to output of the sensor. For example, sensor output may be received by a processor that may send a signal to a driver to change the drug administration. For example, a sensor may sense a reaction to a drug and send a signal to a processor which may respond by sending a command to interrupt and/or reduce drug administration. For example, a sensor may sense a medical condition requiring a treatment and send a signal to a processor which may respond by sending a command to initiate and/or increase drug administration. For example, a control device may engage a Nicotine patch to increase the Nicotine level in the blood just before a subject a wakes of. In some embodiments, automatically administering Nicotine before wake up may help reduce morning craving for a cigarette. For example, the wakeup time may be fixed slightly before an alarm time set on an alarm clock (for example a wake up alarm of a smart phone). Alternatively or additionally, wake up may be determined by a sensor sensing body movements and/or vital signs. In some embodiments, applying the patch and/or administering a drug close to the time when it is needed may increase the effect of the drug without increasing the dosage. In some embodiments, administering the drug close to the time of need may facilitate reduction of dosage and/or reduce the habituation effect of high levels of drug administration and/or reduce the risk for over dose.

In some embodiments, a conventional patch may include a passive delivery mechanism. For example, a convention transdermal patch may include a drug-in-adhesive monolithic patch and/or a drug-in-adhesive multilaminate patch and/or a liquid reservoir patch and/or a polymer matrix patch. The patch optionally may be based on a reservoir system and/or a matrix system with and/or without a rate controlling membrane.

An aspect of some embodiments of the current invention relates to automated engaging and/or disengaging of a transdermal drug patch. In some embodiments, an apparatus may automatically engage and/or disengage a drug patch at a fixed time and/or in response to an event. Alternatively or additionally, the apparatus may engage and/or disengage the patch in response to a command.

In some embodiments, the apparatus moves the patch to one or more of a plurality of operational relationships with the skin of the subject (for example a patient). For example, operational relationships may include the patch and/or an active surface of the patch being in full engagement with the skin (i.e., the entire active surface of patch is in contact with the skin), being in partial engagement with the skin (i.e., only a portion of the active surface of patch is in contact with the skin), and being disengaged from the skin (e.g. the active surface of the patch is not in contact with the skin).

In some embodiments, the assembly uses any commercially available transdermal patch impregnated or otherwise provided with a substance. For example, the system can use an existing approved transdermal patch from an approved patch supplier with the previously unknown feature of controlled time of initiation of delivery, breaks in delivery, changes in rate of delivery and/or cessation of delivery.

In some embodiments, the device may disengage a patch by moving an active surface of the patch and/or a portion thereof away from a skin of the subject. For example the active surface may be moved between 0.1 and 1 mm away from the skin and/or between 1 mm and 5 mm and/or between 5 mm and 2 cm and/or more.

In some embodiments, a patch may be peeled from the skin and/or an edge of a patch may be peeled from the skin. As used herein, the term/phrase peel means to remove and/or lift a covering (e.g. a patch and/or a substrate) from a surface (for example skin) along a line and/or curve (the line or curve will be referred to as a separation line) progressively. As used herein, the term/phrase peel an edge means to remove and/or lift a covering from a surface along a separation line progressively and wherein there is a path from the separation line to an edge of the covering along a separated portion of the covering. As used herein, the term/phrase peel from an edge means to remove and/or lift a covering from a surface along a separation line and wherein there is a path from the separation line to an edge of the covering along a separated portion of the covering and the separation line progresses away from the edge. For example the separation line may progress away from a peeled edge.

In some embodiments, the patch may be engaged by placing on the skin progressively. For example a separation line may serve as a connecting line and may progress from a connected edge toward a separated edge. Optionally, a roller may roll across a patch to separate it or join it to the skin. For example, the separate line may be the line of contact where the patch is sandwiched between the roller and the skin.

In some embodiments a patch may be peeled and/or an edge of the patch may be peeled and/or the patch may be peeled from an edge thereof from the skin. For example, an edge of the patch may be connected to a control device and/or an applicator and/or a puller mechanism. Optionally, the active surface of the patch may be lifted progressively off the skin. In some embodiments a patch may be raised off the skin by expanding a variable thickness mesh interceding between the patch and the skin.

In some embodiments a patch may be stored. Optionally the patch may be stored in a disengaged state, for example with an active surface of the patch distanced from the skin of the subject. For example, a patch may be stored rolled onto a roller and/or in a space in a housing and/or covered by a protective liner.

In some embodiments, the system of the invention may engage a patch by applying it to the skin and/or disengage a patch by peeling the patch from the skin. Engaging and/or disengaging may occur at certain times for certain time durations. For example a patch may be engaged and/or disengaged while the user is asleep or incapacitated. In some embodiments, the rate of drug administration may be increased by increasing the active area of the patch in contact with the skin. In some embodiments, the rate of drug administration may be decreased by decreasing the active area of the patch in contact with the skin. The total amount of substance administered is optionally controlled by independently controlling of the time and rate of delivery.

In some embodiments, a patch may have various zones. Disengaging an active surface may include moving the patch such that the active surface is no longer in contact with the skin and/or moving the patch such that a secondary zone contacts the skin. Optionally the secondary zone will contact the same region and/or a different region than the active surface. In some embodiments, an active surface may be partially engaged. For example engaging the active surface and/or increasing the rate of drug delivery may be achieved by increasing the surface area of contact between the active surface and the skin. For example disengaging the active surface and/or decreasing the rate of drug delivery may be achieved by decreasing the surface area of contact between the active surface and the skin.

In some embodiments, a secondary region may be a passive region (e.g. without a drug). Alternatively a secondary region may include a different dosage and/or a different drug and/or different treatment means than the active region. In some embodiments, a patch and/or a substrate may include multiple regions with different drugs and/or treatments. In some embodiments, different zones may contact the skin sequentially and/or in an arbitrary order (for example determined by a command and/or programming of a controller) and/or simultaneously. Optionally a zone may be engaged reversibly and/or moved to an inactive position (for example a storage position) and/or protected during storage and/or reengaged. Optionally reengaging a zone may include reversing a driver and/or a zone may be reengaged by a cyclic system (for example a continuous belt). In some embodiments, a device will progressively engage more active area of a patch, for example to maintain a steady and/or constant dosage. An inactive position is a position where the active zone of the patch is distanced from the subject while the device is placed on the subject, such that the subject does not receive a significant dose of the pharmaceutical. A significant does may be a clinically significant dose over a period of less than 1 day. Alternatively or additionally, a patch may be moved to a non-active position where the subject does not received a clinically significant dose over a period of less than 1 hour and/or 1 day and/or 10 days. For example, in a non-active position the subject may not received a dose of less than $1/10$ and/or $1/100$ and/or $1/1000$ of a prescribed dose over a period of less than 1 hour and/or 1 day and/or 10 days. For example, in a non-active position the rate of dosing of the medicine to a subject may be less than $1/10$ and/or less than $1/100$ and/or less than $1/1000$ less than $1/10000$ the rate of dosage of the pharmaceutical when the active zone is in an engaged position.

In some embodiments a conventional patch may be repeatedly engaged and/or disengaged. For example a patch may be engaged and/or disengaged once and/or between 2 to 3 times and/or between 4 to 6 times and/or more. Alternatively or additionally, a patch may be modified for enhanced reapplication. For example, a patch may use a gel instead of and/or in addition to a conventional adhesive to hold the patch in place. In some embodiments gel may enhance reengaging of the patch. For example, a gel patch may be engaged and/or disengaged between 1 to 3 times and/or between 4 to 6 times and/or between 7 to 10 times or more.

In some embodiments, a control device may exert a force relative to a patch and the skin of the subject. For example, an actuator may be connected to a frame. The actuator optionally moves with respect to the frame. Optionally an actuator includes an applicator and/or a puller. For example, an applicator may push a patch onto the skin of a subject. For example, a puller may pull a patch away from the skin of a subject. Optionally a single component (for example a roller) may be both a puller and an applicator. Optionally the actuator is connected to a mobile portion of the patch. In some embodiments the frame is attached to the skin of the subject. Optionally, an immobile portion of the patch may attach the frame to the skin. A force between the frame and the actuator optionally results in a force and/or movement of the patch with respect to the skin. Optionally, a driver may exert the force between the frame and the actuator.

In some embodiments a patch control device includes a frame and a roller. In some embodiments, one portion of the patch, for example a leading edge of a mobile section thereof, may be attached to a roller. For example, a stationary portion of the patch may be attached to a frame of the device. For example, a trailing edge of the mobile portion of the patch may be connected to the immobile portion of the patch.

In some embodiments a length of a device may range for example between 5 to 25 mm and/or between 25 to 60 mm and/or between 60 to 90 mm and/or between 90 to 120 mm and/or between 120 to 200 mm and/or greater than 200 mm. In some embodiments a width of a device may range for example between 10 to 50% and/or between 50 to 75% and/or between 75 to 125% and/or between 125 to 200% and/or between 200 to 400% and/or between 400 to 1000% its length. For example, the ventral surface area and/or skin attachment surface area of a device may range between 100 to 130% and/or between 130% to 250% and/or between 250% to 500% the area of a ventral surface of a patch to be controlled. For example the device may control a patch of length between 5 to 25 mm and/or between 25 to 60 mm and/or between 60 to 100 mm and/or between 100 to 200 mm. In some embodiments a width of a patch may range for example between 10 to 50% and/or between 50 to 75% and/or between 75 to 125% and/or between 125 to 200% and/or between 200 to 400% and/or between 400 to 1000% its length. For example a patch may include a 70×70 mm or 50×50 mm or 35×35 mm patch. Exemplary patches include Nicotrol of GSK and/or Nicoretee and/or Nicoderm. For example a patch may be rated at a fixed dose of about 5, 10, or 15 or 22 mg/day over 16-24 hrs. In some embodiments, a controller will initiate the drug delivery for example between 5 minutes to an hour and/or between an hour and 2 hours and/or between 2 hours and 4 hours and/or between 4 hours and 8 hours and/or between 8 hours and 16 hours and/or between 16 hours and 24 hours after attaching the system to the subject.

In some embodiments, the device will move a patch from a disengaged state to an engaged state in a time ranging between 1 seconds to 10 seconds and/or between 10 seconds to 30 seconds and/or between 30 seconds and 90 seconds and/or between 90 seconds and 2 minutes and/or between 2 minutes and 1 hour. Alternatively or additionally, a device may slowly engage a patch over a time ranging between an hour to 4 hours and/or 4 hours to 12 hours and/or 12 hours to 24 hours and/or 24 hours to a week. For example slowly engaging a patch may keep a constant rate of delivery over a period. In some embodiments, drug delivery may start immediately up to a full dose. In some embodiments, the device will move a patch from a engaged state to a disengaged state in a time ranging between 1 seconds to 10 seconds and/or between 10 seconds to 30 seconds and/or between 30 seconds and 90 seconds and/or between 90 seconds and 2 minutes and/or between 2 minutes and 1 hour. For example, disengagement may include pulling a patch from the skin. For example, disengagement may take 10 to 60 seconds if using a motor or 1 to 5 seconds using a preloaded spring and/or gas pressure.

In some embodiments, disengaging a patch (for example, pulling a patch from the skin) and/or storing the patch, may happened at any stage during the delivery. In some embodiments the patch may be stored for reuse within an approved time. In some embodiments, the patch may be replaced and/or the device reused. Alternatively or additionally the patch and device may be replace together. For example a patch and/or a device may be replaced after a time ranging between 1 hour to 8 hours and/or 8 hours to 16 hours and/or 16 hours to 1 day and/or 1 day to 2 days and/or 2 days to a week.

In some embodiments, a portion of the patch may be stored in a disengaged state. For example, between 0 to 20% and/or between 20 to 50% and/or between 50 to 80% and/or between 80 to 100% of the patch may be stored. For example, between 0 to 20% and/or between 20 to 50% and/or between 50 to 80% and/or between 80 to 100% of a mobile portion of patch may be stored.

In some embodiment a roller may engage and/or disengage a patch. Optionally the patch may be stored rolled up on the roller in a disengaged state. For example the roller may unroll the patch on to the skin engaging the patch. Optionally, the roller may roll along the patch, pulling up the patch along a separation line, peeling the patch off the skin and/or disengaging the patch and/or rolling up the patch onto the roller. Optionally, the separation is the line of contact where the patch is sandwiched between the roller and the skin. Optionally, a roller may serve one, some, or all of the functions described above. For example, a roller may serve one, some, or all of guiding movement of a separation line between a patch and skin, pulling a patch away from skin and/or a separation line, and/or storing a patch.

In some embodiments a roller may be configured to rotate at a rate that varies according to the diameter of the roll of patch being rolled up or unrolled. For example, the rate of rotation may be controlled to let out and/or take up the patch at the same rate as the linear movement of the roll. For example, for a larger roll the rate of rotation of the roller may be adjusted downward with respect to the linear rate of progress of the roller. For example, the roller without the patch may have a diameter ranging between 2 to 6 mm and/or between 6 to 10 mm and/or between 10 to 15 mm and/or between 15 to 25 mm. Optionally the diameter of the roll (including the roller with the patch rolled around it) may range between 0 to 2 mm and/or between 2 to 4 mm and/or between 4 to 6 mm and/or between 6 to 10 mm or between 10 to 20 mm greater than the diameter of the roller alone. For example, a patch may be rolled around a roller in 1 layer and/or 2 to 4 layers and/or 4 to 10 layers and/or 10 to 20 layers.

In some embodiments, a patch may be mounted on a substrate and/or an adaptor. The substrate is optionally driven by a driver. Optionally, the operation of the driver is controlled by a controller. For example, the controller may control when and for how long the patch is in a particular operational relationship with the skin (e.g., at what time of the day is the patch in full, partial or no contact with the skin and for what duration of time). Alternatively or additionally, the substrate may be arranged to determine a timing or dosage of the medicine. For example, the driver may drive the substrate at a fixed rate and/or active surfaces may be arranged on the substrate such that they are engaged at predetermined times and/or removed at predetermined times. For example, a driver may include a DC motor and/or a stepper motor and/or a linear actuator and/or a rubber band and/or a spring and/or a compressed gas drive. Alternatively or additionally a patch control device may be manually operated.

In some embodiments, the system may be operated based on a real time clock. Alternatively or additionally the system may be operated remotely, for example with a wireless/cellular connection. For example a parent and/or caretaker may use a cellular connector to remotely control drug administration to children or the elderly. For example, a patch may be stored in the assembly in a disengaged state (no substance administration) and then later engaged (that is, moved to an operational position where the substance is delivered) by authorized personnel (e.g., parent or caregiver).

An aspect of some embodiments of the current invention relates to a method for mounting a transdermal drug patch to a control device and/or a substrate and/or an adapter for mounting to the device. In some embodiments a patch may have a stationary portion and/or a mobile portion.

In some embodiments, the mobile portion of the patch may be engaged and/or disengaged to and from the skin by the patch control device. For example, a mobile portion of the patch may include one or more active and/or inactive surfaces and/or zones. Optionally a stationary portion of a patch may include an inactive zone. Alternatively or additionally a stationary portion of the patch may include one or more active surfaces. Optionally, a stationary portion of the patch may be held continuously engaged to the skin. Alternatively or additionally a stationary portion of the patch may be held continuously distanced away from the skin.

In some embodiments a patch may be attached to a substrate and/or an adaptor. For example, an active surface of the patch may be attached to a mobile portion of the adaptor. Optionally, the mobile portion of the adapter may be engaged and/or disengaged to and from the skin by the patch control device. Optionally the adaptor may include a stationary zone. Optionally, part or all of a stationary portion of the adaptor may be held engaged to the skin. Alternatively or additionally part or all of a stationary portion of the adaptor may be held distanced away from the skin.

In some embodiments, a mobile portion of a patch and/or an adaptor may be separable from a stationary portion thereof. For example, a point on the mobile portion may be distanced from a point on the stationary portion by a given distance along the surface of the substrate. When the portions are separated the distance between the points may be increased over the given distance. For example, when the substrate is lying flat on a surface (for example on a flat surface) a point on the mobile portion may be distanced from a point on the stationary portion by a given minimum distance along the surface. When the portions are separated, the minimum distance between the points may be increased over the given distance along the surface between the points when the portions are not separated. Optionally a discontinuity in the patch may intervene between the mobile region and the stationary region. For example the mobile reason may be separated from the stationary region by the discontinuity. For example, the discontinuity may include a cut and/or a cut out. For example the length of the cut and/or cut out may range between 1 to 5 mm and/or between 5 mm to 2 cm and/or between 2 to 5 cm and/or between 5 to 10 cm greater than 10 cm.

In some embodiments the stationary region may fully or partially surround the mobile region. Optionally the stationary region may not be convex. For example there may be two points located in the stationary region such that a line connecting the points along the surface of the substrate passes through the mobile region. For example there may be two points located in the stationary region such that, when the patch is lying flat on a surface a line connecting the points along the surface passes through the mobile region. For example, the minimum distance between a point in the mobile region and a point in the stationary region when separated may range between 1 mm to 5 mm more than the minimum distance between the points along the surface of the substrate when they are not separated and/or between 5 mm to 2 cm more and/or between 2 cm to 5 cm and/or 5 to 12 cm more than the shortest distance between the points along the surface of the substrate when the regions are not separated. For example, the minimum distance between two points when portions of the patch are separated may range between 1 mm to 5 mm more than the minimum distance along a surface onto which the patch is spread when the portions of the patch are not separated and/or between 5 mm to 2 cm more and/or between 2 cm to 5 cm and/or 5 to 12 cm more than the shortest distance between the points along the surface.

In some embodiment a substrate may have an adhesive on two opposite faces. For example there may be adhesive on a ventral side of the substrate for connecting to a skin of a subject and/or there may be adhesive on a dorsal side of the substrate for connection to a control device In some embodiments a discontinuity may intercede between a point on the mobile portion and a point on a stationary portion such that when the patch is laid on a surface, the distant along the surface between the points without crossing the discontinuity is greater than the distance along the surface between the two points along the surface crossing the discontinuity by between 1 mm to 5 mm and/or between 5 mm to 10 mm and/or between 10 to 50 and/or between 50 to 100 mm. A discontinuity may include for example a cut and/or a score and/or a scratch and/or a fold and/or a slit.

In some embodiments an alignment jig is supplied to facilitate alignment of a patch and/or an adaptor and/or a patch control device. Alignment may be adjusted, for example, in the lateral and/or longitudinal position and/or angular alignment. For example, achieving accurate longitudinal position may facilitate dosage control when an active surface is only partially engaged. The exact position of a patch on a device and/or on a substrate and/or on an adapter may be monitored. A patch may be optionally attached to a substrate, for example by adhesive, ultrasonic welding, heat etc. For example an alignment jig may include a cavity and/or an alignment feature that limits a position and/or orientation of a patch. The patch is optionally placed onto and/or into the alignment jig in fixed position and/or orientation. Optionally, the control device fits to the alignment jig in a fixed position and/or orientation. For example, the control device may fit into a cavity of the alignment jig in a determined orientation. Optionally when the patch and the control device are properly placed in the alignment jig, the patch may be aligned for connection to the control device. For example, when the patch has been placed onto the alignment jig in the preferred position, then the control device may be inserted into the cavity until a contact surface of the control device contacts the patch. As the control device is inserted into the cavity, the walls of the cavity optionally guide movement of the controller device until it reaches the proper position for mounting the patch to the control device. The alignment jig may optionally have a contoured surface that holds a part of a patch extended and/or recessed to match a contact service of a control device.

In some embodiments a device may be sized between 70×70 mm to 100×100 mm. Optionally the device is adapted for a large dermal patch. For example the device may control a patch having dimensions up to 70×70 mm. Alternatively the device may control a smaller patch for example 50×50 mm or 35×35 mm and/or of various shapes for example circular shape with diameter range 20 mm-70 mm. Optionally for smaller patches, for example of dimensions between 50×50 mmm to 35×35 mm and/or smaller (e.g. for lower doses between 3-10 mg) a device may be smaller, for example between 70×70 mm to 60×60 mm and/or smaller.

In some embodiments a control device may use a force to peel a patch from skin. For example a driver may exert a force on an actuator (for example including an applicator and/or a puller). For example the force may turn a roller and/or move an puller. For example, the force may range for example between 0.5 and 1 g per mm of peeling line. For example for a 70×70 mm patch the total force may range between 350 to 700 g. Alternatively or additionally the force may range between 0.1 and 0.5 g per mm peel line and/or between 1 g/mm to 3 g/mm. The force on the patch is optionally balanced by a counter force on the skin of the subject. For example, the driver may be supported on a frame of the device which is optionally attached to and/or supported by the skin of the subject.

An aspect of some embodiments of the current invention relates to protecting a patch while it is being stored in a control device. For example a liner may be supplied to separate between an active surface of the patch and a storage surface. For example, when the patch is rolled up to an inactive position, it may be stored with the liner separating between a ventral surface of one layer of the patch and a dorsal surface of the previous layer of the patch. Alternatively or additionally a liner may be part of a device. Optionally, the linear may be made of a non-stick and/or non reactive substance. Optionally, the liner may be flexible and/or impermeable.

In some embodiments, a non-reactive material of a layer, coating, surface and/or liner may be compliant against United States Food and Drug Administration (FDA) Code of Federal Regulations (CFR) 21 (for example subsection 175.300 of section 175 and/or subsection177.1550) and/or European Council (EC) directives and/or regulations for example (EC) 2023/2006 and/or (EC) 1935/2004 and/or (EC) 1272/2008. Optionally the coating is non-oxidizing. Optionally, the material may be dense and/or nonporous for example to prevent growth of mold and/or bacteria. For example the material may produce little or no residual when exposed to water and/or heptanes and/or alcohol (for example 8%) for between 1 to 24 and/or 24 to 150 hours at temperature between −20 to 50 degrees C. and/or between 50 to 100 degrees C. and/or between 100 to 200 degrees C. at normal and/or high pressure. For example residuals may be less than 150 parts per million (ppm) and/or less than 50 ppm and/or less than 2 ppm. For example, a non-reactive material may include Polyethylene and/or paper coated with polyethylene.

In some embodiments, a non-active surface of a patch and/or adapter and/or a ventral surface thereof and/or a ventral surface of a control device and/or a frame of a control device may be attached to skin using nonwoven tape for example 3M 1776. For example, a non-active surface of a patch and/or adapter for example a dorsal surface thereof may be attached to a control device by single and/or double sided adhesive, for example 3M 1522. In some embodiments, a substrate (for example a patch and/or an adaptor) may be configured for connection to a control device. Optionally, a surface and/or an edge of a mobile portion of the substrate may be configured for attachment to the device and/or an actuator thereof. Optionally, a surface and/or an edge of a stationary portion of the substrate may be configured for attachment to the device. For example, a part of a dorsal face of the patch may be connected to the control device. Alternatively or additionally an edge of the patch may be connected to the control device. For example, the attachment may be by means of an adhesive and/or a magnet and/or a clip and/or a hook and/or a slit.

In some embodiments, the mobile portion of the substrate will be configured to attach to an actuator and/or mobile portion of the device and/or be engageable and/or disengageable to the skin of a subject. Optionally the stationary portion of the substrate will be configured to attach to an immobile portion of the device and/or a frame of the device and/or be stationary with respect to the skin of a subject (for example, remaining engaged and/or disengaged as long as the device is attached).

Some embodiments of the system of the invention may be advantageous in "chronotherapy", in which drug delivery is timed in accordance with a body rhythm, for example a circadian rhythm and/or a rhythm of a disease. In some embodiments, chronotherapy, may increase therapeutic efficacy and/or reduce side effects in comparison to constant delivery. Optionally, dose control may be programmed to deliver redefined doses that coincide with peak disease symptoms. For example, this may be useful when symptoms peak at night while asleep or immediately upon waking.

Circadian rhythms may be described as physical, mental and behavioral changes that follow a roughly 24-hour cycle and/or respond to light and darkness in an organism's environment. Circadian rhythms may is some cases influence sleep-wake cycles, hormone release, body temperature and other important bodily functions. They have been linked to various sleep disorders, such as insomnia. Abnormal circadian rhythms have also been associated with obesity, diabetes, depression, bipolar disorder, seasonal affective disorders, asthma attacks, coronary infarction, angina pectoris, stroke and ventricular tachycardia, among others.

In some embodiments, a control system will not interfere with the active portion and/or action of a drug patch. For example, the device may not interfere with the chemical composition and/or physical properties of some, any or all of the patch reservoir and/or the adhesive and/or the release liner. Optionally changes will occur in aspects of the active portion of the patch due to exposure or protection from contact with skin. For example by removing the active surface from the skin of a subject and/or protecting the active surface, chemicals that would have diffused out of the patch may remain and/or build up and/or change concentration. In some embodiments, the dosage control system does not compromise the active envelope and/or stack of the patch either with energy, chemical and/or physical means. In some embodiments, the dosage control system does not add any intervening substance between the active surface of the patch and the skin of a subject.

In some embodiments a dosage control system may work with a conventional drug patch. For example the drug patch may have a predetermined delivery behavior. Optionally the predetermined delivery behavior may depend on characteristics of the subject and/or his skin. Optionally the active surface of the patch will be substantially uniform over 70% and/or 90% of its surface. For example the patch may not include control regions and/or programmable components and/or a sensor.

In some embodiments, the present invention may be used to facilitate transdermal drug administration of any drug including for example Clonidine, Diclofenac Epolamine, Estradiol, Levonorgestrel, Norethindrone Acetate, Norelgestromin, Ethinyl Estradiol, Fentanyl, Lidocaine, Tetracaine, Methylphenidate, Nitroglycerin, Amlexanox, Oxybutynin, Rifastigmine, Scopolamine, Selegiline, Testosterone, Nicotine, Methyl Salicylate, Menthol, Epinephrine, Rotigotine and/or any combination thereof.

In some embodiments, the present invention may be used to facilitate drug administration with an existing transdermal system, for example Catapres TTS, Flector, Vivelle, Climara, Vivelle-Dot, Alora, Menostar, Estraderm, Climara Pro, Combipatch, Ortho Evra, Duragesic, Lidocanine, Synera, Daytrana, Nitro-Dur, Minitran, Oradisc A, Oxytrol, Exelon Patch, Transderm-Scop, Emsam, Androderm, Nicoderm, Habitrol, Prostep, Salonpas.

Some embodiments of a system according to the current invention may be used to transdermally deliver an active drug (for example propranolol, nifedipine, verapamil, enalapril, isosorbide 5-mononitrate and digoxin, an anti-asthmatic (e.g. theophylline and terbutaline), an anticancer drug, a psychotropic drug, an analgesic, a local anesthetics and/or an antibiotic).

An aspect of some embodiments of the current invention relates to a guide movement of a patch storage roller. Optionally the guide may be at an angle to a skin contact surface. For example, the guide may keep an edge of a rolled up patch within a desired range of distance from a skin even as the radius of the roll changes.

An aspect of some embodiment some embodiments a guide may adjust a rate of rotation per linear movement, for example to balance uptake and/or release of a patch and coverage of a skin of a user.

An aspect of some embodiments of the current invention relates to an alignment jig for attaching a flexible transdermal patch to a control device. For example, the patch may be placed on a surface of the alignment jig. The control device may be placed against the patch with the patch sandwiched between one or more attachment surfaces of the control device and the surface of the alignment jig. Optionally the surface of the alignment jig includes a protrusion to increase connection between a connection zone of a patch and a recessed portion of the contact surface of the control device. For example, a recessed portion may include a curved surface, for example of a roller.

An aspect of some embodiments of the current invention relates to transdermal medical patch controller that engages and/or disengages a patch to a user's skin. Optionally the control device includes a window through which a user can see the patch and/or visually determine whether the patch is engaged, disengaged and/or partially engaged. For example the window may be positioned for viewing the portion of the patch that is placed against the skin. For example the window may be positioned for viewing a separation line between an engaged portion of the patch and/or a disengaged portion of the patch. For example the window may be positioned for viewing a position of a mechanism that stores and/or engages the patch (for example a roller that stores a rolled up portion of the patch and/or rolls an engaged portion of the patch onto the skin).

An aspect of some embodiments of the current invention relates to arrangement of a drive system of a transdermal medicine patch controller. For example, the device may include a base with a skin contact surface and/or an opening through which the patch is applied to the skin of a user. Optionally, part or all of the drive system (for example including most or all of a motor and/or an energy source and/or a printed circuit board [PCB]) are located beside the opening and/or over the skin contact surface. For example, when the patch is disengaged from the skin it may be stored as a roll rolled up on a roller. Optionally the total height of the device (and/or of 98% of top area of the device and/or 95% of the top area and/or 90% of the top area and/or 80% of the top area and/or 50% of the top area) may be less than the combined height of the roller and the motor and/or the roller and the energy storage device and/or the roller and a transmission (for example the transmission may include a drive shaft and/or an associated drive gear). For example, the drive system and/or the motor and/or the energy source and/or at least 90% thereof by weight and/or at least 70% thereof may be mounted below the height of the roller with the patch.

An aspect of some embodiments of the current invention relates to an alignment jig for attaching a flexible transdermal patch to a control device. Optionally, the patch may be placed on the alignment jig with an attachment surface of the path covered by a protective liner. For example, the patch may be placed on a surface of the alignment jig. The control device may be placed against the patch with the patch sandwiched between one or more attachment surfaces of the control device and the surface of the alignment jig. Optionally the protective liner may be peeled from the patch after placement of the patch on the alignment jig and/or while the patch is positioned between the attachment surface of the control device and the surface of the alignment device. For example a peeling tab of the liner may protrude out of the alignment jig and/or out from in between the attachment surface of the control device and the attachment surface of the alignment jig. Optionally the liner is peeled away from the patch by pulling the tab away from the patch and/or away from the alignment jig and/or away from the space between the attachment surfaces of the alignment jig and the control device. For example, the liner may be folded over and/or doubled over such that pulling the tab peels the folded portion across the attachment surface of the patch.

An aspect of some embodiments of the current invention relates to biasing a patch towards a subject. For example, a patch may have an elastic layer that causes the patch to bias away from a rolled up state. Alternatively or additionally, biasing may result from the rate of release of the patch. Optionally the rate of release of the patch may be greater than the rate of deposition of the patch on the skin a patch may be unrolled faster than it is deposited onto a surface and/or the patch may have a structure that inhibits folding up. Optionally the result of the biasing is that the patch is pushed outward from the device. The outward pushing of the patch may also push the patch against a surface like the skin of a subject.

Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Delayed Engagement of an Active Surface of a Medicine Patch

Referring now to the drawings, FIG. 1 is a flow chart illustrating a method of delayed engagement of an active surface of a drug patch in accordance with some embodiments of the present invention. In some embodiments, a device is supplied 102 with a drug patch stored 104 in the device. Optionally the device is placed 104 on a user's skin. The patched is then engaged 108 to the user's skin after a delay 106. For example the patch may be engaged 108 by the device according to a preprogrammed time and/or in response to a command and/or in response to an event. When the patch is engaged 108 to the skin of the subject, it optionally treats 107 a condition for example by releasing a drug and/or preparing the skin and/or other treatment. For example that patch may treat the epidermis to improve the drug delivery. Optionally at the end of treatment 107 the device and/or patch may be removed 110 from the subject. Alternatively or additionally the device may disengage the patch and/or engage more active area of the patch (for example as described herein in further embodiments). Alternatively or additionally, the system may be designed to release a measured dose and/or remain active for a limited time and/or cease and/or switch without external intervention.

In some embodiments, a device may be supplied preloaded with a patch from a supplier (for example a drug producer and/or a manufacturer). Optionally the patch may be supplied in a stored state and/or ready to use. For example a user may receive a ready device and/or may place the device on his skin and/or activate the device. Alternatively or additionally, a device may need to be primed before use. For example, a protective liner may be exposed. For example, before placement 104 the liner may be removed by a user. Optionally before placement 104 of the device on a subject, the patch may be moved to a storage position. For example the patch may move to the storage position automatically upon opening a storage container (for example a blister) and/or in response to another step in priming of the device (for example in response removing a protective liner) and/or by a command.

In some embodiments, a patch may be supplied separate from the engagement device. For example, a patch may be included in package with the device and/or supplied entirely separately from the device. Optionally the patch may be packaged in a protective package.

In some embodiments, a patch may be designed for manual placement on the skin without the engagement device, for example a conventional patch. Optionally, an interface may be supplied to connect the patch to the device. Alternatively or additionally, the patch may be connected directly to the device. Alternatively or additionally, a patch may be designed and/or packaged for use with the device.

Optionally, the user may remove the patch from a protective wrapper and/or load the patch to the device. Alternatively or additionally, a patch may be an integral part of a cartridge and/or device. For example, the cartridge may be disposable and/or single use while the controller and/or driver may be reused. Alternatively or additionally, the entire device may be disposed of for example with a used patch.

In some embodiments, the device may engage 108 the patch to the subject (for example by putting an active portion of the patch in contact with the skin of the subject). Optionally, engagement 108 may occur after a time delay 106. For example, time delay 106 may be preprogrammed. Alternatively or additionally, engagement 108 may be in response to a command. Alternatively or additionally, engagement 108 may be in response to an event. For example, a sensor may detect a medical condition requiring treatment and the device may respond by engaging 108 the patch. Alternatively or additionally engagement 108 may be in response to compound trigger (for example a sensor may alert a medical professional who may transmit a command to engage 108 the patch and/or a patch may be engaged in response to a certain sensor output only at certain times and/or under certain conditions [for example the patch may be engaged only when a cumulative dosage in a determined time period is with a specific range]).

In some embodiments a patch engaging device may include a logical controller, for example a processor. Optionally the processor will give commands to engage 108 the patch according to preprogrammed instructions and/or received data and/or received commands. Alternatively or additionally a device may progressively meter out a patch having one or more active surfaces. When an active surface is engaged 108 it may perform a treatment 107 for a predetermined period and/or until it is disengaged for example by being removed 110. Optionally, the device may perform the disengagement of the patch (for example as described in various embodiments herein).

In some embodiments, a delayed patch engaging system may be useful for convenience and/or safety. For example, when a subject is to receive a drug at night, a device may engage a patch at a predetermined time without needing to depend on the subject waking up and remembering the drug. In some embodiments, the machine may engage the patch without disturbing the subject's sleep. Alternatively or additionally, the device may be used to engage a patch to a subject who has limited ability of self administration. For example a patch may be engaged to a physically disabled subject and/or a mentally limited and/or senile subject without requiring the presence of a caretaker, for example at an inconvenient time. Alternatively or additionally, a device may be used by a veterinarian to engage a patch to an animal at a prescribed time without needing the veterinarian to be present. Alternatively or additionally, the device may be used to apply a dose to subject under monitoring whenever and/or wherever an acute condition occurs. Alternatively or additionally, a delayed engagement device may be used to maintain a determined dosage. For example as a patch is depleted, the device may progressively engage more of the patch, maintaining a constant dosage and/or the speed of engaging may be controlled to maintain a desired dosage regime (for example through a preprogrammed engaging regime and/or speeding or slowing engagement in response to a sensor). Alternatively or additionally, the device may be used to increase the level of compliance in environments where compliance is a critical and/or problematic (for example treatment of mental patients and/or chemotherapy and/or drug testing). For example use of a delayed patch engagement device may reduce the requirements of subject supervision and/or associated subject time in a hospital and/or clinic. Alternatively or additionally the device may be used for non-medicinal drugs and treatments. For example, a device may engage a patch with a drug against motion sickness to a sleeping subject a few hours before an early morning flight and/or a device may engage a patch including a stimulant a to a subject shortly before he needs to wake up.

Automatic Disengaging of Medicine Patch

Figure 2:
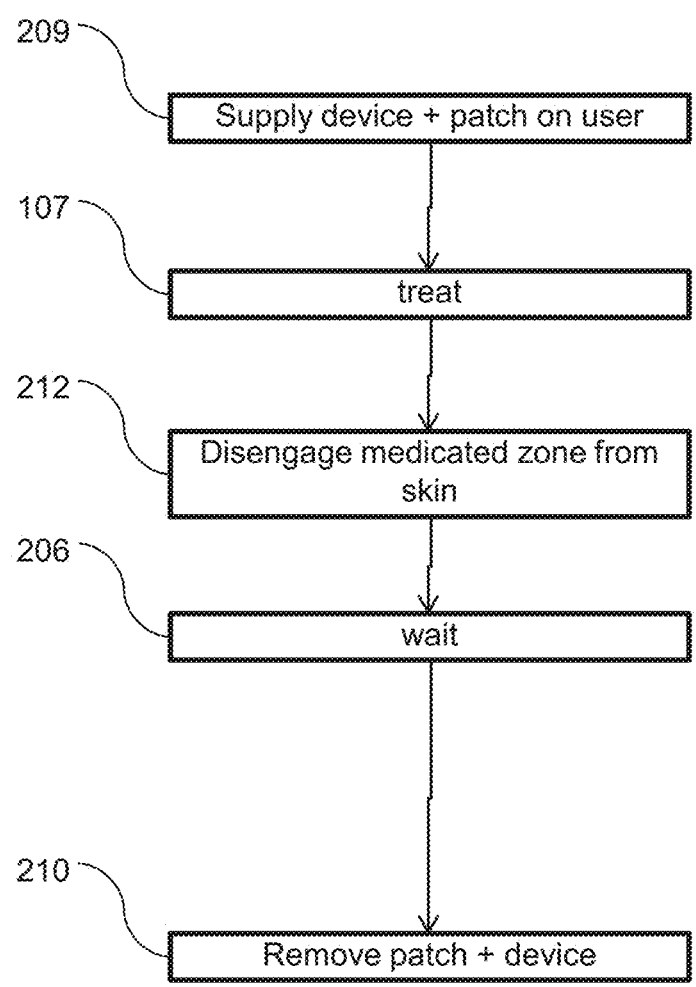
FIG. 2 is a flow chart illustrating a method of disengaging an active surface of a medicine patch in accordance with some embodiments of the present invention.

FIG. 2 is a flow chart illustrating a method of disengaging of a medicine patch in accordance with some embodiments of the present invention. In some embodiments, a device may be used to disengage 212 a drug patch from a subject. For example, a disengagement device may be supplied 209 on a user being treated 107 with a drug patch. Optionally when the treatment should be stopped, the device will disengage 212 the patch from the skin of the subject. Once the patch has been disengaged 212 the device and/or patch may be removed 210 at a convenient time.

In some embodiments, a user may place a device on a subject in an engaged state. The device may leave the patch on during a treatment 107 and then remove the patch. Alternatively or additionally, a machine may be used to perform delayed engagement of a device (for example as described in the previous embodiments) and then to perform disengagement 212. Optionally the user may load the drug and/or prime the device and/or place the device onto the subject. Alternatively or additionally a user may receive a device preloaded and/or preprimed.

In some embodiments, a device may disengage 212 a patch according to a command and/or in response to a condition (for example in response to a sensor signal) and/or at a preprogrammed time. Optionally, a disengagement time may be programmed into a controller of the device, for example a processor. Alternatively or additionally, the device may progressively remove a patch having active surfaces located at predetermined locations along the patch thereby being removed at a predetermined time. The programming is optionally done by a manufacturer and/or by a user. In some embodiments after disengagement 212 of a patch, the patch and/or the device may be removed 210 and/or disposed of. Optionally, removal of the device may be immediate. Alternatively or additionally, removal may be after a time delay 206. Alternatively or additionally disengagement 212 of the patch may be reversible. For example, the device may store the disengaged patch and/or engage the patch after storage (for example as described in various embodiments herein).

In some embodiments a patch disengagement device may be used to reduce subject supervision and/or shorten subject time in a hospital or clinic. For example, a subject who would otherwise be required to remain in a clinic to make sure a patch is properly disengaged, may be administered a patch with a device and sent home. For example a patch disengagement device may be used to prevent accidental overdose due to neglecting to remove a patch. For example, a device may remove a patch at a fixed time before an overdose would occur and/or a device may have a sensor that detects initial signs of an overdose and removes that patch before the overdose. Alternatively or additionally, a patch removal device may be under control of a subject and/or may be used to monitor the use of a medicine patch (for example dosage, timing and/or compliance). Alternatively or additionally a patch removal device may be used to remove a patch at an inconvenient time (for example to remove a sleeping drug patch after a subject has gone to sleep and/or to remove a patch from a subject early in the morning without requiring a subject to get up and/or a caretaker to come).

Controlling of Dosage of a Medicine Patch

Figure 3:
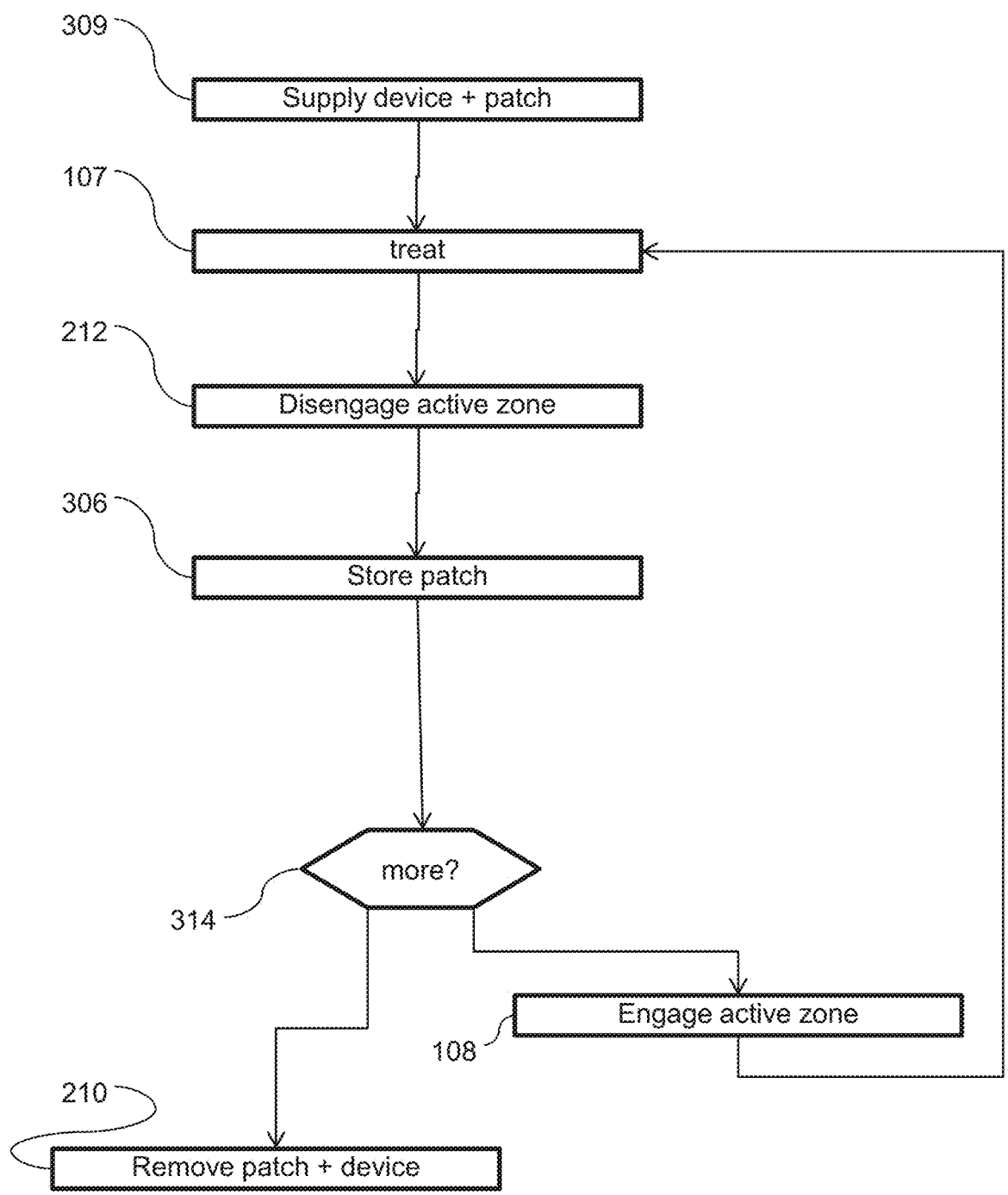
FIG. 3 is a flow chart illustrating a method of reversibly engaging and disengaging an active surface of a medicine patch in accordance with some embodiments of the present invention.

FIG. 3 is a flow chart illustrating a method of reversibly engaging and disengaging of a medicine patch in accordance with some embodiments of the present invention. In some embodiments, a device may reversibly and/or repeatedly engage and/or disengage a medicine patch. For example, a patch may have an active surface for treatment of a subject. The device may repeatedly disengage 212 the active surface from the subject and/or engage 108 the active surface. Optionally, while the active surface is disengaged, it is stored for re-engaging 108. Optionally, before and/or during storage, the patch may be protected for example by placing a liner over an active area of the patch while it is being stored 306. Alternatively or additionally, the patch is stored rolled about itself and/or rolled around a liner or an inflatable mesh. Optionally a patch may be disengaged by blocking contact between the active surface of the patch and the skin In some embodiments a patch and or device may be supplied 309 to a subject. Optionally the device may be preloaded. Alternatively or additionally the device may require loading. Optionally the device may be preprimed. Alternatively or additionally the device may require priming. In some embodiments the device will be supplied 309 in an engaged state. For example, treatment 107 may immediately start when the device is placed on the skin of the subject. Alternatively or additionally, the device may be supplied 309 in a disengaged state. For example, treatment 107 and/or engagement 108 of the patch may start after a delay.

In some embodiments, after a period of treatment 107, a patch may be disengaged 212 and/or stored 306. During and/or prior to storage 306, the patch may be protected, for example from contamination and/or depletion. After disengagement, a decision may be made whether to administer more 314 treatment 107. The decision to administer more 314 treatment 107 may optionally be preprogrammed. For example, a processor in the device may be programmed to continue treatment 107 according to a time schedule and/or dependent on a sensor input and/or based on commands communicated to the processor. Alternatively or additionally, the patch may be formed to perform a particular treatment regime. For example, active and/or inactive surfaces may be distributed along the patch such that the device progressively engages and/or disengages various zones at different times. For example, the device may progressively engage and/or disengage parts of the patch. Optionally, according to the configuration of the patch active and/or inactive surfaces may be engaged and/or disengaged.

In some embodiments a reversible patch engaging/disengaging device may be used to maintain a dosage regime and/or medicine concentration over an extended period. For example, maintaining a dosage may compensate for the dosage rate reduction resulting from aging and/or use of the patch, for example a change of drug concentration in the patch due to depletion. For example a control device may be used to set a pharma kinetic level (PK) in the blood. For example fresh patch may be applied and/or a patch may be applied over fresh of skin. For example, fresh application may stabilize the total transfer in spite of degradation in the skin and/or patch.

Device for Controlling Engagement of a Medicine Patch

Figure 4:
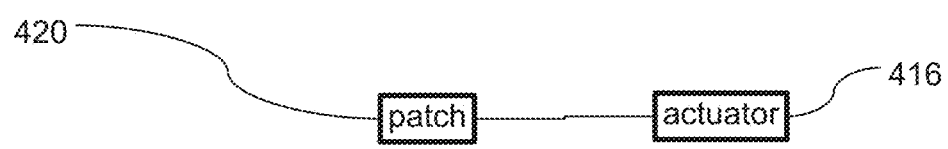
FIG. 4 is a block diagram illustrating a device for controlling engagement of a drug patch in accordance with an embodiment of the current invention.

FIG. 4 is a block diagram illustrating a device for controlling engagement of a drug patch in accordance with an embodiment of the current invention. In some embodiments, a patch controlling device may include an actuator 416. For example actuator 416 may initiate, increase, decrease and/or interrupt administration of a drug from a patch 420. Optionally the patch 420 includes a conventional fixed dose drug patch. Alternatively or additionally a patch may be a custom patch. For example, custom patch may include an active area of a conventional patch, for example approved for use for a fixed dosage mounted on a custom substrate and/or custom periphery.

In some embodiments an actuator may be mobile with respect to a frame and/or a subject contact surface of the device. Optionally, actuator 416 may include a roller. For example a roller may roll a patch onto and/or off of a subject. Alternatively or additionally an actuator 416 may include a substrate (for example a flexible belt and/or a flexible strip and/or a ductile actuator [for example that changes shape to engage and/or disengage a portion of a patch for example substrate 1558 of FIGS. 15A-15C].

In some embodiment patch 420 may include a single active region and/or multiple active regions. Optionally, different active regions may have the same drug formulation. Alternatively or additionally different active regions may include different drugs and/or formulations.

Figure 5A:
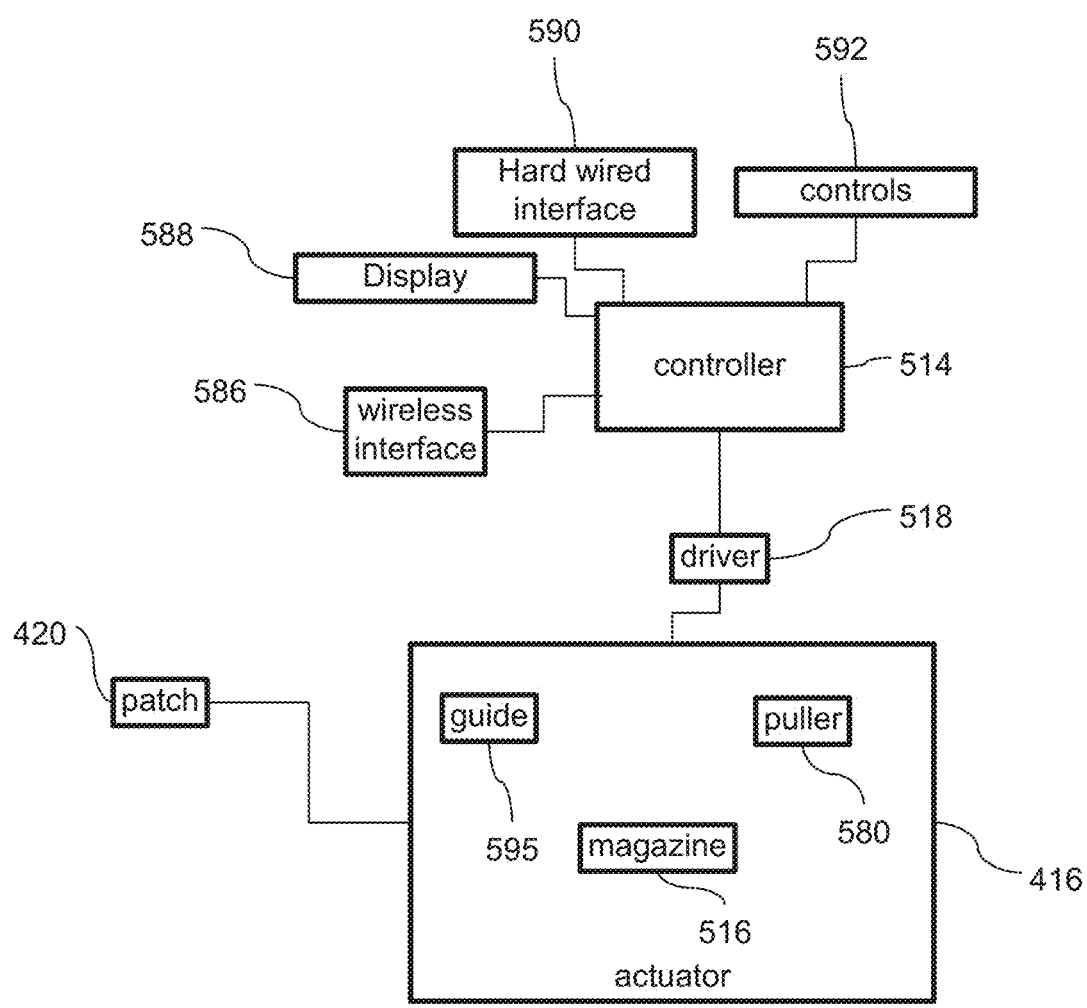
FIGS. 5A-5B are a block diagrams illustrating further optional features of a device for controlling engagement of a drug patch in accordance with some embodiments of the current invention.

FIG. 5A is a block diagram illustrating further optional features of a device for controlling engagement of a drug patch in accordance with an embodiment of the current invention. In some embodiments, a patch controlling device includes a controller 514. For example controller 514 may be programmable. Optionally controller 514 controls a drive 518 which powers an actuator 416 to switch patch 420 between operation states (for example fully engaged, fully disengaged and/or partially engaged). Optionally actuator 416 may include one or more mechanical sub elements. For example mechanical elements may manipulate patch 420. For example a guide 595 may direct a separation line between a patch and skin of a subject. Optionally a puller 580 may pull a portion of a patch 420. For example puller may pull a patch away from skin of a user and/or put tension on patch 420 keeping it connected to guide 595. Optionally, a patch control device may include a repository 516 for storing a patch.

In some embodiments, a guide may include a roller that rolls along and/or directs a separation line where a patch is separated and/or united with the skin of the subject. Alternatively or additionally a guide may include a sliding object and/or a wiper and/or flattening element and/or a straight edge that directs the separation line.

In some embodiments, a repository 516 may include a roller that stores a patch, for example by rolling it up. Alternatively or additionally a repository 516 may include a region inside a housing and/or a substrate that holds a patch stored away from the skin of the subject.

In some embodiments, a puller and/or an applicator may include a roller that keeps tension on a patch, for example as illustrated by puller 816a of FIG. 8C. Alternatively or additionally a puller and/or an applicator may include an elastic substance and/or a spring and/or a connection to a housing that keeps tension on a patch. Optionally, a puller alone and/or in combination with a guide may pull and/or peel a patch. Optionally a patch may be pulled and/or peeled a peeling angle for example between 0 to 10 degrees from the horizontal and/or between 10 to 45 degrees and/or between 45 to 80 degrees and/or between 80 to 100 degrees and/of between 100 to 135 degrees between 135 to 170 degrees and/or between 170 degrees to 180 degrees where is 0 degrees is pulling the separation line directly towards a separated edge, 90 degrees is pulling the patch directly away from the skin and 180 degrees is pulling the patch directly toward a zone where the patch is adhered to the skin.

In some embodiment a single component may pull and/or guide a separation line and/or store a portion of the patch. For example when roller 816a of FIG. 8A optionally disengages patch 820, roller 816a optionally pulls up on the free end of the patch and/or roller 816a optionally stores patch 820 by wrapping it around roller 816a and/or guides separation line 876a.

In some embodiments, a user interface is provided, for example including a wireless interface 586. For example a subject may use a personal computing device (for example a smart phone) to communicate with controller 514 over a wireless interface. For example, a cell phone may output status information of the control device and/or a user may use the cell phone as an input device to control and/or program the patch control device. Optionally a patch control device may include a dedicated display 588. For example display 588 may include a status indicator, for example a LED that shines green when working properly and/or red on a malfunction. Alternatively or additionally display 588 may include a LCD display giving alpha-numeric messages. In some embodiments a patch control device may include a hard wired port 590, for example a charger port and/or a hard wired communication port and/or a combination port for example an USB port. Alternatively or additionally a patch control device may include local controls 592 for example a button and/or a switch. For example, local controls may include an on/off switch and/or a toggle switch to increase and/or decrease a dosage.

Figure 5B:
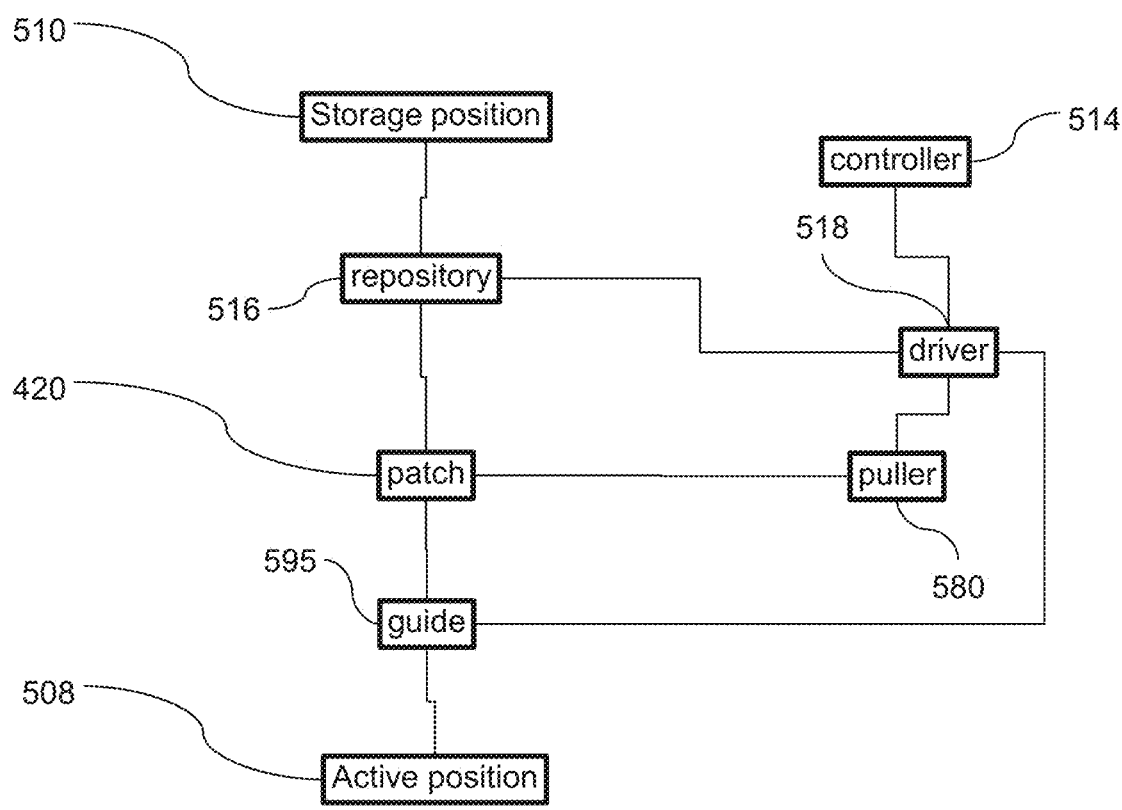

FIG. 5B is a block diagram illustrating further optional features of a device for controlling engagement of a drug patch in accordance with an embodiment of the current invention. In some embodiments, a patch controlling device initiates and/or increases a rate of deliver by engaging an active surface of a patch and/or a portion thereof. In some embodiments, a patch controlling device may interrupt and/or reduce a rate of deliver by disengaging an active surface of a patch and/or a portion thereof. An actuator is optionally driven by driver 518. Optionally driver 518 is controlled by a controller 514.

In some embodiment, an actuator includes a repository 516 and/or a guide 595 for example to engage a patch by moving an active surface from a storage position 510 to an active position 508 and/or a puller 580. In some embodiments, a puller 580 disengages patch 420 by moving the active surface from the active position 508 to the storage position. In some embodiments, an actuator may be configured to activate a patch only without deactivating the patch. Alternatively or alternatively an actuator may be configured to deactivate a pre-activated patch. Alternatively or additionally, in some embodiments an actuator may be configured to activate and deactivate patch 420.

In some embodiments, controller 514 may include a processor and/or a communication interface and/or a memory. Optionally controller 514 may receive input from a local and/or remote user and/or a sensor.

Figure 6:
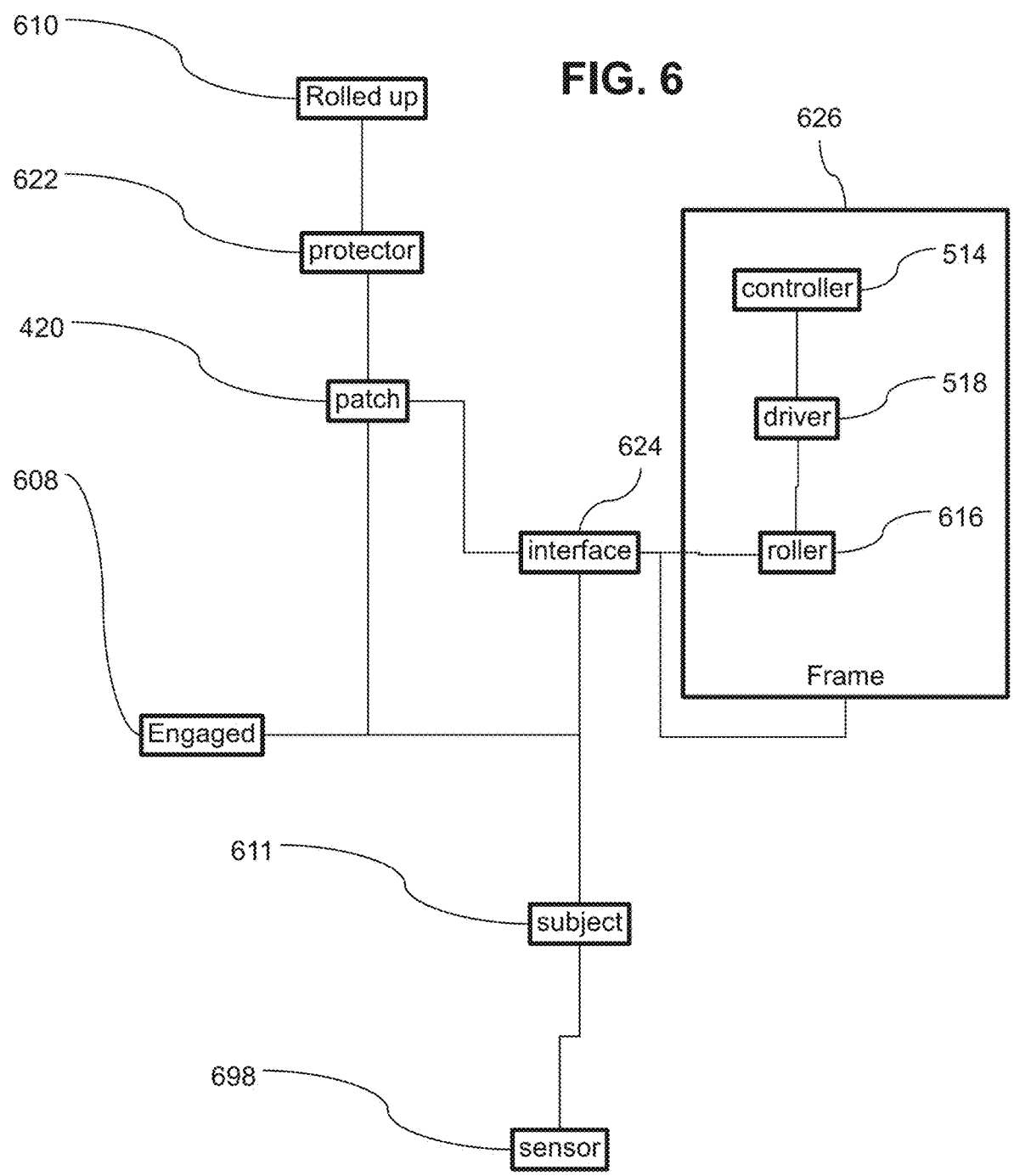
FIG. 6 is a block diagram illustrating further optional features of a device for controlling engagement of a drug patch in accordance with an embodiment of the current invention.

FIG. 6 is a block diagram illustrating further optional features of a device for controlling engagement of a drug patch in accordance with an embodiment of the current invention. In some embodiments an actuator may include a roller 616. For example in the stored position, patch 420 may be rolled up onto roller 616. Optionally a protector 622 to protect a patch in the storage position (e.g. rolled up 610 on a roller). For example, a protector may include a liner separating between layers of patch 420 rolled up on roller 616.

In some embodiments, an adapter, for example interface 624 may connect between patch 420 and the patch controlling device. For example, interface 624 may include a substrate connecting to patch 420. Alternatively or additionally a portion of interface 624 may be configured to connect to roller 616 and/or a frame 626 of the patch control device. For example, a mobile portion of the interface may be connected to the roller and/or a stationary portion of interface 624 may be connected to frame 626.

In some embodiments, driver 518 may reposition and/or rotate roller 616 to move patch 420 from the rolled up 610 stored state to and engaged 608 state contacting a skin 611 of a subject. Optionally, driver 518 may reposition and/or rotate roller 616 to disengage patch from skin 611 and/or roll the patch to the rolled up 610 storage position.

In some embodiments, a patch dosage regulator may be responsive to an event and/or a condition of the subject and/or a sensor output. For example, a sensor 698 may monitor a condition of a subject. Optionally, sensor output may be sent to controller 514. Alternatively or additionally, sensor output may be sent to an external decision maker (e.g. a processor and/or a person) who may send a message to controller 514. Based on the sensor output controller 514 may engage and/or disengage a drug patch and/or increase and/or decrease a dosage. For example sensor 698 may measure one or more of a blood flow, posture, heart rate, a blood oxygen content, breathing rate, temperature.

Loading a Patch to a Control Device

Figure 7A:
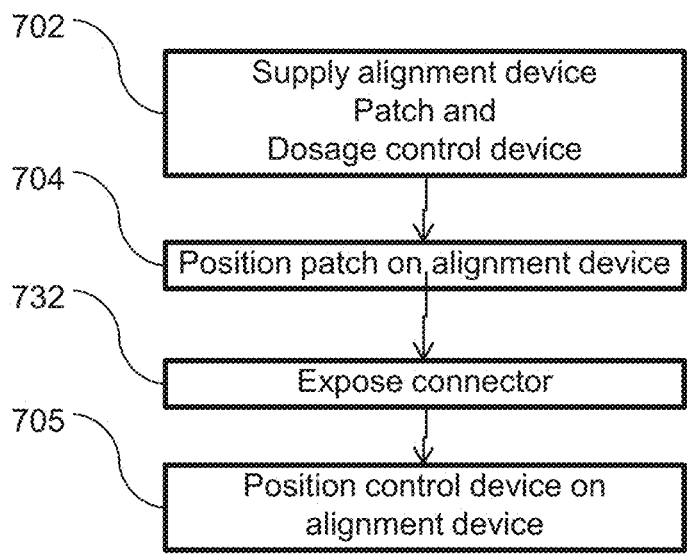
FIGS. 7A-7B are flow chart illustrations of methods of loading a patch to a dosage control device in accordance with embodiments of the present invention.

FIG. 7A is a flow chart illustration of a method of loading a patch to a dosage control device in accordance with an embodiment of the present invention. In some embodiments, an alignment jig and a patch and a control device are supplied 702 such that positioning 704 the patch and positioning 705 the control device onto the alignment jig loads the patch to the control device.

Figure 14:
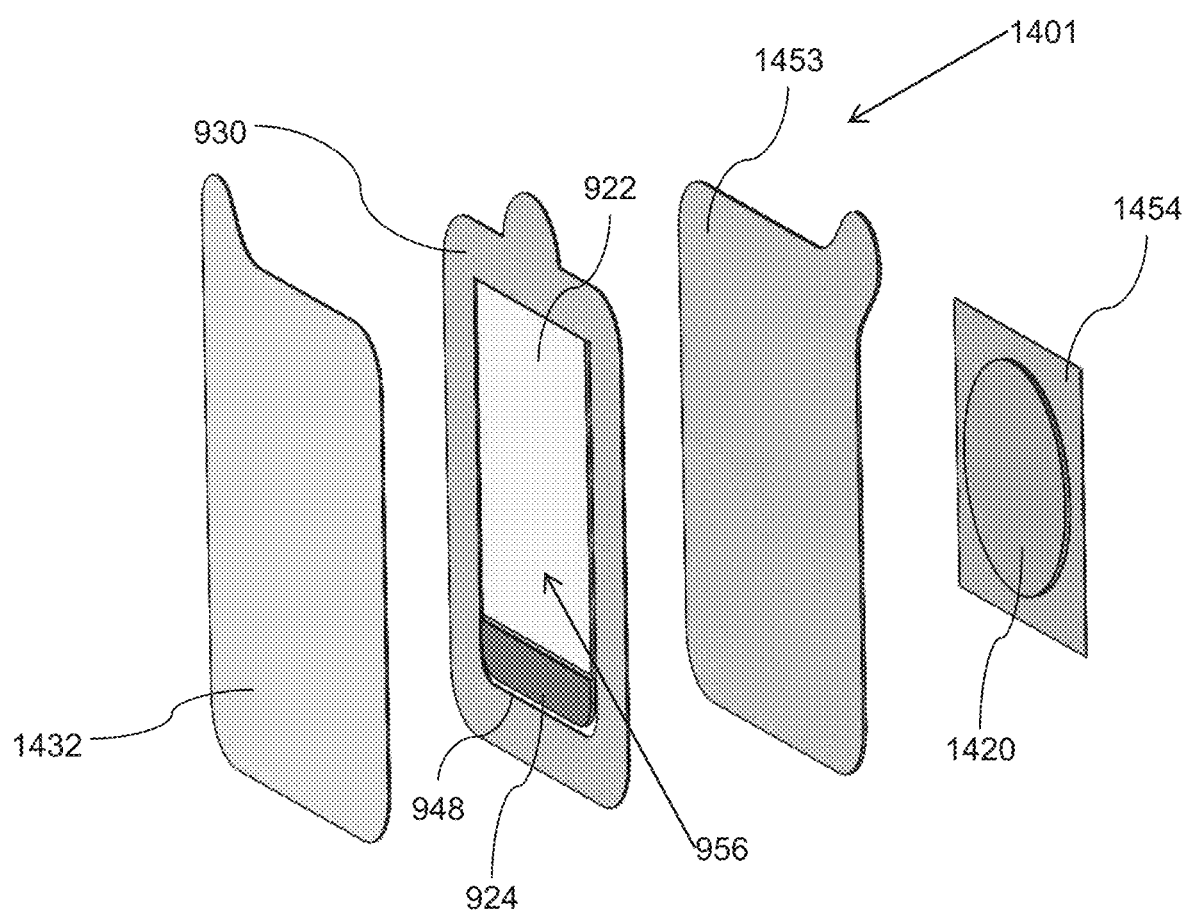
FIG. 14 is a schematic illustration of an adapter for connecting a patch to a patch control device in accordance with an embodiment of the current invention.

In some embodiments, a patch may be preloaded into an alignment jig. Alternatively or additionally a user may place 704 the patch onto the device. For example a user may place the ventral face of patch 920 onto base 939 of device 940. Alternatively or additionally, the patch may be supplied preloaded to the alignment jig. Optionally a user may remove a liner from the patch to expose 732 a connector (For examples removing dorsal liners 1232 from patch 920 and/or liner 1432 of from adapter 1401, for example as illustrated in FIG. 14, exposes 732 connector 924). Optionally there may be a tab 1254. For example, tab 1254 may be used to peel a liner off of patch 920.

In some embodiment, the dosage control device may be placed 705 onto the patch and jig. Optionally the jig includes an alignment feature and/or a guide. For example, the jig may orient the control device to properly connect to the patch. Optionally, the jig includes a further connector (for example a clip and/or a snap and/or a hook and/or an interference element and/or a magnet). For example, the further connector may lock the control device onto the jig and/or may pressure the control device onto the patch.

Figure 7B:
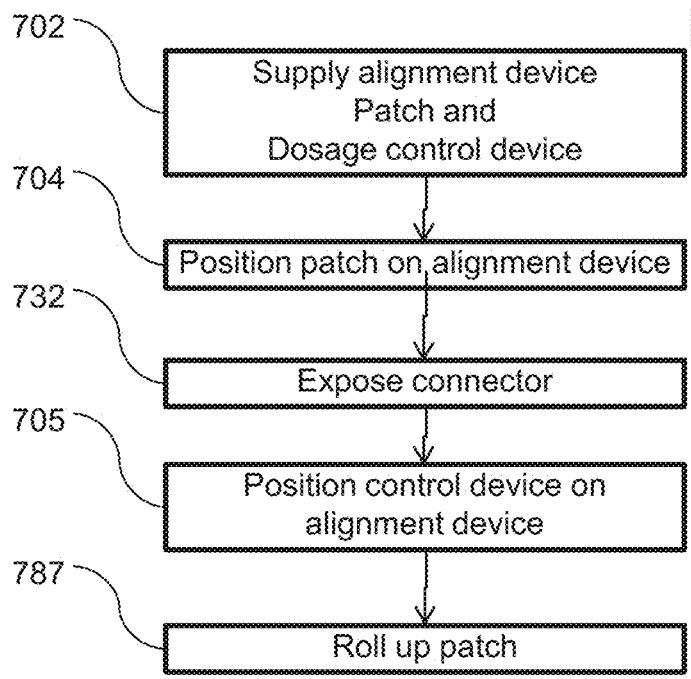

FIG. 7B is a flow chart illustration of a method of loading a patch to a dosage control device in accordance with an embodiment of the present invention. In some embodiments, after the patch is connected to the control device, an actuator of the control device may move the patch to a storage position, for example by rolling 787 the patch onto a roller. Optionally the moving of the patch may be user initiated and/or automatic. For example, automatic movement and/or rolling up of a patch may be initiated automatically when the control device is placed onto the jig and/or when it is removed from the jig.

Patch Roller

Figure 8A:
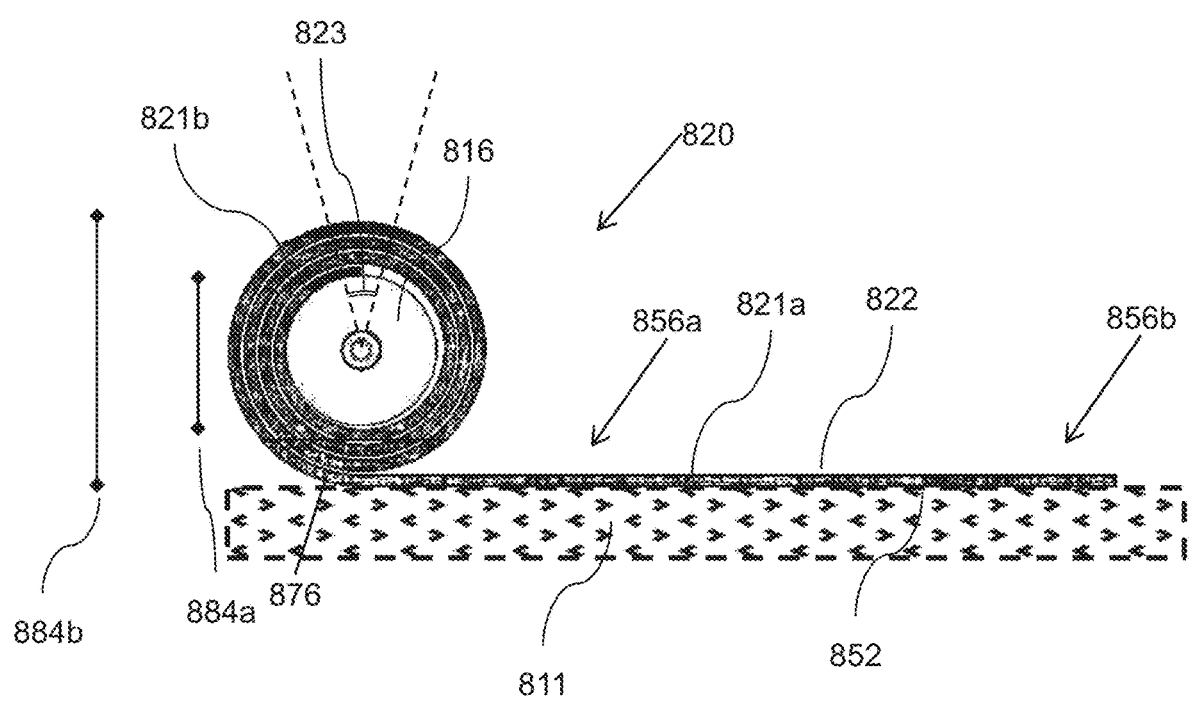

FIG. 8A is a perspective side view of a roller in which optionally guides a separation line. A roller optionally also pulls a patch and/or stores a patch in accordance with an embodiment of the present invention. In some embodiments, patch 820 is stored by rolled up onto a roller 816a. Optionally, roller 816a engages a portion 821a of patch 820 by unrolling portion 821a of the patch along a separation line 876a onto a skin 811 of a subject. For example, in the view of FIG. 8A, roller 816a rolls leftward to engage and/or unrolls patch 820 onto skin 811. Optionally, roller 816a disengages the patch for example by pulling and/or peeling the leading edge of the patch from the skin. For example, in the view of FIG. 8A, roller 816a rolls rightward to roll up and/or disengage patch 820 from skin 811.

In some embodiments, the diameter of a rolled up patch 820 may increase as more patch 820 is rolled up. For example, before the patch starts being rolled up, the total diameter may be roller diameter 884a. As the patch is rolled up, the roll diameter 884b may increase. For example, the roller diameter 884a may start at 8 mm and roll may grow for example to a roll diameter 884b of about 20 mm as the patch is loaded onto roller 816a.

In some embodiments, patch 820 includes an active zone 856a and/or an inactive zone 856b. For example, inactive zone 856b may have an active surface on a ventral face thereof and/or may be on the trailing edge of patch 820. Optionally, when patch 820 is fully rolled up onto roller 816a, only a trailing section including inactive zone 856b is in contact with skin 811 and/or active zone 856a is not in contact with the skin. Optionally, when active zone 856a is not in contact with the skin, no treatment occurs. Alternatively or additionally, different zones of a patch may include different drugs for different treatments. For example, zone 856a may include a first drug that is applied to skin 811 from the beginning of a treatment and zone 856b may have a different drug which is applied to the skin later in the treatment.

In some embodiments, patch 820 includes a skin attachment surface 852 on a ventral side thereof. Optionally, a dorsal side of the patch is covered by a protector 822. For example, protector 822 may include a liner. Optionally protector 822 includes a chemically inert and/or clean and/or sterile and/or non-stick surface. Optionally, during storage, for example on a rolled up portion 821b of patch 820, protector 822 covers skin attachment surface 852 of active zone 856a of patch 820. For example, roller 816a may peel and/or place patch 820 from and/or to the skin on a separation line 876a. Optionally, separation line 876a is the line of contact. For example at separation line 876a, patch 820 is sandwiched between roller 816a and skin 811.

FIG. 8B is a perspective side view of a patch control system having a roller 816b which optionally keeps tension on the patch and/or stores the patch and a separate guide 895 which optionally guides a separation line 876b in accordance with an embodiment of the current invention. In some embodiments, guide 895 is supported on supports 897.

FIG. 8C is a perspective side view of a roller 816a which optionally guides a separation line 876c, pulls a patch 820 and/or stores patch 820 in accordance with an embodiment of the present invention. In some embodiments, patch 820 will deform skin 811, for example by pulling skin 811 into a mound 898 while disengaging patch 820. In some embodiments, the deformation of skin 811 may affect the peeling angle of patch 820. For example by having a smaller guide the effect of mounding of the skin on the angle of peeling may be greater. For example the angle of peeling may be decreased by more mounding of the skin (for example due to a sticker adhesive) and/or the angle of peeling may be decreased by using a larger guide (for example a roller with a larger diameter). The stickiness of the patch, size of the guide and/or direction of pulling may be adjusted for example to reduce discomfort when peeling a patch.

In some embodiments of the present invention, a roller optionally places a patch on skin and/or pulls a patch from the skin and/or pulls a patch away from a jig and/or stores a patch in accordance with an embodiment of the present invention. In some embodiments, patch 820 is stored by rolling up onto a roller 816. Optionally, roller 816 engages a portion 821a of patch 820 to a subject by unrolling portion 821a of the patch along a separation line 876 onto a skin 811 of the subject. For example, in the view of FIG. 8C, roller 816 rolls leftward to engage and/or unroll patch 820 onto skin 811. Optionally, roller 816 disengages the patch 820 from a subject for example by pulling and/or peeling the leading edge of patch 820 from skin 811. For example, in the view of FIG. 8C, roller 816 rolls rightward to roll up and/or disengage patch 820 from skin 811.

In some embodiments, the diameter of a rolled up patch 820 may increase as more patch 820 is rolled up. For example, while the patch is fully engaged with the skin of a user and/or before the patch starts being rolled up, the total diameter 884b of the roll may be diameter 884a of roller 816. As the patch is rolled up, the roll diameter 884b may increase. For example, the roller diameter 884a may start at between 2 to 4 mm and/or between 4 to 8 mm and/or between 8 to 16 mm. In some embodiments the roll may grow for example to a roll diameter 884b of between 10 to 20 mm and/or between 20 to 40 mm as the patch is loaded onto roller 816. In some embodiments, the distance radius of the roll changes along the circumference of the roll. In some embodiments, the changes in the radius may be abrupt. For example, the number of layers on roller 816 may change at the section 823 where the lead end of patch 820 contacts roller 816. The radius of the roll may increase sharply at section 823. Optionally the radius of the roll remains more or less constant over portions of the roll separated from section 823. For example section 823 may cover an arc ranging between 0 to 1 degrees and/or between 1 to 2 degrees and/or between 2 to 4 degrees and/or between 4 to 8 degrees and/or between 8 to 16 degrees and/or between 16 to 32 degrees.

In some embodiments, patch 820 includes an active zone 856a and/or an inactive zone 856b. Optionally, active zone 856a may have an active surface on a ventral face. For example, am inactive zone 856b may be on the trailing section of patch 820. Optionally, when patch 820 is fully rolled up onto roller 816, only a trailing section including inactive zone 856b is in contact with skin 811 and/or active zone 856a is not in contact with the skin. Optionally, when active zone 856a is not in contact with the skin, no treatment occurs. Alternatively or additionally, different zones of a patch may include different drugs and or different dosages. For example, zone 856a may include a first drug that is applied to skin 811 from the beginning of a treatment and zone 856b may have a different drug which is applied to the skin later in the treatment.

In some embodiments, patch 820 includes a skin attachment surface 852 on a ventral side thereof. Optionally, a dorsal side of the patch is covered by a protector 822. For example, protector 822 may include a liner. Optionally protector 822 includes a chemically inert and/or clean and/or sterile and/or non-stick surface. Optionally, during storage, for example on a rolled up portion 821b of patch 820, protector 822 covers skin attachment surface 852 and/or active zone 856a of patch 820. For example, roller 816 may peel and/or place patch 820 from and/or to the skin on a separation line 876. Optionally, separation line 876 is the line of contact. For example at separation line 876, patch 820 is sandwiched between roller 816 and skin 811.

Exemplary Stationary Reversible Patch Roller System

Figure 9A:
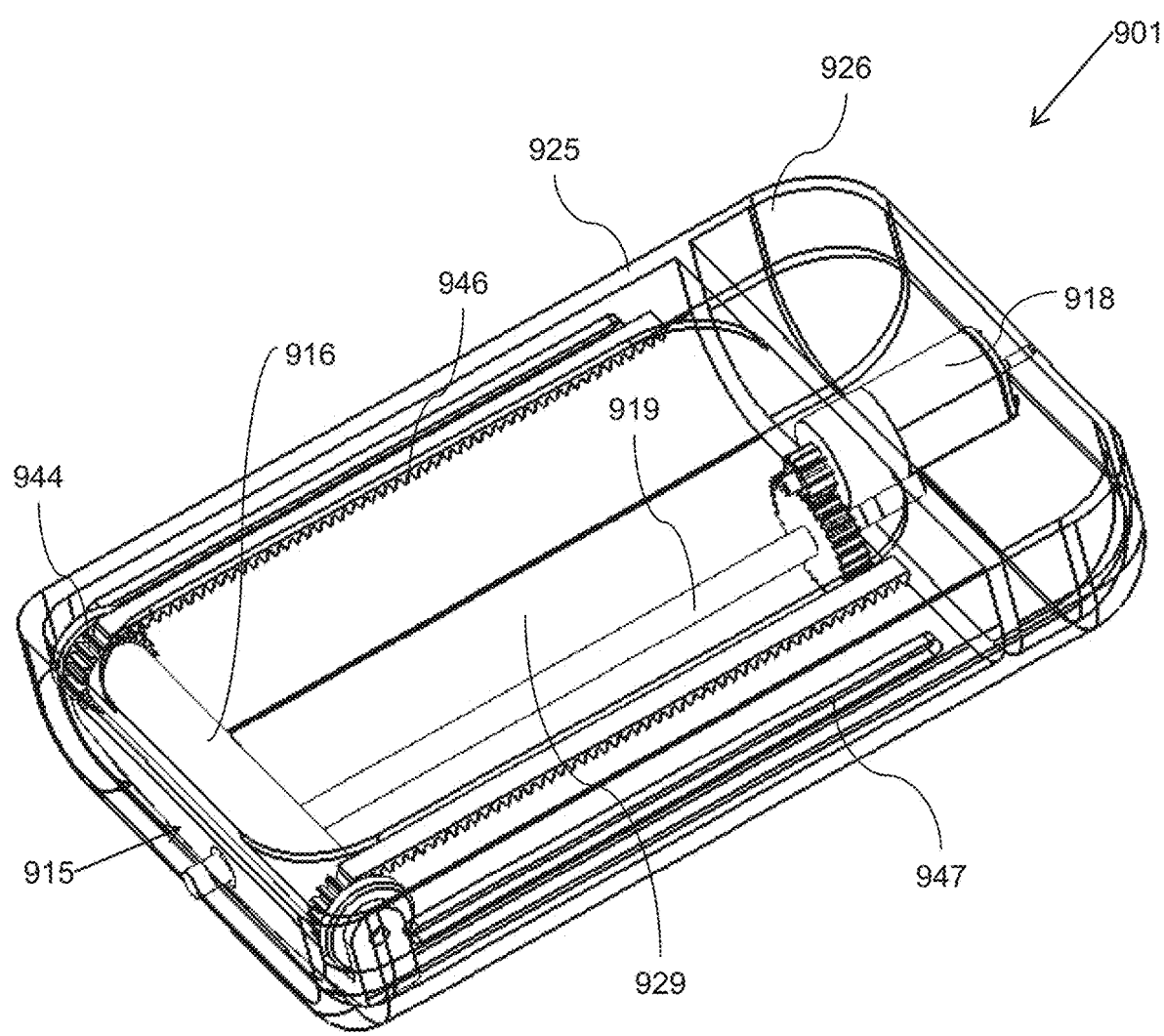
FIG. 9A is a perspective view of a ventral side of a patch control device with a roller in accordance with an embodiment of the present invention.

FIG. 9A is a perspective view of a ventral side of an exemplary patch control device 901 in accordance with an embodiment of the present invention. Optionally device 901 reversibly engages and/or disengages portions of a patch. Optionally device 901 stores disengaged portions of the patch. In some embodiments, device 901 includes a roller 916. Optionally roller 916 rolls backwards and/or forward inside a frame 926. For example, when roller 916 rolls in one direction it rolls up and/or disengages a portion of a patch. For example, when roller 916 rolls in an opposite direction it unrolls and/or engages a portion of the patch. Optionally, a stored portion may be protected by a liner and/or stored on a roller 916.

In some embodiments, frame 926 includes a shell surrounding roller 916. Optionally frame 926 includes an attachment surface 925 on a base of the ventral side of frame 926. Optionally attachment surface 925 surrounds an opening 929. For example, attachment surface 925 fully surrounds opening 929. Alternatively or additionally an attachment surface may only partially surround opening 929. For example, when the device 901 is placed onto a subject, attachment surface 925 lies against the skin of the subject. Optionally when a patch is in an engaged state, an active surface of the patch is exposed to and/or contacts the skin of a subject through opening 929. Optionally in a disengaged state, the active surface may be rolled up on roller 916 and does not contact the skin of the user.

In some embodiments, frame 926 includes one or more tracks. For example, frame 926 includes a sliding guide track 947 and/or a friction track 946. Optionally a driver 918 (for example including a DC motor) drives a transmission 919 to pull or push a roller assembly 915 longitudinally along guide track 947. For example transmission 919 may include a threaded shaft which is engaged to a thread in assembly 915. For example rotating transmission 919 in one direction pulls assembly 915 longitudinally along track 947 towards driver 918. For example rotating transmission 919 in an opposite direction pushes assembly 915 longitudinally along track 947 away from driver 918.

In some embodiments, as assembly 915 moves longitudinally along guide track 947, roller 916 rotates to roll up and/or unroll a patch. Optionally as assembly 915 moves in a first direction roller 916 rolls up and/or disengages a patch. Optionally as assembly 915 moves in an opposite direction roller 916 unrolls and/or engages the patch. For example, as assembly 915 moves longitudinally, a friction contact surface 944 of roller 916 rolls along friction track 946, causing roller 916 to rotate. For example, friction track 946 may include teeth that engage to teeth of friction contact surface 944 which optionally includes a gear.

In some embodiments a synchronizer may synchronize the rate of engaging of patch 920 with the rate of movement roller 916. For example the teeth of track 946 may be differentially spaced. For example the spacing of the teeth may be configured to synchronize rolling of roller 916 with its linear movement. Alternatively or additionally a controller may separately control the linear and rotational movements (for example with separate drivers).

Figure 9B:
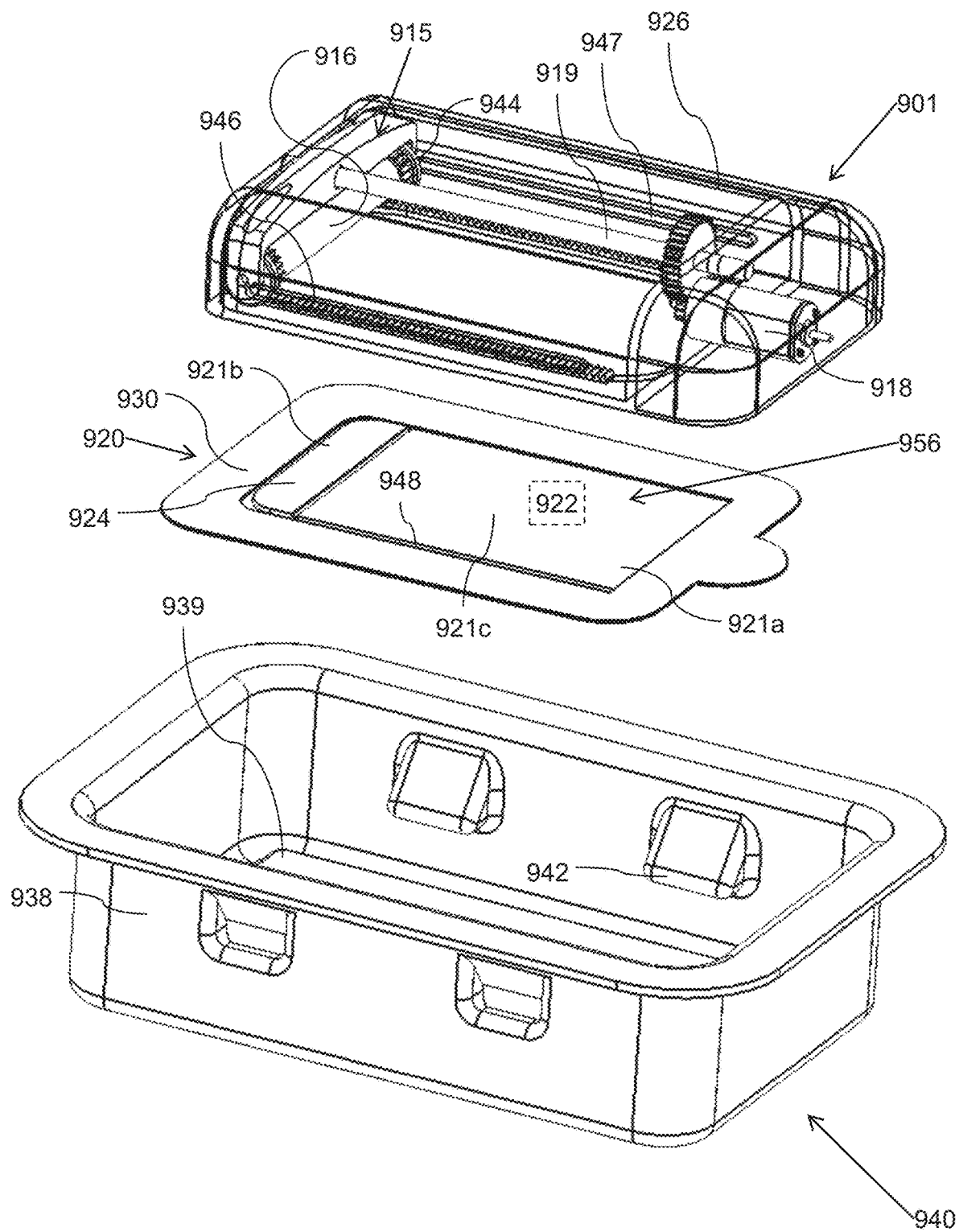
FIG. 9B is a perspective view of a dorsal side of a patch control system with a roller in accordance with an embodiment of the present invention.

FIG. 9B is a perspective view of a dorsal side of a patch control system in accordance with an embodiment of the present invention. Optionally, a patch control system reversibly engages and/or disengages portions of a patch. Optionally, a patch control system may stores disengaged portions of the patch and/or protects stored portions, for example by a liner. For example the portions are stored on a roller. In some embodiments, a patch control system may include a patch control device 901 and/or an optionally custom patch 920 and/or an alignment jig 940.

In some embodiments, patch 920 includes a stationary portion 930. Optionally, stationary portion 930 may include adhesive of both sides. For example adhesive on the dorsal side may adhere stationary portion 930 to attachment surface 925 of frame 926. For example, adhesive on the ventral side of stationary portion 930 may adhere to stationary portion 930 and/or attachment surface 925 of frame 926 to the skin of a subject. For example, when device 901 is positioned on a subject, stationary portion 930 may be immobile and/or sandwiched between contact area 925 of frame 926 and the skin of the subject. In some embodiments, stationary portion 930 surrounds a disengageable portion 956 of the patch (the disengageable portion 956 optionally includes a leading portion 921b, a trailing portion 921a and/or a mid portion 921c.

In some embodiments, connections between patch 920 and device 901 are made by a single simple movement. For example, device 901 has all of its connections to patch 920 exposed on one side (e.g. the ventral side of device 901 connects to the dorsal side of patch 920). For example, a contact zone of roller 916 which contacts adhesive 924 of the leading mobile end of mobile portion 956 and/or an attachment surface 925 of device 901 which connects stationary portion 930 of patch are all exposed on a ventral face of device 901. For example by pushing device 901 downward onto the dorsal surface of patch 922 the patch is loaded to device 901. Optionally all of the connection surface lie on a place such that device 901 connects to patch 920 while patch 920 is lying flat on a surface. Alternatively or additionally an alignment jig 940 has a base with contours that position patch 920 properly to connect to each part of device 901. For example, the contact zone of roller 916 may be recessed with respect to attachment surface 925. Optionally the base of alignment jig 940 holds the free leading portion 921b extended upward to contact the contact roller 916 when device 901 is lowered into place onto alignment jig 940. Optionally, after connection, a mobile disengageable portion 956 may be wound to roller 916 (e.g. into a disengaged state) before attaching device 901 to a subject. Alternatively or additionally, device 901 may be attached to a subject in an engaged state.

In some embodiments, stationary portion 930 may partially surround disengageable portion 956. For example, stationary portion 930 may just extend from a trailing portion 921a of disengageable portion 956 of patch 920. Alternatively or additionally a patch may be entirely wound onto a roller without a frame contact area.

In some embodiments, a leading portion 921b and/or a mid portion 921c of disengageable portion 956 is optionally separated from frame contact area by a discontinuity, for example a cut out 948. For example, cut out 948 permits leading portion 921b and or central portion 921c to roll up onto roller 916 while stationary portion 930 remains stationary with respect to the skin of the subject, for example on or close to the skin of the subject. Alternatively or additionally, cut out 948 permits leading portion 921b and or central portion 921c to roll up onto roller 916 while stationary portion 930 remains stationary with respect to frame 926, for example sandwiched between attachment surface 925 of frame 926 and/or the skin of the subject.

In some embodiments, patch 920 may be sold as a whole conventional patch without a discontinuity. For example the discontinuity is optionally cut into the patch after production and/or sale. Optionally, a device and/or die may be supplied to cut a discontinuity. For example, the cut out device may be a separate device, and/or may be including in packaging of a patch and/or of a dosage control device. For example alignment jig 940 may include a die and/or blade to cut the discontinuity. For example a convention patch may be modified by cutting a discontinuity. Optionally the discontinuity will be in a non-active area. For example cutting a discontinuity into a patch may not compromise an active area and/or a drug reservoir and/or a release membrane.

In some embodiments, leading portion 921b of disengageable portion 956 of patch 920 includes adhesive 924 on its dorsal side. Adhesive 924 optionally connects leading portion 921b to roller 916. Alternatively or additionally, roller 916 may be coated with adhesive. Alternatively or additionally, roller 916 and/or leading portion 921b may include a magnet and/or a clip and/or a hook and/or a slit to for example for connecting the free portion of the patch to the roller.

In some embodiments, a protector may protect an active zone and/or a skin attachment surface of a patch during storage. For example, a flexible backing including for example a liner 922 covers mid section 921c of stationary portion 930. When patch 920 is stored (for example by rolling up onto roller 916 such that disengageable portion 956 is wound around roller 916) the skin attachment surface of disengageable portion 956 is optionally covered by liner 922. Optionally liner 922 is made of a chemically inert and/or non-stick and/or non-reactive substance that will protect the drug in disengageable portion 956. Optionally liner 922 is made of a non-stick substance that will protect the adhesive on the skin contact area of disengageable portion 956 of patch 920. For example liner 922 may be made of a non-reactive coating over a substrate. For example a non-reactive coating may include Polyethylene and/or the substrate may include a metal foil (e.g. aluminum) with a thickness between 0.05 and 0.2 mm. Alternatively or additionally, a substrate may include paper and/or plastic.

In some embodiments, a patch control system may include an alignment jig 940. For example alignment jig 940 may include a cavity of a blister package for patch 920 and/or device 901. For example, device 901 and/or patch 920 may be packed inside of device 940 and sealed with a backing for shipping and distribution. Device 940 optionally includes interference elements 942. For example interference elements may be used to snap device 901 into device 940. For example elements 942 may hold the ventral face of device 901 firmly against base 939 of device 940. Optionally device 940 may be used to mount patch 920 onto device 901. Alternatively or additionally, alignment may be facilitated with printed signs, pins, indentations and/or protrusions for the patch and/or device etc. Alternatively or additionally, device 901 may be preloaded with patch 920. Alternatively or additionally, patch 920 may be mounted to device 901 without an alignment jig. Alternatively or additionally, device 901 may be used with a standard patch and an interface (for example patch 1420 and/or adapter 1401 as illustrated in FIG. 14). Alternatively or additionally other options for patch geometry may be used with device 901.

In some embodiments, positioning the patch and the control device onto the alignment jig will connect the patch to the control device. For example, once patch 920 is lying on base 939 with connector 924 exposed, device 901 is placed onto alignment jig 940 with attachment surface 925 facing towards the exposed connector 924 on patch 920. Optionally device 901 is pushed past interference elements 942 which snap down on device 901 securely pushing attachment surface 925 against stationary portion 930 and/or pushing roller 916 against connector 924. Optionally alignment jig 940 is shaped such that patch 920 and/or device 901 are pushed into proper alignment when they are positioned on device 940. For example, a cavity of device 940 may have beveled walls 938 leading to a tight fitting compartment such that putting a patch and/or control device into the cavity pushes them into mutual alignment.

In some embodiments patch control device 901 may include a window. For example the window may be positioned for viewing a status of an engagement of a patch.

In some embodiments, base 939 may include a protrusion. For example, the protrusion may include contact between the patch and a recessed surface of device 901. For example, the protrusion may include a surface that fits the curved surface of roller 916.

Optionally a track 946 and/or guide 947 may not be oriented parallel to attachment surface 925. For example, track 946 and/or guide 947 may be configured to keep a constant distance between an edge of a patched rolled onto roller 916 and the skin of a user. For example, in a position where a large portion of the patch is rolled onto the roller and/or the radius of the roll is large, track 946 and/or guide 947 may be further from skin contact surface 925. For example, in a position where a smaller portion of the patch is rolled onto the roller and/or the radius of the roll is smaller, track 946 and/or guide 947 may be closer to skin contact surface 925.

Exemplary Patch

Figure 10:
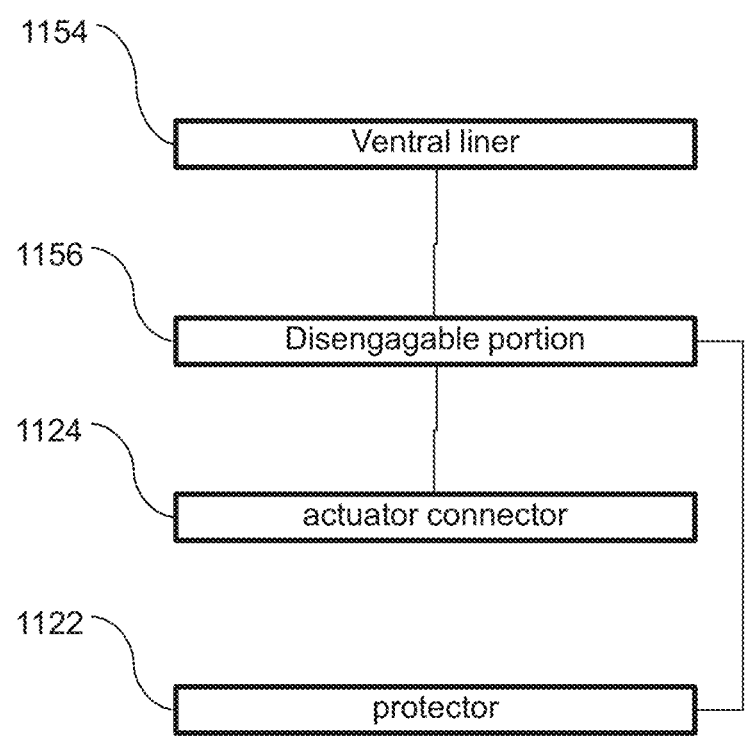
FIG. 10 is a block diagram illustration of a patch in accordance with some embodiments of the current invention.

FIG. 10 is a block diagram illustration of a simple patch in accordance with some embodiments of the current invention. Optionally, a patch may include a disengageable portion 1156. Optionally, the entire patch may be disengageable from the subject. In some embodiments, the patch includes an active surface. For example the active surface may be on a ventral face of the patch. Optionally the disengageable portion includes a connector 1124 for connecting to an actuator of a control device. The patch optionally includes a protector 1122. For example protector 1122 may protect the active surface during storage by a patch control device. Optionally the patch includes a ventral liner 1154. For example, ventral liner 1154 may protect an active region of the patch before use. For example, the ventral liner may be removed by a user prior to use of the patch. Optionally a patch may include a dorsal liner. For example connector 1124 may include an adhesive surface which is optionally protected by a dorsal liner.

In some embodiments an active surface of a patch may include a drug (for example a medicine patch). Alternatively or additionally the active surface may include an adhesive (for example a medicine patch and/or an interface for a medicine patch).

In some embodiments, connector 1124 may be on a leading edge of the patch and/or on a dorsal face of the patch for example on a dorsal face of a leading portion of the patch.

Figure 11:
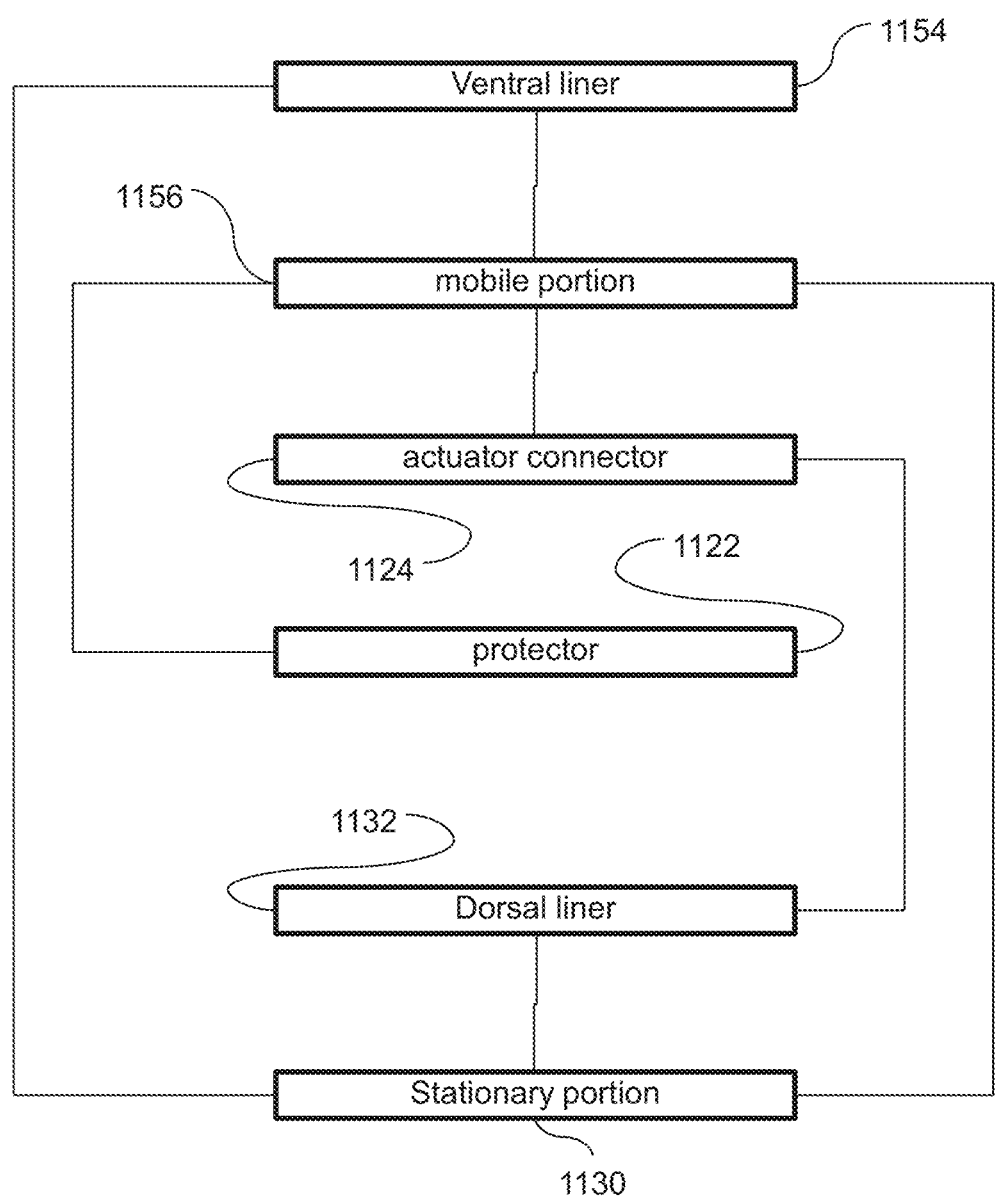
FIG. 11 is a block diagram illustration of a two part patch in accordance with some embodiments of the current invention.

FIG. 11 is a block diagram illustration of a two part patch in accordance with some embodiments of the current invention. In some embodiments, a patch may include a stationary portion 1130 and/or a disengageable portion 1156. For example the disengageable portion 1156 is configured to be connected by a connector 1124 to an actuator of a patch control device. Optionally stationary portion 1130 is configured to be connected to a stationary portion (for example a frame) of the patch control device. Optionally the stationary portion may include an adhesive on two sides and/or be connected to a dorsal liner 1132 and/or a ventral liner 1154. Dorsal liner 1154 optionally protects actuator connector 1124 of the disengageable portion 1156 of the patch.

Figure 12:
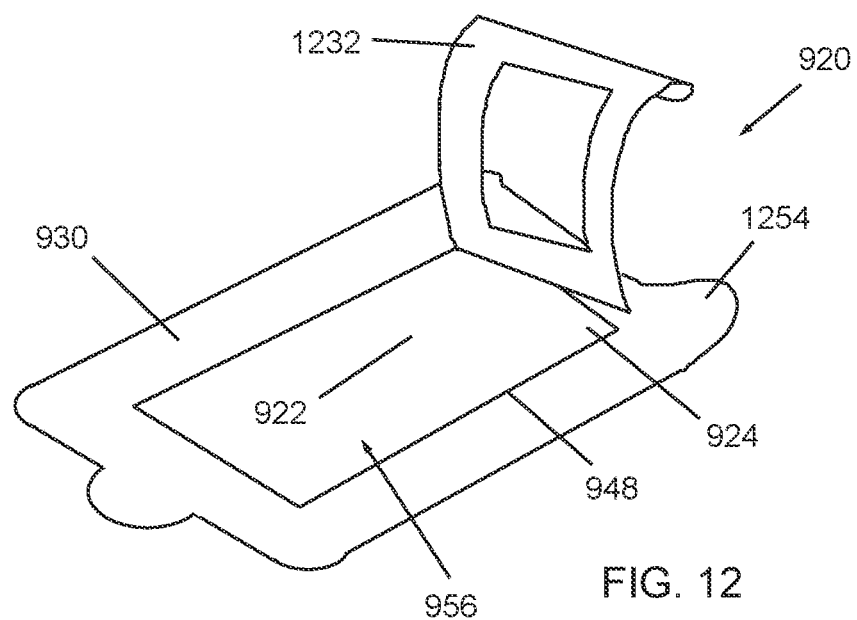
FIG. 12 is a perspective illustration of a dorsal side of a patch in accordance with an embodiment of the present invention.

FIG. 12 is a perspective illustration of a dorsal side of patch 920 in accordance with an embodiment of the present invention. A dorsal liner 1232 is illustrated partially removed from patch 920. Patch 920 is supplied to a user with, dorsal liner covering an adhesive dorsal surface of stationary portion 930 and/or an adhesive connector 924 for connecting a leading portion of disengageable portion 956 of patch 920 to an actuator of a patch control device. Optionally liner 1232 does not cover protector 922. Alternatively or additional, a dorsal liner may cover a protector for example as illustrated in FIG. 14 where a dorsal liner 1432 covers an entire dorsal face including a protector 922 of a interface patch 1401. In some embodiments, a ventral liner 1453 covers a ventral face of a patch. For example ventral liner 1453 may be peeled off before the patch is placed on the skin of a subject.

Figure 13:
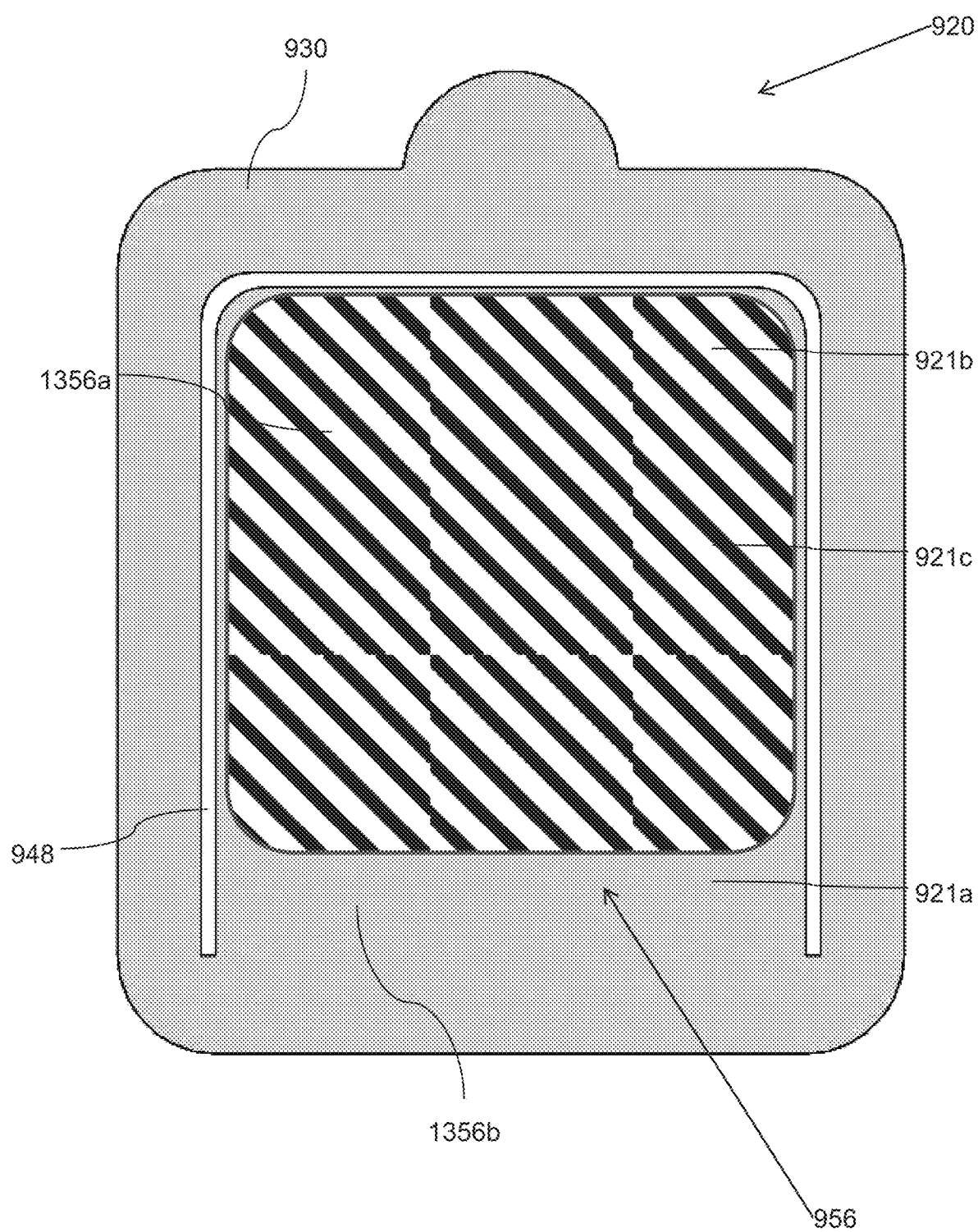
FIG. 13 is a perspective illustration of a ventral side of a patch in accordance with an embodiment of the present invention.

FIG. 13 is a ventral view of a patch in accordance with an embodiment of the current invention. In some embodiments a ventral face of patch 920 includes an active surface 1356a on a disengageable portion 956. For example active surface 1356a may include a drug that is absorbed by the skin of a subject when zone 1356a contacts the skin. Optionally a patch control device (for example device 901) controls the magnitude of the surface area of zone 1356a exposed to the skin and/or the rate of absorption of the drug to the subject. For example, disengaging part of zone 1356a reduces the dosage and/or rate of application of the drug. For example, engaging part of zone 1356a increases the dosage and/or rate of application of the drug.

In some embodiment trailing portion 921a of portion 956 may be included in an inactive surface 1356b. For example, misalignment of a device and/or a patch and/or irregularities of the surface of the skin may cause uncertainty in the state of engagement and/or disengagement of the trailing portion 921a and/or the outermost layer of the rolled up patch. Including portion 921a in inactive portion 1356b may decrease the uncertainty of dosage and/or avoid a danger that medicine will continue to be absorbed when patch 920 is supposed to be fully disengaged.

Exemplary Interface for Patch

FIG. 14 is a schematic illustration of an interface for connecting a patch to a patch control device in accordance with an embodiment of the current invention. In some embodiments, an interface may be used to facilitate loading a patch to a patch control device. Optionally an interface, for example, adapter 1401 may be used to facilitate loading a conventional medicine patch (for example patch 1420) to a control device, for example device 901. For example, a dorsal side of adapter 1401 may be configured for loading to device 901 and/or a ventral side of the patch may be configured for attaching to a convention patch.

In some embodiment, a ventral side of adapter 1401 may include a connector 924 and/or a protector 922. Optionally the ventral face of adapter 1401 is covered by a liner 1453 prior to use. Optionally adapter 1401 includes a stationary portion 930 which surrounds and/or partially surround and/or is partially attached to a disengageable portion 956. For example a cut out 948 may separate between some parts of the stationary portion 930 and disengageable portion 956.

In some embodiments, the ventral face of disengageable portion 956 of adapter 1401 includes a substrate and/or an adhesive. Optionally the dorsal face of patch 1420 is adhered to the ventral face of disengageable portion 956 of adapter 1401. The patch 1420 becomes the active region of disengageable portion 956. For example by engaging and/or disengaging the ventral side of portion 956 to the skin of a subject, patch 1420 is engaged and/or disengaged. The combined patch 1420 and adapter 1401 are optionally loaded to device 901 according to the methods described for example in FIGS. 7A-7B. In some embodiments, a skin contact area and/or an active face and/or ventral face and/or an active surface of patch 1420 will be protected by a liner 1454 prior to use.

In some embodiments, the adhesive area on the ventral said of the adapter 1401 will be larger than the dorsal side of patch 1420. Optionally the adhesive on the ventral side of patch 1401 may be formulated to stick fast to the dorsal face of patch 1420 and/or to be biocompatible and/or to be easily removed from skin. Alternatively or additionally, patch 1420 may be attached to adapter 1401 (for example to the ventral face of portion 956) by ultrasonic welding and/or heat and/or by means of a vacuum. For example, the ventral face of portion 956 may be a substrate that can include attached to patch 1420.

In some embodiments, an adapter and/or an alignment jig will be shaped and sized for a particular patch. For example, an area of adhesive on a ventral side of the adapter may fit the patch. For example the adhesive area may be within 1 mm of the dimensions of the dorsal face of the patch and/or within between 1 and 5 mm and/or between 5 and 20 mm. Optionally an alignment jig may facilitate fitting the convention patch to the adaptor and/or the patch control device and/or fitting the adaptor to the patch control device. Optionally, attaching patch 1420 to adapter 1401 and/or device 901 does not change an active surface of and/or drug administration property of patch 1420.

Alternative Stationary Reversible Patch Roller System

Figure 15A:
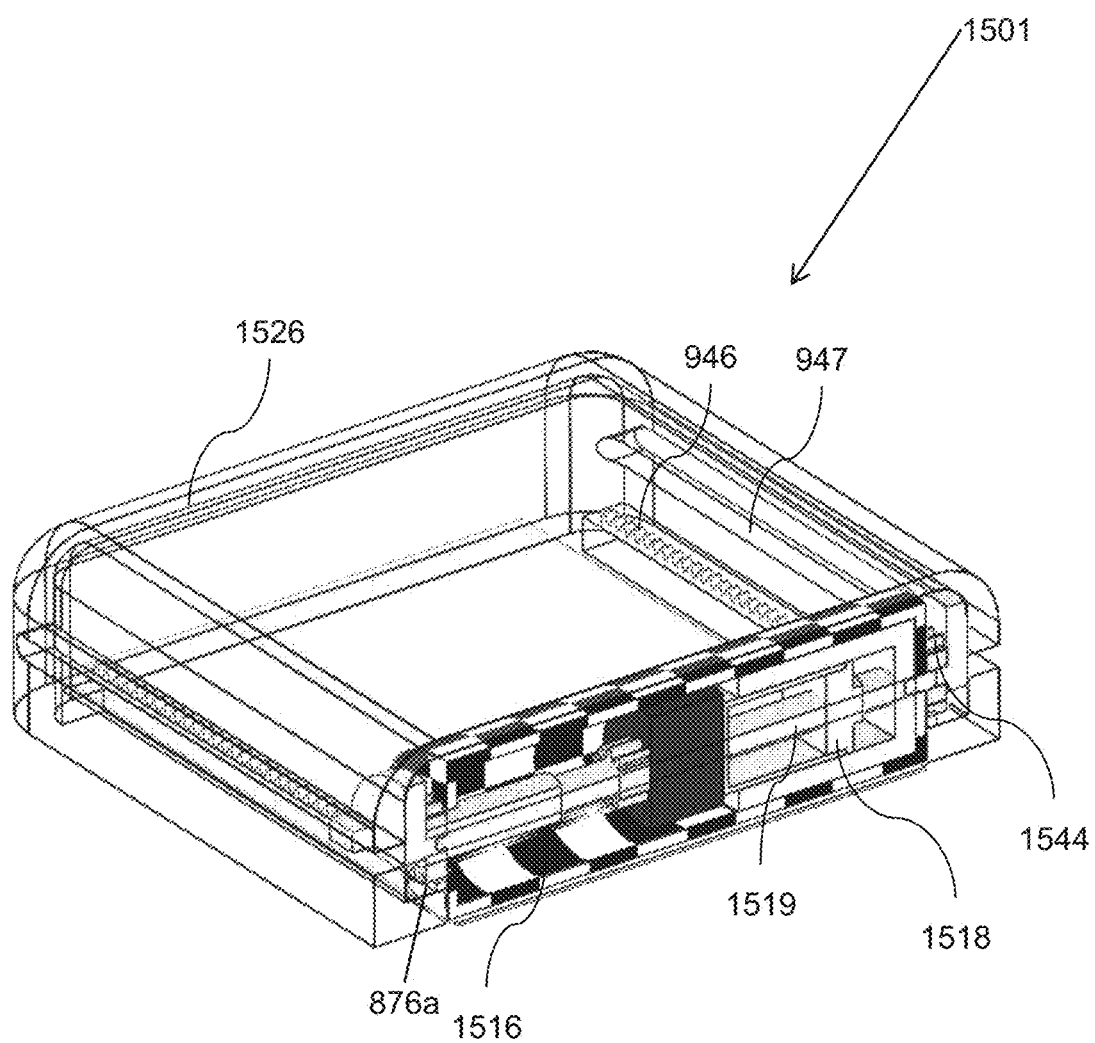
FIGS. 15A-15C are a perspective views a roller patch control device in accordance with an embodiment of the present invention.
Figure 15B:
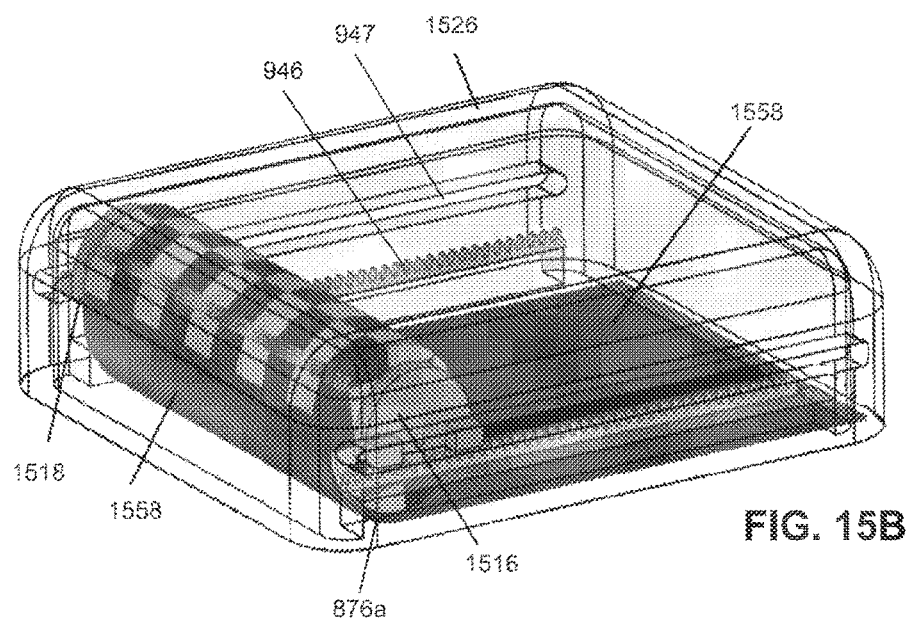
Figure 15C:
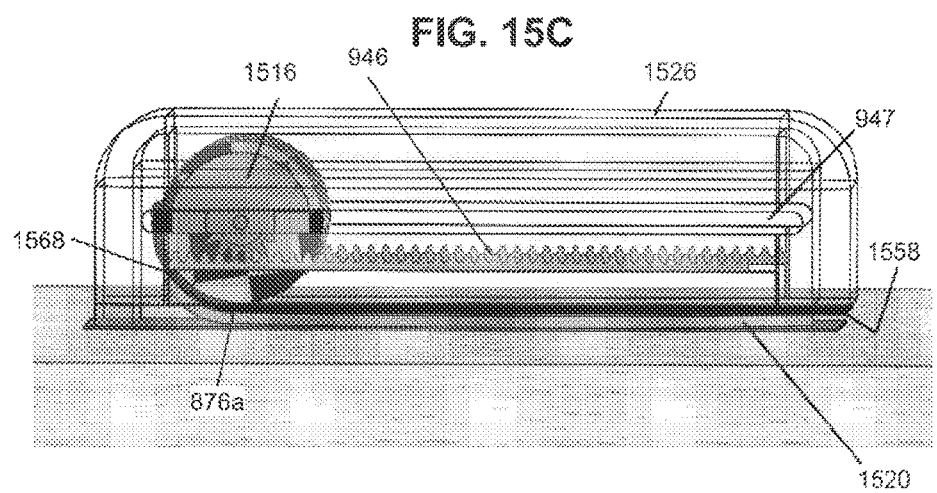

FIGS. 15A-15C are perspective views of a direct drive patch control device in accordance with an embodiment of the present invention. The control device optionally reversibly engages and/or disengages portions of a patch. Optionally disengaged portions are stored on a roller.

In some embodiments, a patch control device 1501 includes a roller 1516 that rotates and slides along a track 947 inside a frame 1526 to engage and/or disengage a medicine patch. Optionally in the disengaged state the patch is stored wound around roller 916.

In some embodiments, roller 1516 is driven by direct drive driver 1518. Driver 1518 optionally rotates a transmission 1519 which rotates roller 1516 and friction wheels 1544. Friction wheels 1544 roll along track while roller 1516 rotates rolling up and/or rolling out the patch. In some embodiments, device 1501 is loaded uses the same patch and/or is loaded as described above with respect to device 901.

In some embodiments, roller 1516 may rotate and/or move linearly along track 947. For example, propulsion may be provided by a friction wheel 1544 (e.g. a gear) rolling along a friction track 946 (e.g., a toothed track) formed in housing 1526. Driver 1518 optionally turns roller 1516. For example driver 1518 may be located inside the roller 1516. This configuration may save space over an external driver.

Optionally, the rotating speed of roller 1516 is adapted to synchronize the speed of the surface of the substrate to the linear rate of uptake and/or release of the patch. For example as the diameter of the roll grows (e.g. with increasing numbers of layers of substrate and/or patch over roller 1516) the rotation rate may be reduced with respect to the rate of linear movement of roller 1516. Optionally a synchronizer may synchronize the rate of engaging of uptake or output of substrate 1558 with the rate of movement roller 1516 and/or separation line 876a. For example distance between teeth in the track 946 may be adjusted synchronize linear motion and rotation of roller 1516. For example in FIG. 15B, where the diameter of the roll increases as roller 1516 moves rightward, the distance between the teeth in track 946 may get larger as one moves down the track from left to right and/or the ratio of rotation to linear movement is reduced as roller 1516 moves from left to right. In some embodiments, synchronizing with the roller linear and rotational velocity may to facilitate deployment of the patch with reduced wrinkle or skin pinching and/or hair pulling. Alternatively or additionally a controller may separately control the linear and rotational movements (for example with separate drivers). Alternatively or additionally, substrate 1558 may be biased outward. Optionally, the outward bias may push a patch 1520 toward the skin of a user and/or attach the patch to the skin of the user. For example, roller 1516 may unroll substrate 1558 faster than the linear movement of roller 1516. The extra length of substrate 1558 optionally causes substrate 1558 to bulge outward. For example the extra length may be between 0.01 mm to 0.1 mm and/or between 0.1 mm to 0.5 mm and/or between 0.5 mm to 1 mm and/or between 1 to 4 mm.

FIG. 15C illustrate an optional way of mounting a standard drug patch 1520 onto roller 1516. Optionally, the actuator (for example a puller and/or an applicator of device 1501) may include a substrate 1558. Substrate 1558 (for example an adhesive foil without the substance on the patch) is optionally connected to the roller 1516 and/or extends out from the roller 1516 over the bottom of housing 1526. In order to connect the patch 1520 to the roller, housing 1526 is optionally placed onto patch 1520, whereupon the patch 1520 sticks to substrate 1558. Optionally, an alignment device for example a jig may be used to align patch 1520 to substrate 1558. For example, roller 1516 may peel and/or place substrate 1558 to from and/or to the skin on a separation line 876a.

In some embodiments, once patch 1520 is attached to substrate 1558, a liner may be removed from the active face (e.g. the bottom face in FIG. 15C) of the patch 1520. The exposed patch 1520 and/or device 1501 are then placed on the skin in an engaged state. Alternatively or additionally, before placing device 1501 on the skin, driver 1518 may turn the roller 1516 to cause patch 1520 and/or substrate 1558 to wrap and/or roll around the roller 1518 into a disengaged and/or stored state. In some embodiments, a protective element (e.g. to protect a patch during storage) is a part of the control device. For example the back of substrate 1558 optionally serves as a liner and/or protective layer on the patch 1520 (e.g. the active surface thereof) during storage. Optionally, device 1501 is placed onto a subject in the disengaged state. Alternatively, instead of using driver 1518 to wind up patch 1520, housing 1526 may be moved across a surface (e.g., assembly table) to cause roller 1516 to turn and move in track 947. Optionally, a tongue 1568 is provided near the roller 1516 just before patch 1520 begins to wrap around the roller 1516. For example, tongue 1568 may catch and lift off any liner that was mounted on patch 1520, so that patch 1520 rolls up on roller 1516 without the liner.

In some embodiments a roller (for example roller 916 and/or roller 1516) may be driven by a pulley and/or a linear actuator and/or a spring drive.

In some embodiments patch control housing 1526 may include a window. For example the window may be positioned for viewing a status of an engagement of a patch.

Optionally a track 946 may not be oriented parallel to attachment surface. For example, track 946 may be configured to keep a constant distance between an edge of a patched rolled onto roller 1516 and the skin of a user. For example, in a position where a large portion of the patch is rolled onto the roller and/or the radius of the roll is large, track 946 may be further from skin contact surface. For example, in a position where a smaller portion of the patch is rolled onto the roller and/or the radius of the roll is smaller, track 946 may be closer to skin contact surface.

Engagement Controller of a Medicine Patch

Figure 16:
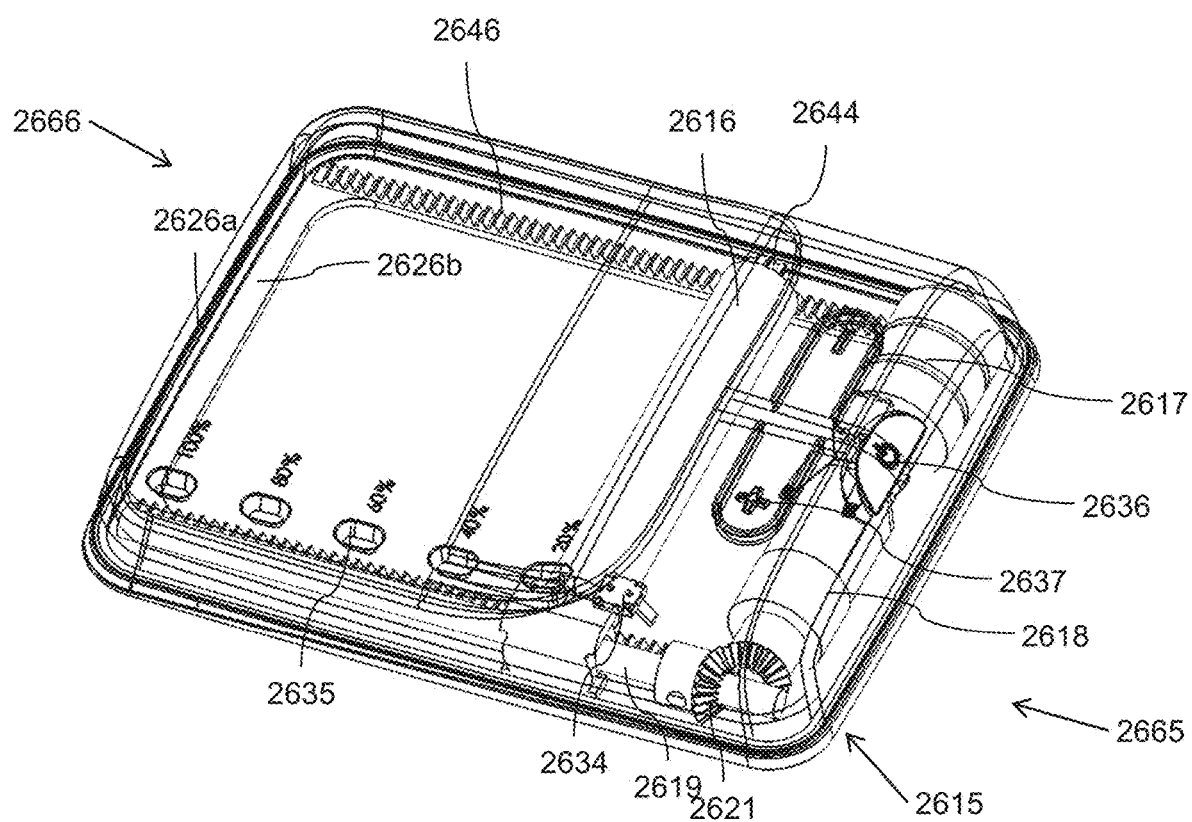
FIG. 16 is a top perspective view of a patch controller device in accordance with some embodiments of the present invention.

FIG. 16 is a top perspective view of a patch controller device in accordance with some embodiments of the present invention. In some embodiments, a patch control device may be designed to have a low profile. For example, the power source and/or energy source may be alongside each other and/or alongside the patch.

In some embodiments a drive mechanism is mounted along adjacent to a patch area of the device. Optionally, the side including the drive system is taller than other parts of the device. For example, a rear portion 2665 of a device may house a drive system including a motor 2618 and/or energy source 2617 (for example batteries) and/or a transmission 2615 (for example including a pair of bevel gears 2621). The drive housing of the rear section 2665 of the device may have a higher profile that a forward section 2666 and/or mid-section of the device. Optionally, the drive housing of the device is located adjacent to (for example behind) a patch area (where in the patch is stored and/or deployed). For example, the patch area may include the central part of a mid-section and front section 2666 of the device. In some embodiments, locating the drive mechanism adjacent to the patch may facilitate reducing the profile of the device for example compared a device where the drive mechanism overlies the patch.

In some embodiments the height of the device (for example the average distance from a skin attachment surface to an top surface of the device) may range for example between 5 to 10 mm and/or between 10 to 20 mm and/or between 20 to 50 mm. In some embodiments the ratio of height of the device between a shorter point (for example the front end and/or the end which doesn't include the drive system) and a taller portion (for example the rear end and/or the end including the drive system) may range between 1 to 0.95 and/or 0.95 to 0.75 and/or between 0.75 to 0.5 and/or less than 0.5. In some embodiments the length of the device (e.g. from front to back) may range between 20 to 40 mm and/or between 40 to 80 mm and/or between 80 to 120 mm. In some embodiments the width of the device may range between 10 to 20 mm and/or between 20 to 40 mm and/or between 40 to 80 mm and/or between 80 to 120 mm.

Figure 17:
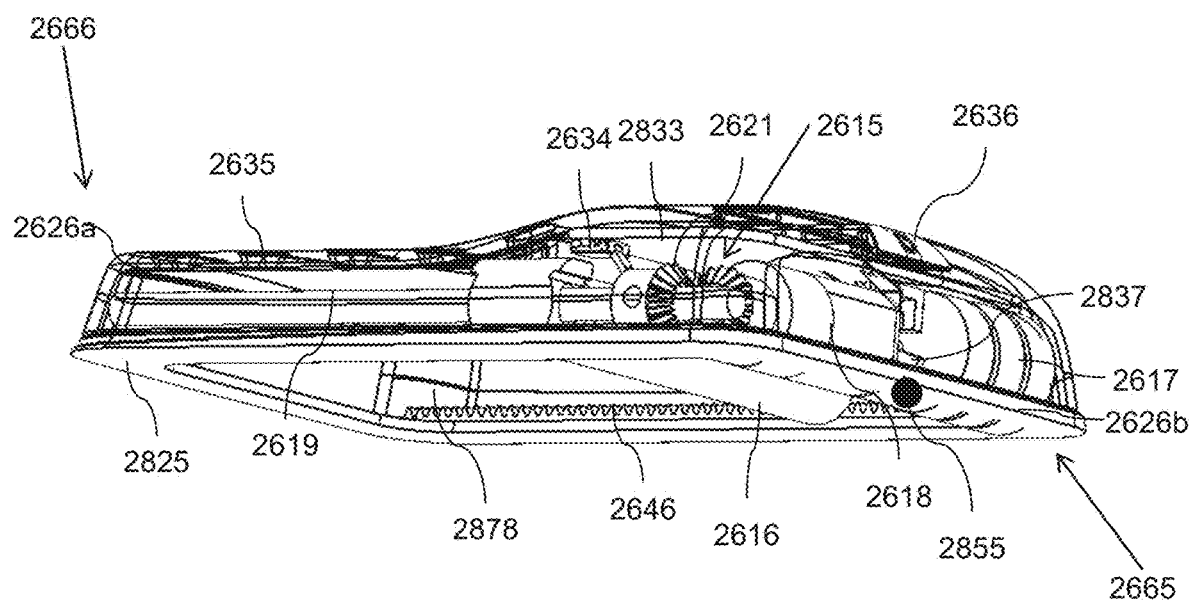
FIG. 17 is a side perspective view of a medicine patch controller device in accordance with some embodiments of the present invention.

In some embodiments, the drive mechanism passes power to a roller 2616. For example, transmission 2615 may drive a power transmitting member, for example including a drive shaft 2619. Optionally, the power transmitting member may be located adjacent to a patch area. For example, drive shaft 2619 is located on the left side of the patch area. For example, a patch area 2878, as illustrated in FIG. 17, is the area wherein the patch contacts the skin of a user when it is spread out in the engaged state. For example, the patch area 2878 includes an opening of the base of the device. In some embodiments, locating the power transmitting member adjacent to the patch and or the patch area may facilitate reducing the profile of the device for example compared a device where the power transmitting member overlies the patch.

In some embodiments, drive shaft 2619 rotates roller 2616. Rotating roller 2616 optionally causes a roller gear 2644 to drive roller along guide (for example a track 2646). For example, as roller 2616 rolls towards the rear section 2665 along track 2646 roller 2616 unrolls a patch and/or lays the patch onto the skin of a user and/or engages the patch to the skin. For example, as roller 2616 rolls towards the front section 2666 along track 2646 roller 2616 peels a patch from the skin of the user and/or disengages the patch from the skin and/or rolls the patch onto roller 2616. Alternatively or additionally, a patch may rolled up as the roller moves toward rear section 2665 and/or unrolled as the roller moves toward front section 2666. For example, the height of front section 2666 may reduced where the diameter of the roll is small and/or the height of the rear section 2665 may large where there needs to be space for the drive mechanism and/or where the patch roll diameter is larger.

In some embodiments, a device may track the status of a patch. For example the patch may be loaded to the device in an open (e.g. unrolled and/or deployed) state. When the device rolls up the patch (partially or fully) it may tracking progress of roller 2616. For example, a controller of the device may count revolutions of a part of the drive mechanism and/or a power transmission mechanism and/or roller 2616 and/or compute a level of deployment. Optionally, the device includes a sensor, which senses a deployment state of the patch. For example, a microswitch may sense when roller 2616 is in the fully rearward position and/or when the patch is fully deployed. For example, if the controller loses track of the position of the patch (for example due to a power loss), when the controller returns to operation it may unroll the patch until it is completely deployed and/or until microswitch registers that the patch is fully deployed and then the controller may reset and/or begin tracking. Alternatively or additionally, a microswitch may be supplied that registers when the patch is fully rolled onto roller 2616. Alternatively or additionally, other sensors may be used to detect a state of a patch, for example an optical sensor and/or a variable tension sensor (for example connected to an elastic member whose tension is dependent on the position of roller 2616). In some embodiments, a patch controller may include an alarm and/or a safety retract mechanism to alert a user and/or roll up a patch ceasing drug delivery when a fault and/or power outage occurs.

In some embodiments, a patch controller device may be for single use. For example the device may be packaged and/or sold with a patch already installed. Optionally, a single use device may use disposable parts, for example disposable batteries as an energy source. Alternatively or additionally, a patch control device may be multi-use. For example, the device may include replaceable batteries and/or rechargeable batteries and/or a charger port.

In some embodiments, a patch controller includes an integral user interface. For example, a patch controller may include an on off switch, for example a button 2636 and/or a toggle switch and/or a sliding switch (for example switch 3036 of FIG. 19). For example, a patch controller may include a switch to increase and/or decrease deployment of a patch. For example, rocker switch 2637 includes a plus side. Pushing plus side causes a patch to deploy and/or unroll from roller 2616, increasing a dosage rate. For example, rocker switch 2637 includes a minus side. Pushing the minus side optionally causes a patch to return and/or roll onto roller 2616, decreasing a dosage rate.

In some embodiments, a device (for example a user interface thereof) will display a status of a patch. For example a device may include one or more holes 2635 through which a user can see a position of roller 2616 and/or how much of a patch is deployed. Optionally markers on holes 2635 indicate a portion of a patch that is deployed. Alternatively or additionally holes 2635 may be marked with a rate of dosage, for example when a device is preloaded with a patch and/or designed for use with a specific patch. Alternatively or additionally, the device may include a window. Alternatively or additionally, the device may include a coded indicator, for example one or more diodes (e.g. a light emitting diode LED) and/or a display screen and/or a sound generator that indicates an aspect of device status and/or patch deployment.

In some embodiments, a device will include a timer and/or a real time clock. For example, the catch will be deployed and/or disengaged according to a schedule. Optionally the device may include a user interface for setting the timer. For example, an interface may include a display screen (for example including a liquid crystal display) and/or a setting control to set a time and/or dosage.

In some embodiments a device may be controlled remotely. For example a device may communicate with a remote controller and/or a computing device and/or clock. A remote control may be in addition to and/or in place of all or part of an integral user interface. For example, a patch control device may communicate wirelessly with a computing device (for example a cell phone). The computing device may display status and/or may control deployment of a patch. For example, a cell phone may store a prescription. Optionally the camera of the cell phone may be used to read a bar code on a medicine label. The phone may then determine if the medicine is proper and/or in agreement with the prescription. The phone may optionally compute a dose schedule and/or a deployment and/or timing of drug patch. The phone may optionally control patch deployment according to the prescription and/or according to user instructions. Alternatively or additionally, the phone may track deployment of the patch and/or dosage of the drug and/or give instructions and/or warnings to the user. Alternatively or additionally one or more sensors may sense a condition of a user and/or report them to a computing device. The computing device may give instructions and/or warnings to a user and or medical personnel according to the sensor output. Alternatively or additionally, the computing device may engage or disengage the patch according to instructions of the user the medical personnel and/or in accordance with a preprogrammed intervention in response to the condition of the user measured by the sensors. Optionally a sensor may be built into the patch control device and/or may be independent of the patch control device. Optionally a sensor may include a pulse sensor and/or a temperature sensor and/or an oxygen sensor (for example blood oxygen) and/or a $CO_2$ sensor.

In some embodiments a patch and/or patch controller may include a skin penetrating device. For example a microneedle may penetrate the skin and/or increase medicine penetration of the skin. Optionally a micro-needle and/or skin penetration device may be transitory. For example it may dissolve.

FIG. 17 is a side perspective view of a medicine patch controller device in accordance with some embodiments of the present invention. In some embodiments, a patch controller is designed to keep a contact between a patch roll within and a skin within a preferred range. For example the distance between the center of the roll and the skin may be adjusted according to the width of the roll.

In some embodiments, the distance between a roller and the skin may be adjusted according to the width of a rolled up patch. For example, a variable position suspension may be provided. For example, a variable position suspension may include a track 2646. Optionally track 2646 may be angled and/or curved to keep a desired distance and/or contact between an edge of a rolled up patch (e.g. at a separation line) and the skin. For example, for a case where the patch is rolled out and/or engaged to the skin as the roller moves towards the rear portion 2665 of the device and/or the patch is rolled up and/or dis-engaged from the skin as the roller moves towards the front portion 2666 of the device, the roll may get smaller as the roller moves from the back to the front of the device. Optionally, a track 2646 may be angled with respect to a skin attachment surface and/or attachment surface 2825. In some embodiments, an attachment surface may directly contact skin of a user. Alternatively or additionally a portion of a patch having may interface between attachment surface 2825 and the skin. For example the interface portion may have double sided tape connecting on one side to the skin and of the other side to surface 2825. For example, the interface may be part of a patch. Optionally, track 2646 may be angled towards the skin attachment surface at front portion 2666 and/or angled away from the skin attachment surface at the rear portion 2665 of the device. Alternatively or additionally, the track may have bends and/or steps. For example, at locations on the track at which the roller is located when section 823 reaches the skin of a user, track 2646 may have a step and or change in angle to adjust for a change of the width of the roll at section 823. For example the depth of the step may be approximately the thickness of patch 820 and/or the length of the step may be the width of section 823 at the edge of the rolled up patch. Optionally the length of steps may be adjusted along track 2646 to an account for changes in the length of the transition zone of a width change of the roll. For example, the length of the step may be larger where the roll is larger. Alternatively or additionally a force between a roller and a skin and/or a tension on a patch and/or a distance between a roller and a skin may be adjusted by an elastic element (for example a spring and/or an elastically compressible roller). For example the distance of the track from the skin attachment surface may change by between 0.1 and 0.5 mm and/or 0.5 to 1 mm and/or between 1 to 2 mm and/or between 2 to 4 mm over a distance of between 0 to 1 mm and/or between 1 to 2 mm and/or between 2 to 4 mm and/or between 4 to 8 mm and/or between 8 to 15 mm and/or between 15 to 30 mm and/or between 30 to 60 mm. Step changes in distance between the track and the skin attachment surface may be separated by a distance ranging for example between 1 to 2 mm and/or between 2 to 4 mm and/or between 4 to 8 mm and/or between 8 to 15 mm and/or between 15 to 30 mm and/or between 30 to 60 mm. The change of distance between the track and the attachment surface over a step may range for example between 0.1 and 0.5 mm and/or 0.5 to 1 mm and/or between 1 to 2 mm and/or between 2 to 4 mm. The length of the track over which a step change occurs may range for example between 0.1 and 0.5 mm and/or 0.5 to 1 mm and/or between 1 to 2 mm and/or between 2 to 4 mm.

In some embodiments, a sensor 2855 may be located on a skin attachment surface 2825. For example a sensor may include a physiological sensor, for sensing a physiological condition of a user. Alternatively or additionally a sensor may sense a condition of a patch (e.g. whether an adhesive is still viable) alternatively or additionally a sensor may sense a condition of the device (for example whether the device is near skin and/or connected to skin). For example, a rotation sensor 2837 may count rotations of motor 2618.

In some embodiments a patch control device may include a printed circuit board (PCB). For example, a PCB 2833 may be located in a drive housing section of a device. Optionally, PCB 2833 is attached to upper housing 2626*a* of the device. In some embodiments an actuator (for example motor 2618), a transmission (for example transmission 2615), a guide (for example track 2646) and/or a power transmitting member (for example drive shaft 2619) are attached to a skin fastener (for example an adhesive surface, for example attachment surface 2825 of lower housing 2626*b*). In some embodiments, a control element (for example PCB 2833 and/or microswitch 2634) and/or elements of a user interface (for example switch 2636, 2637) and/or an energy source and/or an indicator [for example an LED and/or a view screen]) may not be directly attached to a skin fastener. For example, elements not connected to a skin fastener may be connected to upper housing 2626*a*. Alternatively or additional parts may be connected in other ways. For example an energy source such as batteries 2617 may be connected to lower base 2626*b*. Alternatively or additionally a PCB may be connected to lower housing 2626*b*. Optionally a PCB connects to various parts of the device including for example motor 2618 and/or sensor 2855, 2837 and/or an energy source 2617 and/or a user control such as a button 2636 and/or a switch 2637. Optionally a PCB may include a processor and/or a communication device (for example a blue tooth transceiver) and/or a switch and/or a clock and/or a memory. Optionally, processing data may be performed by an outside processor (for example of a personal computing device) that may communicate, for example send commands and/or results, with an internal processor of the device.

Figure 18:
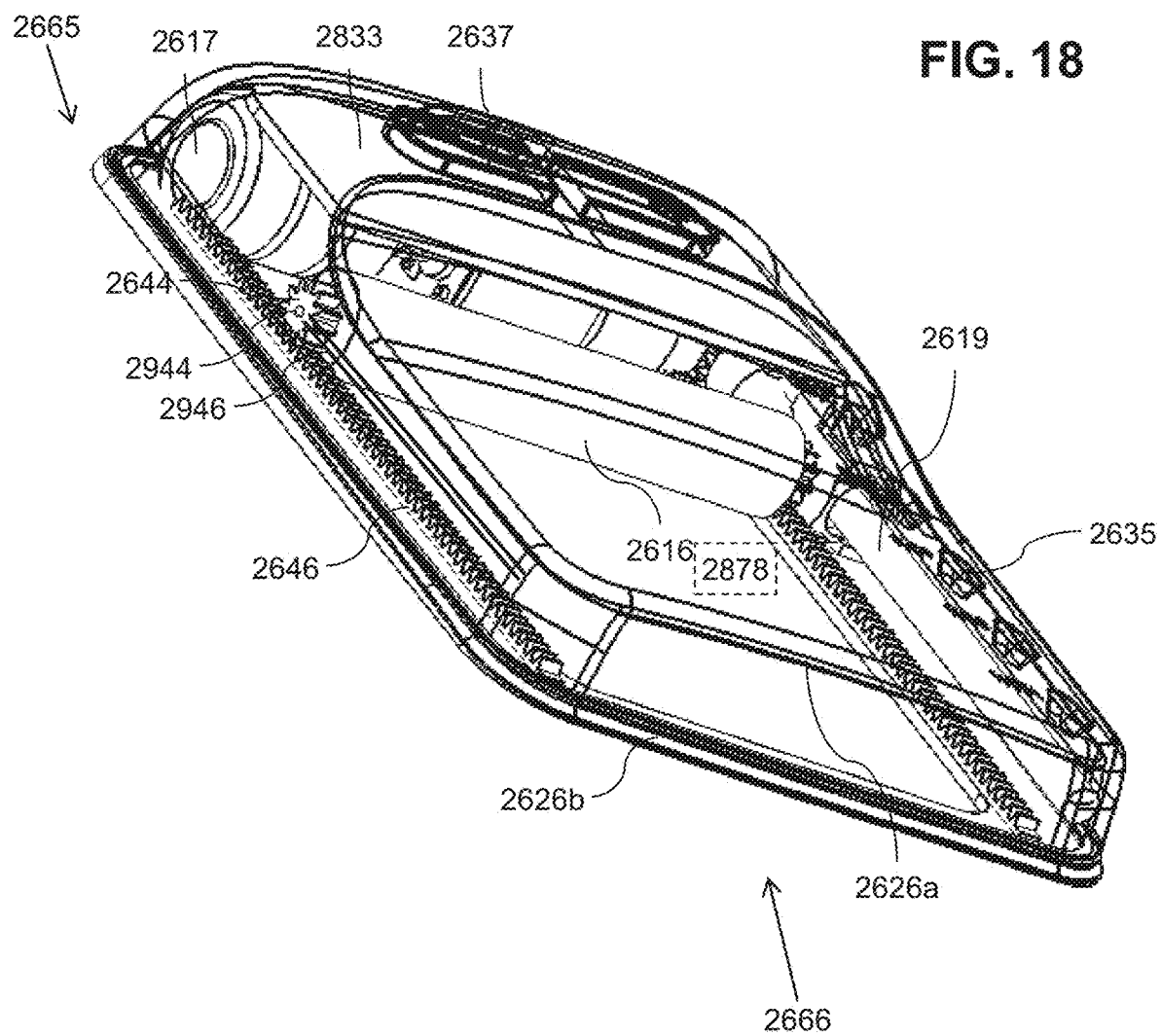
FIG. 18 is a front perspective view of a medicine patch controller device in accordance with some embodiments of the present invention.

FIG. 18 is a front perspective view of a medicine patch controller device in accordance with some embodiments of the present invention. Optionally the device may be designed to place a patch onto the skin avoiding bubbling and/or folding. For example, placement device may be configured to keep a predetermined pressure between the patch and the skin for example at a separation line and/or a predetermined distance between the when the patch is placed on the skin (for example along a separation line at which a rolled up patch is unrolled onto the skin). For example, a distance between a roller and the skin may be adjusted according to the thickness of the rolled up patch on the roller.

In some embodiments, rate of release the patch will be synchronized to a change in skin coverage. For example, the rate of rotation of a patch roller may be adjusted according to a diameter of the roll to equalize the rate of deposition of the patch on the skin and the rate of release of the patch from the roller.

In some embodiments, a track may be designed to cause a patch to be released as it is engaged and/or stored as it is disengaged. For example, a mechanism may be supplied to rotate a roller as it moves linearly to take up and/or release a patch in accordance with the area to be covered by the patch.

In some embodiments, the rate of release of a patch is proportional to a rate of rotation of a roller and a diameter of the rolled up patch. In some embodiments the rate of engagement and/or deposition of the patch is proportional to the rate of linear movement of the roller. Optionally a mechanism is supplied to synchronize the rate of release of the patch to the rate of engagement and/or to synchronize the rate of uptake of the patch to the rate of disengagement. For example a contact gear 2644 running along track 2646 may determine the rate of rotation of roller 2616. the spacing of teeth on track 2646 may be adjusted to synchronize rate of patch uptake and/or release the rate of patch disengagement and/or engagement. The teeth of the track may include various forms of gear linking mechanisms, for example apertures in a rack and/or indentations in a rack and/or bars and/or other forms of connections for example as used in rack and pinion systems. For example, where the diameter of the roll is large (for example in the roller position when the patch is disengaged for example in the embodiment of FIG. 18 in front section 2666) teeth may of track 2646 may be far apart (e.g. with a small pitch) so that the rotation rate per linear movement is reduced. For example, where the diameter of the roll is small (for example in the roller position when the patch is engaged for example in the embodiment of FIG. 18 in rear section 2665) teeth may of track 2646 may be close together (e.g. with a larger pitch) so that the rotation rate per linear movement is increased.

In some embodiments the distance between teeth along the track may change nonuniformly. For example, the distance between teeth may be relatively stable over a long area and then change where there is a change in the radius of the roll. For example, the distance between teeth may increase by steps distance by the circumference of the roll. For example, the step change may occur where the section of roller including the leading of the roll (for example section 823) faces the skin and/or an opening in the base of the control device (for example skin opening 2878). For example, the tooth distance may remain fixed over a distance ranging for example between 1 to 2 mm and/or 2 to 4 mm and/or 4 to 8 mm and/or 8 to 20 mm and/or 20 to 40 mm or more and then change at a step location having length ranging for example between 0 to 1 mm and/or 1 to 2 mm and/or 2 to 4 mm and/or 4 to 8 mm and/or 8 to 20 mm or more. For example, the tooth distance may change at a first rate over a distance ranging for example between 1 to 2 mm and/or 2 to 4 mm and/or 4 to 8 mm and/or 8 to 20 mm and/or 20 to 40 mm or more and then change at step location at a rate between 1.1 to 1.5 times as much and/or between 1.5 to 3 times or more in comparison to the first rate. Optionally a step location may have a length ranging for example between 0 to 1 mm and/or 1 to 2 mm and/or 2 to 4 mm and/or 4 to 8 mm or more. A distance between teeth may change for example by a ratio between 1/0.99 to 1/0.95 and/or between 1/0.95 to 1/0.8 and/or between 1/0.8 to 1/0.5. The change in teeth distance may occur over a distance of the track between 0 to 1 mm and/or between 1 to 2 mm and/or between 2 to 4 mm and/or between 4 to 8 mm and/or between 8 to 15 mm and/or between 15 to 30 mm. The change of distance between teeth may occur over a step. The length of the track over which a step change occurs may range for example between 0.1 and 0.5 mm and/or 0.5 to 1 mm and/or between 1 to 2 mm and/or between 2 to 4 mm and/or 4 to 8 mm.

In some embodiments, an second guide may keep a roller on a track. For example a pin 2944 on contact gear 2644 may slide in a slot 2946 in housing (for example housing 2626*a*). Optionally, pin 2944 in slot 2946 prevents contact gear 2644 from being pushed upward away from track 2646. Optionally, tracks 2646 and gears 2644 are supplied on opposing ends of roller to synchronize linear movement and rotation of roller 2616. Synchronizing opposite sides of the roller and/or different points of the roller may prevent twisting of the patch and/or buckling and/or bubbling and/or folding during engagement and/or disengagement. Optionally another element may serve as a guide holding a gear on a track. For example on an opposite side drive shaft may hold a gear 2644 on track 2646.

Loading a Patch to a Controller Device

Figure 19:
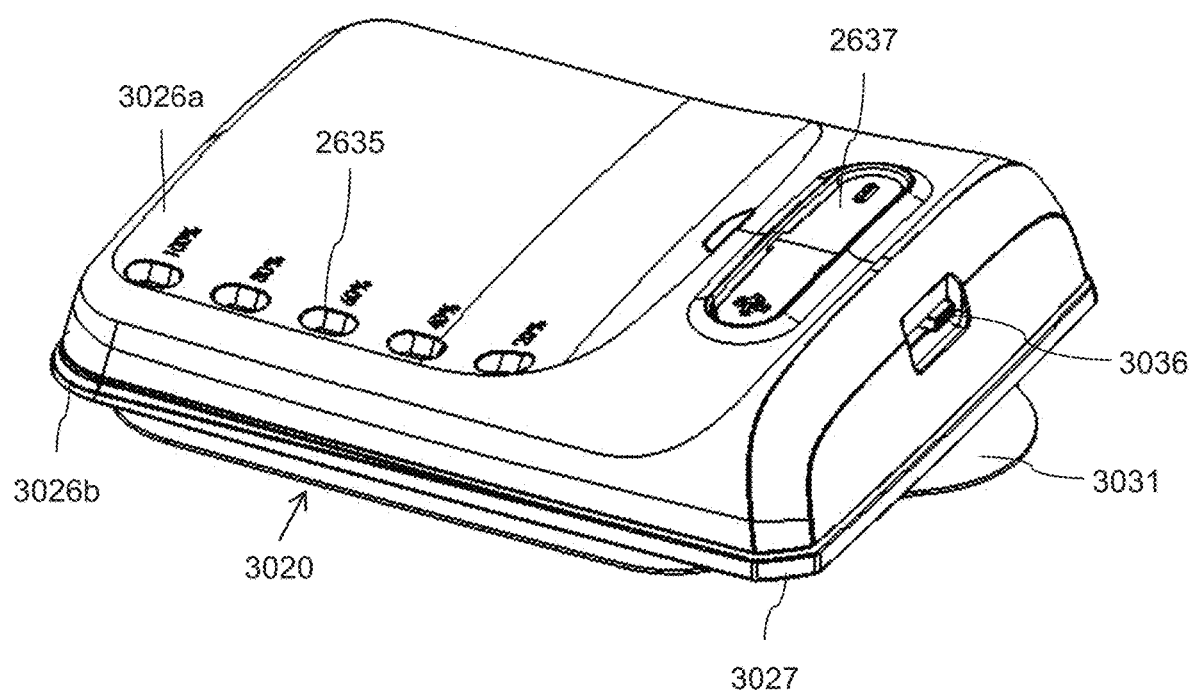
FIG. 19 is a perspective external view of a patch attached to a control device in accordance with an embodiment of the current invention.

FIG. 19 is a front perspective external view of medicinal patch and a patch controller device in accordance with some embodiments of the present invention. In some embodiments set up of a patch control device may include connecting the device to a patch. For example, an alignment jig may align a patch control device and a patch and/or facilitate connecting the patch to the control device. Optionally the patch and/or the control device will include an alignment feature. For example the alignment feature may facilitate proper alignment between the patch and/or the controller and/or the alignment jig. Optionally, set up of the control device may include connecting the device to an external processor, for example a personal computing device and/or a wireless device. Optionally, wireless connection may be automatically initiated upon unpacking of the control device. Optionally, the external device may include instruction and/or help in setting up the control device.

Figure 20A:
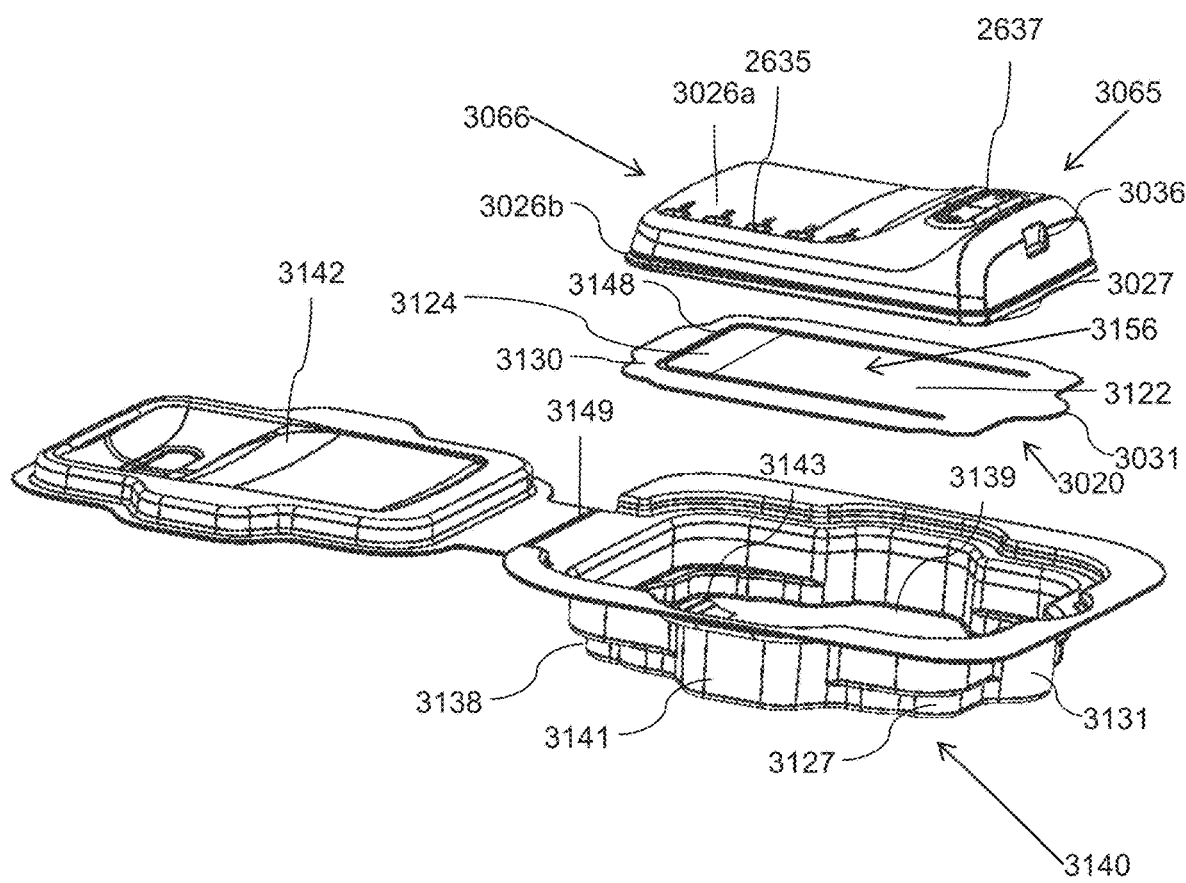
FIG. 20A is a perspective view of a patch and a patch controller positioned for placement in an alignment jig in accordance with an embodiment of the present invention.

In some embodiments a patch and/or a patch controller will include an alignment feature. For example, one or more corners of a housing 3026a and/or 3026b may differ from other corners thereof such that the device will fit into an alignment jig in a limited number of orientations. For example, in housings 3026a and 3026b at least one corner is rounded. An alignment feature 3027 includes a corner that is cut off diagonally. Optionally, control device fits to an alignment jig only when the alignment feature 3027 is oriented to corresponding alignment feature of the alignment jig (for example as illustrated in FIG. 20A, the alignment feature 3127 may include a matching diagonal corner 3027 of the alignment jig). Alternatively or additionally, an alignment feature may include a hole for example matching a pin and/or a groove for example matching a projection. Optionally a patch 3020 may include an alignment feature for example including a protrusion 3031 and/or a non-symmetrical shape and/or a hole and/or a cut out. Optionally alignment jig 3140 may include an alignment feature matching and/or fitting alignment feature 3031 (for example hollow 3131 fitting protrusion 3031 of patch 3020.

In some embodiments a patch may be connected to a roller (for example roller 2616) of a device and/or an attachment surface (for example surface 2825) by an adhesive. For example the adhesive may be on the back (dorsal) side of the patch. Alternatively or additionally an adhesive may be applied to roller 2616 and/or surface 2825. Alternatively or additionally a different connector may be used. For example, a reusable fastener may be used. Optionally, a hook and loop fastener may be user and/or a clip and/or a pin and/or a screw.

In some embodiments, a portion of patch 3020 may project beyond the edge of a patch control device. For example, a portion of a patch may be used to adhere the control device to a user. For example, a portion of the patch may include two sided adhesive to adhere an attachment surface (for example surface 2825) of the control device to a skin of a user. Optionally the patch may include a flexible skirt that extends beyond the attachment surface. Optionally, the skirt may extend outward, for example as illustrated if FIG. 19. Alternatively or additionally the skirt may extend inward, for example into the central opening that includes patch area 2878. In some embodiments, an adhesive skirt may be stiffened, for example with a flexible plastic stiffener. Optionally the skirt may hold the control device to skin. Optionally the stiffener may make it easier to adhere the skirts to the skin and/or may make the skirt hold to the device more rigidly.

FIG. 20A is a perspective view of a patch and a patch controller ready for placement in an alignment jig in accordance with an embodiment of the present invention. In some embodiments, an alignment jig fits to a medicine patch and/or a patch control device in a particular alignment that facilitates alignment and/or attachment of the patch to the control device. Optionally, the patch and/or device will reversibly fit to the alignment jig, for example allowing placement and/or replacement in the alignment jig without damage to the patch and/or the control device. Optionally attachment of the patch to the control device is irreversible. For example, the patch may adhere to the alignment jig with adhesive. Attaching and/or removing the patch from the control device may compromise the patch, for example by weakening the adhesive and/or stretching the patch due to the strength of the adhesion to the control device.

In some embodiments, patch 3020 includes a stationary portion 3130. Optionally, stationary portion 3130 may include adhesive of both sides. For example adhesive on the dorsal side may adhere stationary portion 3130 to an attachment surface of a housing (for example to attachment surface 2825 of a lower portion 2626b of a control device). For example, adhesive on the ventral side of stationary portion 3130 of the patch may adhere to stationary portion and/or attachment surface of the housing to the skin of a subject. For example, when the control device is positioned on a subject, stationary portion 3130 may be immobile and/or sandwiched between contact area of the housing and the skin of the subject. In some embodiments, stationary portion 3130 completely and/or partially surrounds an engageable portion 3156 of the patch (engageable portion may for example be engaged and/or disengaged from the skin while the patch controller remains on the skin).

In some embodiments, the control device has all of its connections to patch 3020 exposed on one side (e.g. the ventral side of the device connects to the dorsal side of patch 3020). For example, a contact zone of the roller contacts adhesive 3124 of the leading mobile end of mobile portion 3156. In the example of FIG. 20A, patch 3020 is loaded to the patch controller while the roller of the patch controller is optionally located over adhesive 3124, which is for example in the front end 3066 of the device. After loading, the disengageable portion 3156 of the patch is optionally rolled up onto the roller as the roller moves backwards towards the rear end 3065 of the device. For example rear end 3065 may include the power train of the device. Alternatively or additionally, the direction of loading and rolling may be the opposite of the direction. Optionally, an attachment surface (for example surface 2825) of the device that connects to stationary portion 3130 of patch is exposed on a ventral face of the control device. For example, pushing ventral surface of the control device onto the dorsal surface of patch 3020 loads patch 3020 to the control device. Optionally, alignment jig 3140 has a base with contours that position patch 3020 properly to connect to each part of the control device. For example, a contact zone of a roller may be recessed with respect to attachment surface. Optionally the base of alignment jig includes a protrusion 3143 that holds the free leading portion including a connector (for example adhesive 3124) extended upward to contact the roller when the control device is lowered into place onto alignment jig 3140. Optionally, after connection, a mobile disengageable portion 3156 may be wound to the roller (e.g. into a disengaged state). For example, the disengageable portion may be would while the control device is still on the alignment jig. For example, the ventral side of the patch may be covered with a liner. Optionally, the liner may remain attached to the stationary portion 3130 of patch 3140 and the skin contact portion of the housing while the disengageable portion 3156 is peeled away from the liner. Optionally, the user peels the liner off of stationary portion 3130 of the patch after attachment of patch 3020 to the control device and/or after detachment of the patch and/or control device from the alignment jig and/or before placement onto the skin and/or the delivery site.

In some embodiments, a leading portion and/or a mid portion of an disengageable portion 3156 of patch 3020 is separated from stationary portion 3130 of the patch by a discontinuity, for example a cut out 3148. For example, cut out 3148 permits leading portion and or central portion of disengageable portion 3156 to roll up onto a roller while stationary portion 3130 remains stationary with respect to the skin of the subject and/or the attachment surface of the control device. For example, stationary portion 3130 may be sandwiched between the skin of the subject and/or the attachment surface of the control device.

In some embodiments, patch 3020 may be sold as a whole conventional patch without a discontinuity. For example the discontinuity is optionally cut into the patch after production and/or sale. Optionally, a device and/or die may be supplied to cut a discontinuity. For example, the cut out device may be a separate device, and/or may be including in packaging of a patch and/or of a dosage control device. For example alignment jig 3140 may include a die and/or blade to cut the discontinuity. For example a convention patch may be modified by cutting a discontinuity. Optionally the discontinuity will be in a non-active area. For example cutting a discontinuity into a patch may not compromise an active area and/or a drug reservoir and/or a release membrane.

In some embodiments, leading portion of a disengageable portion 3156 of patch 3020 includes adhesive 3124 on its dorsal side. Adhesive 3124 optionally connects leading portion to a roller of the control device. Alternatively or additionally, the roller may be coated with adhesive. Alternatively or additionally, the roller and/or a leading portion may include a magnet and/or a clip and/or a hook and/or a slit and/or a hook and loop connector for example for connecting the free portion of the patch to the roller.

In some embodiments, a protector may protect an active zone and/or a skin attachment surface of a patch during storage. For example, a flexible backing including for example a liner 3122 covers mid section of disengageable portion 3156. When patch 3020 is stored (for example by rolling up onto a roller such that disengageable portion 3156 is wound around the roller), the medicated surface of disengageable portion 3156 is optionally covered by liner 3122. Optionally liner 3122 is made of a chemically inert and/or non-stick and/or non-reactive substance that will protect the drug in disengageable portion 3156. Optionally liner 3122 is made of a non-stick substance that will protect the adhesive on the skin contact area of disengageable portion 3156 of patch 3020. For example liner 3122 may be made of a non-reactive coating over a substrate. For example a non-reactive coating may include Polyethylene and/or the substrate may include a metal foil (e.g. aluminum) with a thickness between 0.05 and 0.2 mm. Alternatively or additionally a substrate may include paper and/or plastic.

In some embodiments, a patch control system may include an alignment jig 3140. For example alignment jig 3140 may include a cavity of a blister package for patch 3020 and/or the control device. For example, the control device and/or patch 3020 may be supplied to a user packed inside of alignment jig 3140 and/or sealed with a backing for shipping and distribution. Optionally, alignment jig includes a cover 3142. For example, cover 3142 may be connected to the main cavity by a hinge 3149 (for example a hinge may include a folded and/or scored plastic). For example when the patch 3020 and/or the control device are inserted into alignment jig 3140, closing cover 3142 may push patch 3020 firmly onto the control device and/or attach patch 3020 to the control device.

In some embodiments, positioning the patch and the control device onto the alignment jig will connect the patch to the control device. For example, once patch 3020 is lying on base 3139 with connector 3124 exposed and/or raised away from base 3139 towards the control device by protrusion 3143, the control device is placed onto alignment jig 3140 with the skin attachment surface of the control device facing towards the exposed connector 3124 on patch 3020. Optionally cover 3142 is closed and/or snaps down on the control device securely pushing the attachment surface of the control device against stationary portion 3130 and/or pushing the roller of the control device against connector 3124. Optionally alignment jig 3140 is shaped such that patch 3020 and/or the control device are pushed into proper alignment when they are positioned on alignment jig 3140. For example, a cavity of device 3140 may have beveled walls and/or an inward projecting section 3138 leading to a tight fitting compartment such that putting a patch and/or control device into the cavity pushes them into mutual alignment.

Figure 20B:
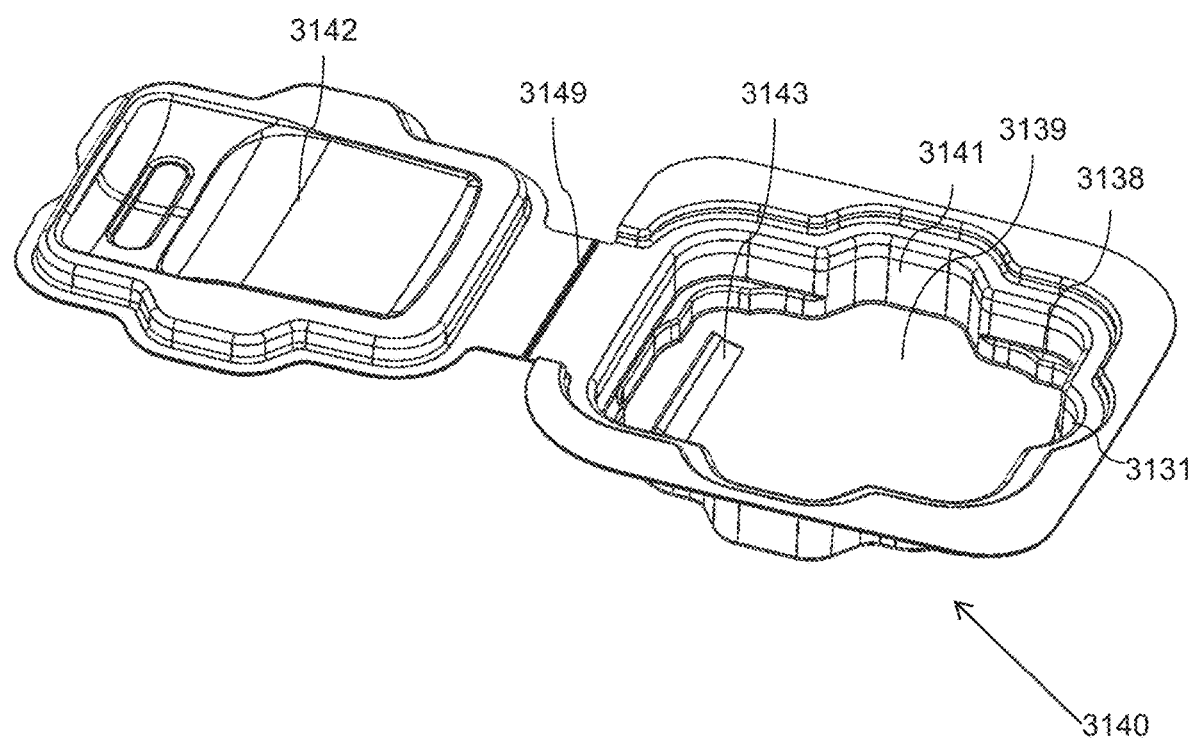
FIG. 20B is a perspective view of an alignment jig in accordance with an embodiment of the present invention.

FIG. 20B is a perspective view of an alignment jig in accordance with an embodiment of the present invention. Optionally, protrusion 3143 is designed to increase the surface of contact between connector 3124 and a roller of the control device. For example a surface of protrusion may be shaped and sized to increase contact with the roller. For example the inner face may have a concave form to fit the convex form of the roller. Some portion of an alignment jig may be made (for example space 3141) larger than the control device for example making it easier to get a finger into the alignment jig and remove the patch controller and/or patch.

Figure 21:
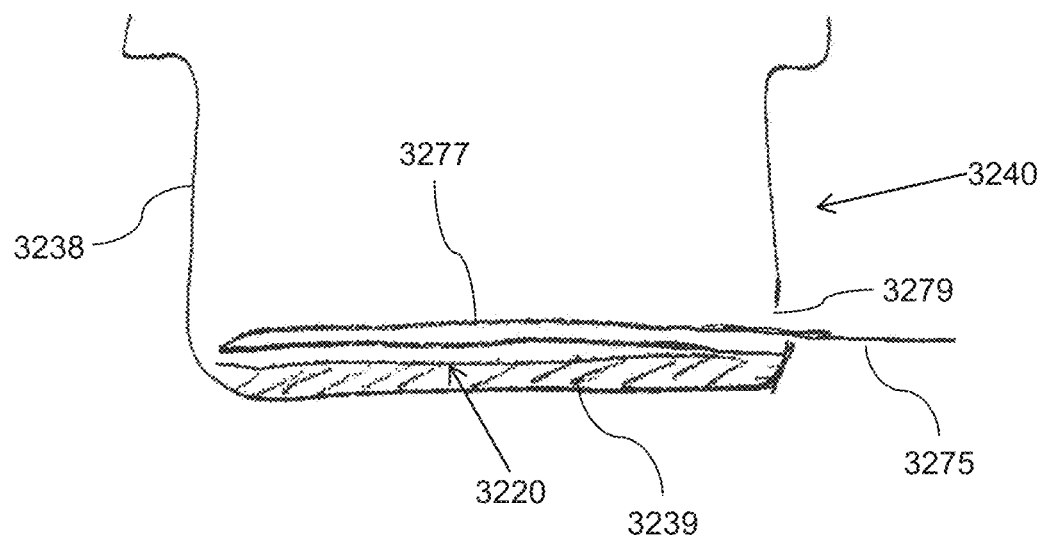
FIG. 21 is a schematic view of a patch in an alignment jig in accordance with an embodiment of the current invention.

FIG. 21 is a schematic view of a patch in an alignment jig in accordance with an embodiment of the current invention. In some embodiments an adhesive liner may be taken off of a patch while the patch is in an alignment jig. For example, a pull tab 3275 of an adhesive liner may protrude through a slit 3279 in a wall 3238 of an alignment jig 3240. Optionally, liner 3277 may be doubled over such that pulling tab 3275 horizontally peels liner 3277 off of a patch 3220. Optionally, patch 3220 may be taken out of a sterile wrapper and inserted into alignment jig 3240 and/or placed against a base 3239 of alignment jig 3240 and/or tab 3275 may be threaded through slit 3279 by a user. Alternatively or additionally, patch 3220 may be preloaded in alignment jig 3240. In some embodiments once patch 3220 is in place in alignment jig 3240 and/or a connector is exposed, a control device may be inserted into a alignment jig and connected to patch 3220, for example as described herein above in connection to patch 3020, alignment jig 3140.

Figure 22:
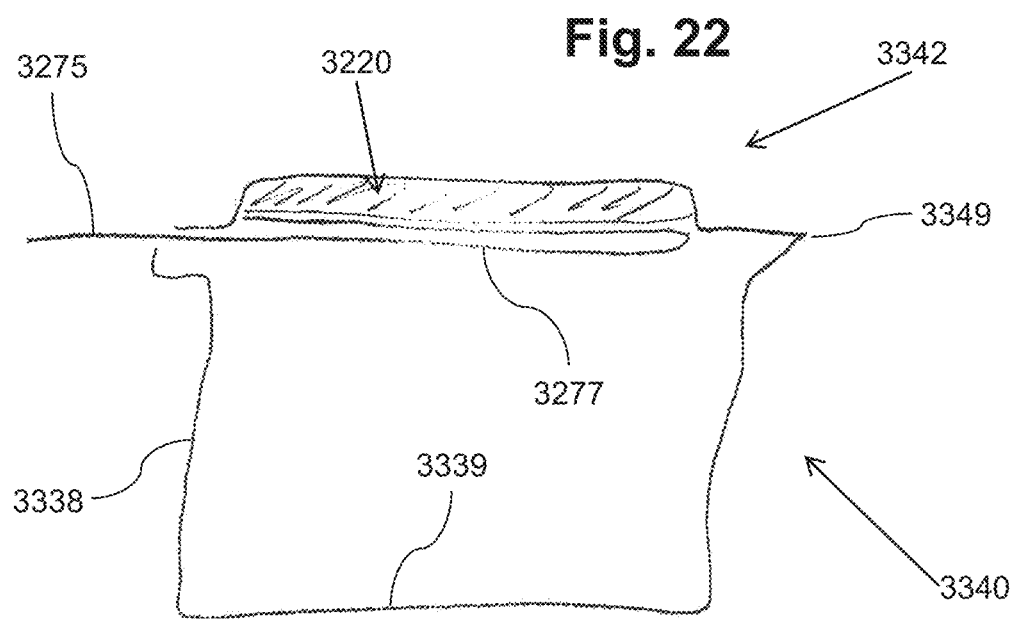
FIG. 22 is a schematic view of a patch in a cover of an alignment jig in accordance with an embodiment of the current invention.

FIG. 22 is a schematic view of a patch in a cover of an alignment jig in accordance with an embodiment of the current invention. In some embodiments a patch 3220 may fit into a cover 3342 of an alignment jig 3340. Optionally a control device fits into a cavity of alignment jig 3340, for example held in place by walls 3338 and base 3339. Optionally an attachment surface of the control device will face upwards toward cover 3342. Optionally, cover 3342 is closed while liner 3277 covers an adhesive connector of patch 3220. For example, cover 3342 may be closed by rotating around a hinge 3349. After closing cover 3342, a tab 3275 optionally extends out of a space between cover 3342 and alignment jig 3240. Optionally, liner 3277 is pulled off of patch 3220 while cover 3342 is closed. Alternatively or additionally liner 3277 is pulled off of patch 3220 while cover 3342 is open. Removing adhesive covering 3277 optionally exposes an adhesive with is pushed by cover 3342 against an attachment surface and/or roller of the control device. Alternatively or additionally, patch 3220 is attached to the control device by removing an adhesive liner 3277 and/or closing cover 3342 to contact patch 3220 with the attachment surface of the patch control device In some embodiments, patch 3220 is supplied to the user already in cover 3342 and/or the patch control device is supplied to the user already in the cavity of control device 3340. Alternatively or additionally, the control device may be supplied in the cavity of alignment jig 3340 and/or patch 3220 may be supplied in a separate sterile package. For example a user may remove a patch form its sterile packages and place it into cover 3342.

Figure 23:
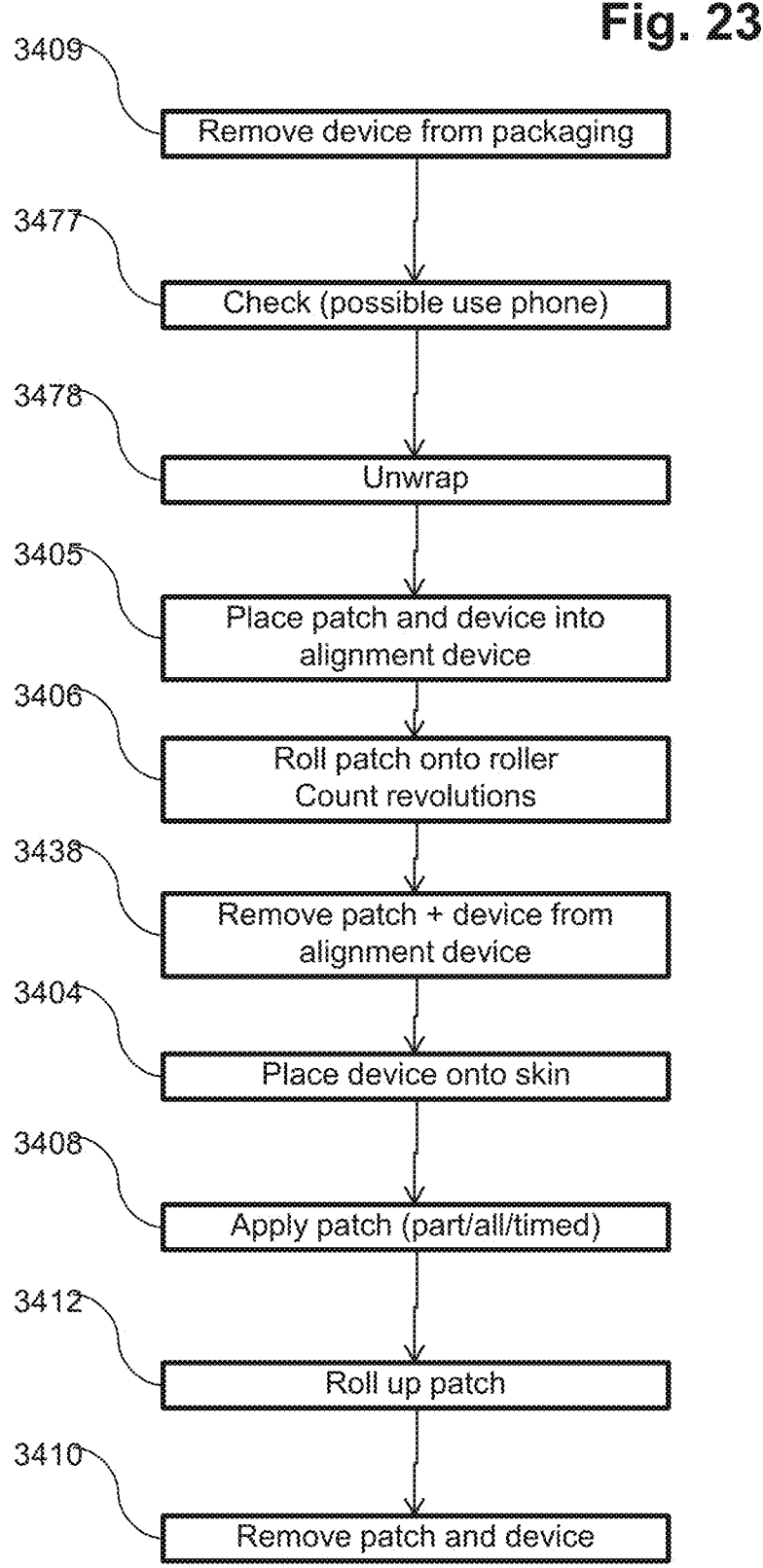
FIG. 23 is a flow chart illustration of loading a patch to a control device in accordance with some embodiments of the current invention.

FIG. 23 is a flow chart illustration of loading a patch to a control device in accordance with some embodiments of the current invention. In some embodiments, a device may include a built in user interface for monitoring and/or controlling deployment of the patch. Alternatively or additionally, the device may be configured for remote control and/or monitoring. In some embodiments, a device may be packed in a protective wrapper. Optionally, unpacking the device from the wrapper may start a set procedure (for example pairing the device with an external communication and/or data processing device and/or a set of instructions may begin to be presented). Optionally, a wrapping of a device and/or a patch may serve a function in preparing and/or storing the device. For example, a device and/or a patch may be packed in a packing that is used to align the patch and/or the device.

In some embodiments a patch control device is prepared for use in conjunction with an external data processing device. For example, when the control device is removed from a protective packaging 3409 the device may automatically be activated. For example, removing the device from the packaging may pull a battery isolator out of a circuit. Once activated there may be a limited time to use the device. Optionally, the device may pairs with an external computing device (for example a smartphone of a user), for example via a wireless connection. For example the device may stop set up until a proper connection to an external device has been completed. Optionally pairing is initiated automatically when the control device is unpacked.

In some embodiments a device may go through a checking 3477 step before use. In some embodiments, the checking step may be performed by an internal processor of the device. In some embodiments, checking steps may be performed by an external device. For example, a patch may have a built in chip that is registered by the control device (for example using a radio frequency identification chip RFID). Alternatively or additionally, a user may take a picture using and external computing device (for example a smartphone) of a label on the patch (for example a bar code). Based on data from the label and/or the control device, the external computing device may verify that the medication of the patch is proper. The control device and/or computing device may further test and/or quizzes the user to make sure that he is the intended user of the device and/or to make sure that he is competent to properly use the device.

In some embodiments a medicine patch may be unwrapped 3478 and/or fit 3405 to an alignment jig and/or the control device. In some embodiments, the patch and the control device may be supplied in separate wrappings. Optionally both the patch and the control device may be removed from their original wrapping. Optionally, after unwrapping 3478, both the patch and control device may be inserted into an alignment jig. For example, the alignment jig may include part of the original wrapping of the patch and/or the device. Optionally, unwrapping 3478 the patch may include removing a protective liner from the dorsal face of the patch. For example, removing the liner of the dorsal face may expose an adhesive for attaching to a roller of a patch control device and/or an adhesive for attaching to a skin attachment surface of the device. Alternatively or additionally, both the control device and the patch may be partially unwrapped. For example a cover may be removed from a blister containing a control device and/or an aseptic seal may be and/or a protective liner may be removed from a dorsal face of a patch. Optionally, the patch and/or the device may remain in a respective part of the wrapping used for alignment. For example, the patch and/or the device may remain in a plastic blister. Optionally, the blisters of the device and the patch are designed to fit and/or attach to each. For example the orientation of the blisters may orient the patch for connection to the device. Alternatively or additionally, the patch may be packed in an alignment jug. For example, the patch may be packed in a blister that fits the control device when the control device is aligned to the patch and facilitates proper connection of the patch to the control device. Alternatively or additionally, the control device may be packed in an alignment jig. For example, the control device may be packed in a blister that fits the patch when the patch is aligned to the control device. The alignment jig may facilitate proper connection of the patch to the control device.

In some embodiments, after the patch is loaded to the device, an applicator of the device (for example a roller) may roll 3406 the active portion of the patch to a non-engaged position. A sensor and/or controller may be used to track the patch status, for example by counting revolutions of a motor and/or a roller. Optionally, as the active portion of the patch is rolled up, it is separated from its original liner and the medicated portion of the patch (on the ventral skin side) is rolled onto a liner on the dorsal side of the patch.

In some embodiments the device and/or patch may be removed 3438 from the alignment jig. Optionally, after removing the control device and/or patch from the alignment jig, the user peels an adhesive liner off of the ventral face of the patch. After removal of the ventral adhesive liner, the device with the patch attached is optionally placed 3404 onto the skin. Optionally, placement 3404 onto the skin is with the patch rolled up in a disengaged state. Optionally after placement, the patch may be engaged 3408 to the user at a predetermined time and/or in response to a sensor and/or according to a user commend. Optionally after engagement 3408, the patch may be disengaged 3412 from the user at a predetermined time and/or in response to a sensor and/or according to a user commend. Alternatively or additionally, the device may be attached to the skin of the user with the patch in an engaged state. The control device may optionally disengage all or part of the patch according to a schedule, a command, a sensor output etc. A patch and device are optionally removed 3410 from a user, for example at an end of treatment and/or when the patch is used up.

Guides

Figure 24A:
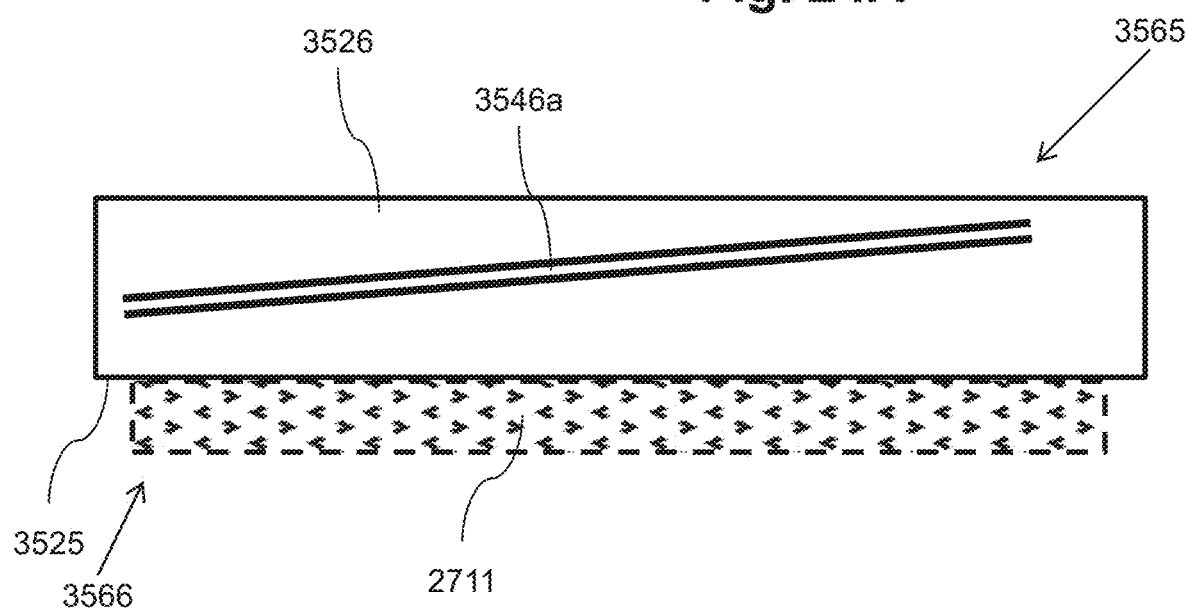
FIGS. 24A and 24B illustrate guides for a roller in accordance with an embodiment of the current invention.
Figure 24B:
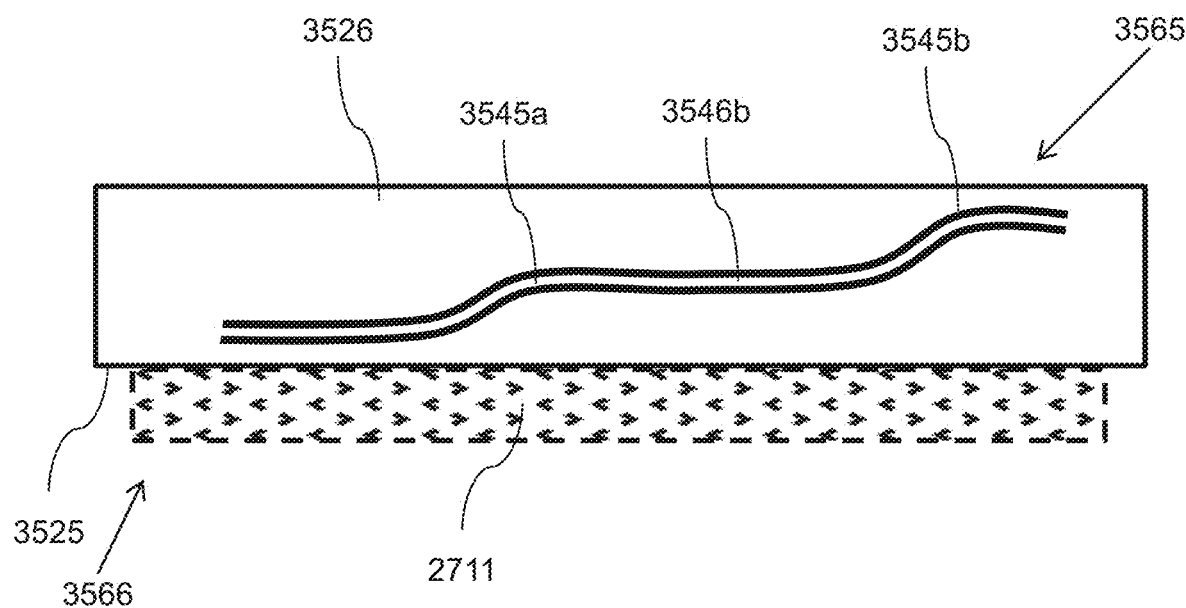

FIGS. 24A and 24B illustrate guides for a roller in accordance with an embodiment of the current invention. Optionally, guides 3546a and 3546b are not parallel to a skin attachment surface 3525 of a patch control device.

In some embodiments, for example as illustrated in FIG. 24A, a guide 3546a may be at an angle to attachment surface 3525. For example, a patch may be loaded to a device and/or at an engaged state when a roller is positioned at a front end 3566 of guide 3546a. Optionally, guide 3546a is positioned on a housing 3526 of the control device such that as the patch is rolled up, the roller is moved away from skin attachment surface 3525. For example, this may keep the edge of the roll of the patch within a desired range of distance to skin attachment surface 3525 and/or skin 2711 as the patch is rolled up and/or roller moves towards the rear end 3565 of track 3546a and/or as the radius of the roll grows.

In some embodiments, for example as illustrated in FIG. 24B, an angle between guide 3546b and skin attachment surface 3525 may change along the length of guide 3546b. For example, guide 3546b may have steps 3545a and/or 3545b. As a roller moves along track 3546b it may be moved along steps 3545a and/or 3545b toward or away attachment surface 3525. For example, a patch may be loaded to a device and/or at an engaged state when a roller is positioned at a front end 3566 of guide 3546b. Optionally, guide 3546b is positioned on a housing 3526 of the control device such that as the patch is rolled up, at a position where a section of the roller including the leading edge of the roll is positioned facing the skin attachment surface 3525 and/or skin 2711 the roller is moved away from skin attachment surface 3525. For example, this may keep the edge of the roll of the patch within a desired range of distance to skin attachment surface 3525 and/or skin 2711 as the patch is rolled up and/or roller moves towards the rear end 3565 of track 3546b and/or as the radius of the roll grows.

Alignment Jig

Figure 25:
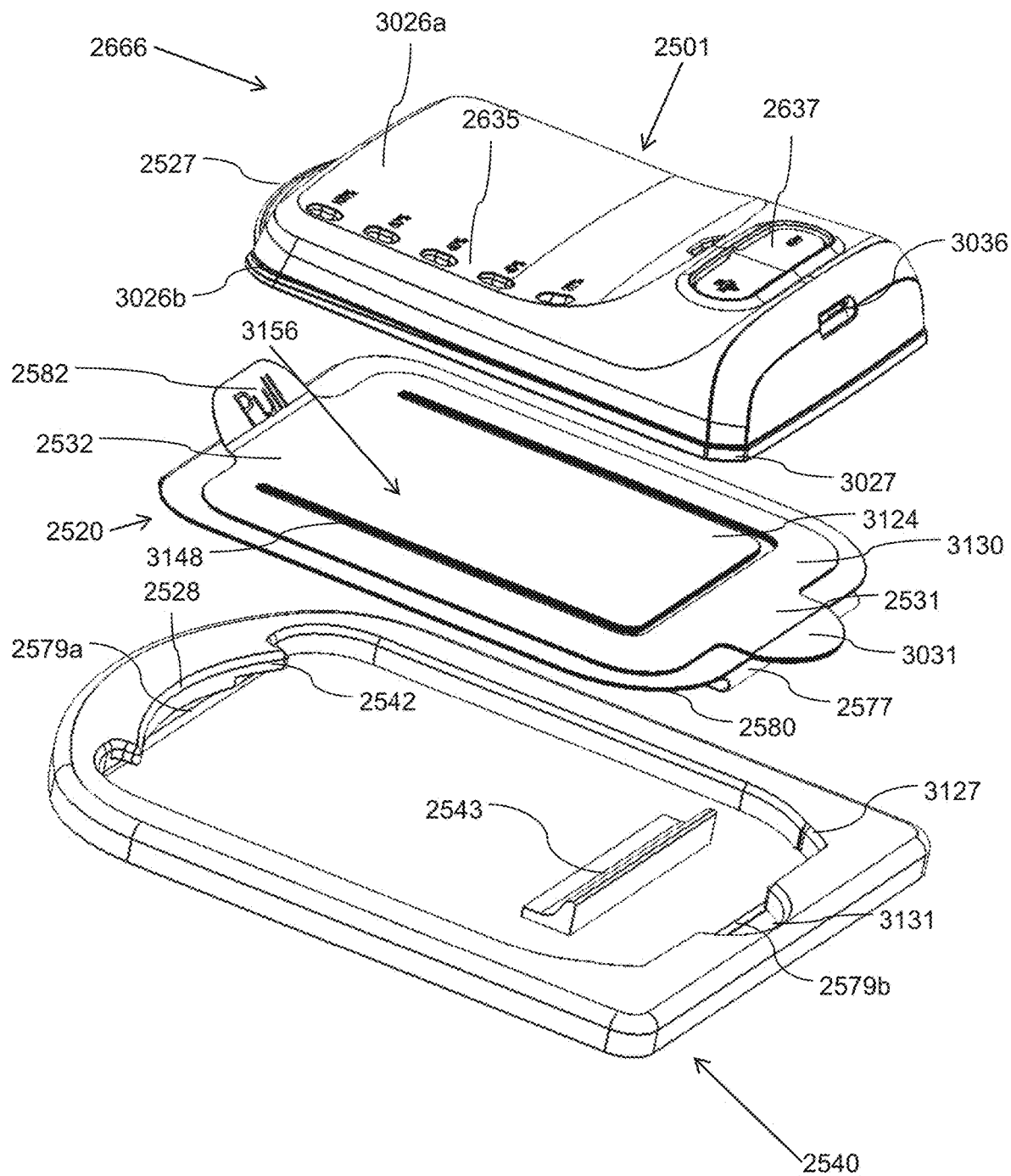
FIG. 25 is an illustration of a dosage control device and a kit for loading a transdermal patch 2520 to the device in accordance with an embodiment of the current invention.

FIG. 25 is an illustration of a dosage control device and a kit for loading a transdermal patch 2520 to the device in accordance with an embodiment of the current invention. In some embodiments, the kit will include an alignment device (for example jig 2540) and/or a pharmaceutical patch (for example patch 2520) and/or a patch adaptor (for example adapter 1401). Optionally, jig 2540 may facilitate alignment between a dosage control device (for example device 2501) and a pharmaceutical patch (for example patch 2520). In some embodiments, patch 2520 may be packaged and/or sold with and/or preconnected to jig 2540.

In some embodiments, jig 2540 includes an alignment feature 3131. Optionally, alignment feature 3131 matches a corresponding alignment feature 3031 of patch 2520. For example, feature 3131 may include an indentation that fits a protuberance of alignment feature 3031. For example, patch 2520 may be supplied to a user separate from jig 2540. The user may align patch 2520 to jig 2520 using features 3031 and/or 3131. Alternatively or additionally, patch 2520 may be pre-attached and/or packaged with jig 2540. Optionally, features 3031 and/or 3131 may help keep patch 2520 aligned to jig 2540. Alternatively, a jig may not include an alignment feature for a patch, for example when the patch is preloaded and/or pre-attached to the jig.

In some embodiments an alignment feature may include a protrusion. For example, an alignment feature may include protrusion 2543. In some embodiments, there may be several alignment features. For example, some alignment features may be visible to a user and some may be automatic.

Figure 26:
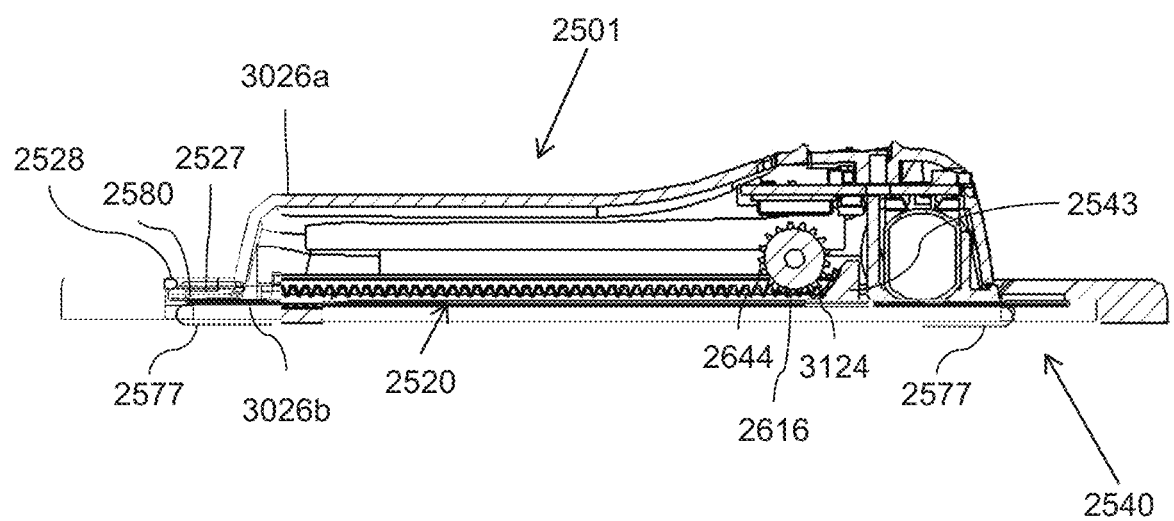
FIG. 26 is a cutaway side view of a dosage control device and patch aligned together with a jig in accordance with an embodiment of the current invention.

For example, a user may align device 2501 to jig 2540 by aligning feature 3131 to feature 3031. As device 2501 approaches jig 2540, another feature may adjust the final alignment. For example, as device 2501 approaches its final position on jig 2540, contact between protrusion 2543 and a roller (for example roller 2616 as illustrated in FIG. 26) may guide the final alignment of device 2501 to jig 2540.

In some embodiments, jig 2540 includes an alignment feature 2528. Optionally, alignment feature 2528 may match a corresponding alignment feature 2527 of dosage control device 2501. For example, feature 2528 may include an indentation that fits a protuberance of alignment feature 2527.

In some embodiments, patch 2520 may include a ventral liner 2577. Optionally, patch 2520 may include an active zone on a ventral side thereof and/or a ventral adhesive. For example, the adhesive may be configured to adhere the patch and/or an active zone thereof to the skin of a subject. Optionally, the active zone may be configured to deliver a pharmaceutical to the skin of a subject at a controlled rate. Alternatively or additionally, patch 2520 may include an adapter. For example, the ventral side of patch 2520 may include a ventral adhesive configured to adhere to a pharmaceutical patch for use with dosage control device 2501. Optionally ventral liner may protect the active zone and/or the ventral adhesive from damage during storage of patch 2520 prior to use. Alternatively or additionally, patch 2520 may not include a liner. For example, the ventral surface of the patch (optionally including an active zone and/or a ventral adhesive) may contact, be attached to and/or be protected by jig 2520. For example, a surface of jig 2540 may be made of a substance that is chemically inert with respect to the active zone and/or the ventral adhesive of patch 2520.

In some embodiments, a patch may include a stationary portion. For example, patch 2520 includes a stationary portion 3130. Optionally, stationary portion 3130 is sized and shaped to fit to and/or attach to a lower frame 3026b of dosage control device 2501. For example, stationary portion 3130 includes adhesive on two sides and/or is configured to adhere lower frame 3026b and/or to a skin of a subject.

In some embodiments, a patch may include a disengageable portion. For example, patch 2520 includes a disengageable portion 3156. Optionally, disengageable portion 3156 is configured to move in relation to stationary portion 3130. For example, disengageable portion 3156 may be partially separated from stationary portion 3130 for example by a cut out 3148. Optionally, disengageable portion 3156 includes an attachment portion 3124 which is positioned and/or configured to connect disengageable portion 3156 to an actuator of dosage control device 2501.

In some embodiments, a patch may include a skirt. For example, patch 2520 includes a flexible skirt 2580. Optionally, skirt 2580 extends beyond the edge of stationary portion 3130. For example, flexible skirt 2580 may include a stiffener and/or an adhesive. Optionally, when patch 2520 is attached to a flexible surface (for example skin) and/or pulled away from the surface, skirt 2580 flexes with the surface and/or makes it harder to detach patch 2520 and/or stationary zone 3130 from the surface. For example, when stationary portion 3130 is attaching a frame 3026b of device 2501 to a flexible surface, skirt 2580 makes it harder to detach patch 2520 and/or device 2501 and/or stationary zone 3130 from the surface.

In some embodiments, the skirt of the base may extend beyond an area attached to the frame of the dosage control device between 1 mm to 5 mm and/or between 10 mm to 50 mm. In some embodiments, a base of an injection device may include an adhesive skirt. In some embodiments, a skin contact area of an injector not on the base may include an adhesive skirt. For example, the adhesive skirt of skin contact area not on the base may extend beyond an area where the adhesive is attached to the injector between 0.1 mm to 1 mm and/or between 1 mm to 5 mm. In some embodiments, the adhesive skirt on the base may extend ranging from 10% to 50% and/or from 50% to 250% and/or from 250% to 1000% or more further than the length to which a skirt extends on another skin contact surface of the injector.

In some embodiments, skirt may include an edge region of the patch. Optionally, the skirt may not entirely surround the patch. For example, a section 2531 of the edge may be connected to the base. For example, a dorsal side of section 2531 may have adhesive for attachment to the frame 3026*b* of device 2501.

In some embodiments a ventral liner 2577 of the patch may be peeled of the patch form the an edge of the patch. For example, dorsal edge section 2531 may be connected to frame 3026*b* at a location where a ventral liner 2577 is peeled off a ventral side of patch 2520. For example, the connection of section 2531 to the frame 3026*b* may add stiffness to section 3026*b* making it easier to peel the liner. Alternatively or additionally, a ventral liner may be peeled from the center of the patch.

In some embodiments, an alignment jig may include an opening or slits. For example, jig 2540 includes slits 2579*a* and 2579*b*. For example a peeling tab of ventral liner 2577 may pass through slit 2579*b* for example as illustrated in FIGS. 25 and 26. Optionally a dorsal liner 2532 of a patch may include a peeling tab 2582. Optionally, peeling tab 2582 is configured to allow a single pull peeling of dorsal liner 2532. For example, tab 2582 is located near the joining of stationary portion 3130 and disengageable portion 3156. For example, as illustrated in FIG. 26, a peeling tab of liner 2577 may pass through slit 2579*b* an be adhered to the base of device 2501. For example, the peeling tab may include an adhesive for sticking to device 2501.

In some embodiments an alignment jig may include a locking feature. Optionally, a locking feature may hold a dosage control device to a patch. For example, jig 2540 includes an overhang 2542. Optionally a tab of device 2501 includes a tab (for example alignment feature 2527) which fits under overhang. Optionally, when device 2501 is positioned under overhang 2542 and/or pivoted onto jig 2540, a contact surface of frame 3026*b* and/or attachment portion 3124 is pushed into contact and/or attachment with device 2501. Optionally a portion of jig 2540 may be made of a soft material (for example Styrofoam and/or elastomer) that distributes pressure evenly along a contact surface. For example, protrusion 2543 may be made of a soft material. For example, a contact surface may have a hardness ranging on a shore 00 scale between 10 to 50 and/or on a shore A scale ranging between 5 to 25 and/or between 25 to 50 and/or between 50 to 100.

FIG. 26 is a cutaway side view of dosage control device 2501 and patch 2520 aligned together with jig 2540 in accordance with an embodiment of the current invention. In some embodiments, a ventral liner of a patch may be connected to an alignment device. For example, tabs of liner 2577 may be inserted through slots 2579*a* and/or 2579*b* and/or adhered to jig 2540. Optionally, when device 2501 is attached to a dorsal face of patch 2520 and then pulled away from jig 2540, liner 2577 remains attached to jig 2540 and/or is peeled off the ventral face of patch 2520. Optionally, patch 2520 and/or jig 2540 are supplied together. For example, jig 2540 may be part of the packaging of patch 2520 as it is supplied and/or sold to a user. Alternatively or additionally, patch 2520 may be supplied separately from jig 2540. Optionally, a user may attach a ventral liner to the jig. For example, before contacting dosage control device 2501 to patch 2520 and/or jig 2540, a user may attach liner 2577 to jig 2540. Optionally patch 2520 and/or jig 2540 may include a connector for making the attachment. For example, an adhesive may be supplied on tabs of liner 2577 and/or a surface of device 2501. For example, the user may insert tabs of liner 2577 through slits 2579*a*, 2579*b* and/or adhere the tabs to the base of jig 2540.

In some embodiments, a protrusion on an alignment device facilities connection between a patch and a dosage control device. For example, protrusion 2543 pushes attachment portion 3124 onto roller 2616. In some embodiments, a locking element locks dosage control device 2501 onto jig 2540. For example, an overhang 2580 may lock onto a tab, such as alignment feature 2527. For example, overhang 2580 may lock front portion 2666 of device 2501 onto jig 2540. Subsequently, the rear part 3065 of delivery device 2501 may be rotated to contact the rear portion of jig 2540. Optionally, an interference element may lock the rear portion 3065 onto the jig 2540.

In some embodiments a patch may be attached to a dosage control device while the patch is in an extended state. Optionally, the patch is moved to a stored and/or inactive position after attachment of the attachment portion of the patch to the actuator of the dosage control device. For example, a sensor and/or switch may register when dosage control device 2501 is fully placed on jig 2540 and/or in response, patch 2520 may be rolled onto roller 2616. Alternatively or additionally, a sensor and/or switch may register when dosage control device 2501 is taken away from jig 2540 after being placed thereon and/or in response, patch 2520 may be rolled onto roller 2616. Alternatively or additionally, patch 2520 may be rolled onto roller 2616 in response to a user action and/or an external device (for example a communication over a network). For example, jig 2540 may include a protrusion that activates a switch in device 2501 when device is positioned onto and/or moved off of jig. 2540.

Pealing a Liner

Figure 27:
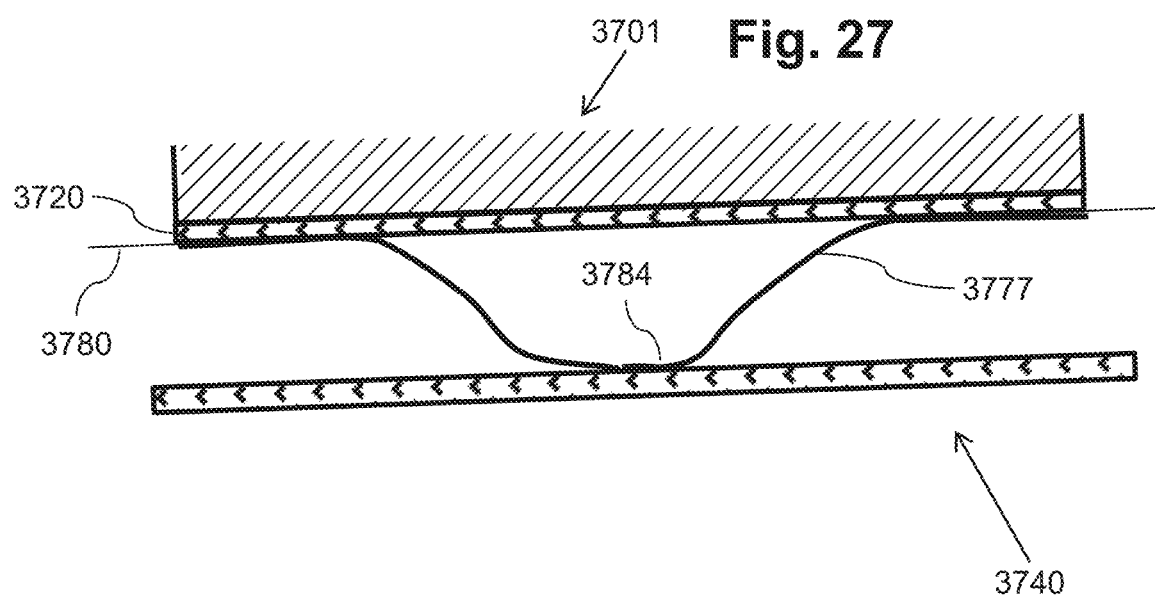
FIG. 27 is a schematic illustration of a dosage control device connected to a transdermal pharmaceutical patch being pulled away from a jig in accordance with an embodiment of the current invention.

FIG. 27 is a schematic illustration of a dosage control device 3701 connected to a transdermal pharmaceutical patch 3720 being pulled away from a jig 3740 in accordance with an embodiment of the current invention. In some embodiments, a ventral liner 3777 of patch 3720 is connected in a central location to Jig 3740. Optionally, when a central portion of liner 3777 is attached to jig 3740, a skirt 3780 on an edge of patch 3720 may remain free and/or mobile with respect to device 3701.

In some embodiments, a tab may be attached to an inner surface of a jig. For example, tab 3782 may be attached to an inner surface of jig 2740. Alternatively or additionally, a tab may be attached to an outer surface of a jig (for example liner 2577 of FIGS. 25 and 26 passes through a slit 2579*b* in jig 2540 and is attached to an outer surface thereof. In some embodiments, attachment may be using adhesive. Alternatively or additionally there may be another attachment method such as a pin and/or a hole and/or a quick connect etc.

In some embodiments, a tab 3784 of liner 3777 may be connected to jig 3740. For example, tab 3784 may be free (e.g. not adhered to patch 3720). Optionally, the length of the tab may be adjusted. For example, having a long tab may make it easier to start moving device 3701 away from jig 3740 and/or may increase the angle of peeling and/or make it easier to peel. For example, a tab may have a length ranging between 1 mm to 3 mm and/o between 3 mm to 10 mm and/or between 10 mm to 20 mm.

Biased Patch

Figure 28:
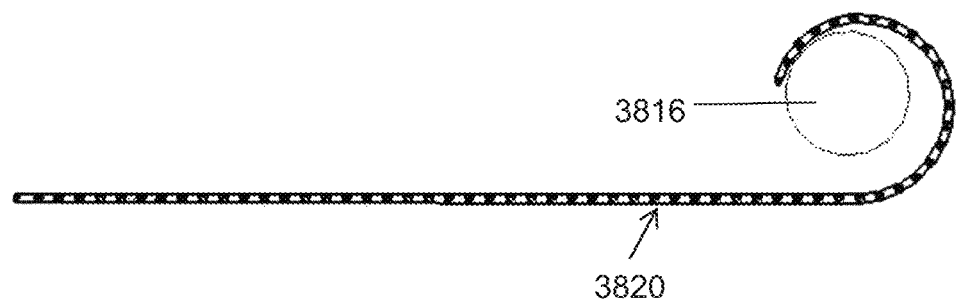
FIG. 28 is a schematic illustration of a patch that is biased away from an actuator in accordance with an embodiment of the current invention.

FIG. 28 is a schematic illustration of a patch 3820 that is biased away from an actuator 3816 in accordance with an embodiment of the current invention. For example, actuator 3816 may include a roller. Biasing patch 3820 away from the roller may cause patch 3820 to unroll and/or push itself onto and/or attach itself to the skin of a subject. For example, the patch 3820 may be elastically biased to a straighten out away from a rolled up state roller 3816. Optionally, biasing may be due to an elastic element. For example, patch 3820 may include a standard transdermal pharmaceutical patch and/or a backing biased to unroll the patch. For example, a ventral liner (for example liner 922 and/or an additional liner) may be biased to push the patch towards the skin of the subject.

In some embodiments, elasticity and/or stiffness of a patch may be balanced against malleability and/or suppleness. For example, elasticity and/or stiffness may be increased to cause a patch to unroll and/or push itself from a roller onto the skin of a subject. Alternatively or additionally, malleability and/or suppleness may be increased to facilitate the patch remaining on the skin over time, for example as a subject moves. For example, a patch may be supple enough that a bending force over the patch to reach a radius of curvature typical of skin will not reach a force great enough to peel a part of the patch form the skin. For example, a stiffness biasing of said patch is optionally small enough that bending said patch to a radius of curvature of 10 mm from its unstressed shape requires a force differential over the patch of less than 2 Newton and/or less than 1 Newton and/or less than 0.5 Newton and/or less than 0.1 Newton. Optionally, the elasticity of the patch may be high enough that when the patch is wound around a roller of device 2501 to a radius of 5 mm it spontaneously unwinds with a force at the edge of the roll of at least 0.01 Newton and/or at least 0.1 Newton and/or at least 0.5 Newton and/or at least 1 Newton and/or at least 2 Newton.

In some embodiments a patch may have more than one stable state. For example a patch may have a stable state wound around a roller. Optionally, a change (for example in position or temperature) may cause the patch to bias away from a rolled up state.

In some embodiments, biasing away from a roller may result from the rate of rotation of the roller. For example, a roller may unroll a patch at a rate greater than the linear movement of the roller. Optionally, the patch is may be made of stiff material and/or includes a stiff backing that inhibits folding of the patch. For example, the result of the excess patch that is being unrolled may be that the patch bulges outward from the device and/or is pushed against the skin of a subject. For example, the rate of patch unrolling may be between 100% to 101% the rate of movement of the roller and/or between 101% to 103% and/or between 103% to 106% and/or between 106% to 112% and/or between 112% to 125% and/or between 125% to 150%. For example, an extra length of patch may be released that is longer than the space on the skin where it is meant to be attached and/or longer than the linear movement of the applicator. For example, the extra length may range between 0.1 to 1 mm and/or between 1 to 2 mm and/or between 2 to 4 mm and/or between 4 to 8 mm and/or between 8 to 15 and/or between 15 to 30 mm.

FIGS. 29A to 31B illustrate exemplary optional unstressed curvatures and shapes for a medicine patch in accordance with embodiments of the current invention.

Figure 29A:
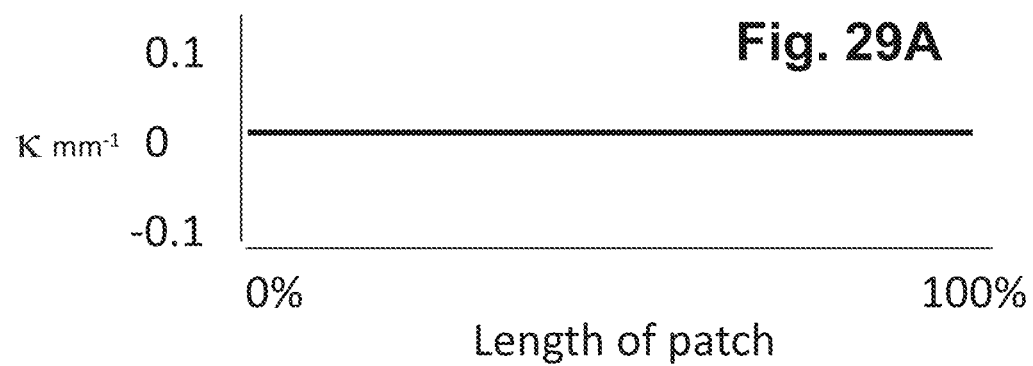
Figure 29B:

In some embodiments an elastic patch 2920 will have a uniform unstressed curvature (the curvature being one over the radius of curvature) of zero (e.g. infinite radius of curvature) (for example as illustrated in FIG. 29A) and an unstressed flat form (for example as illustrated in FIG. 29B). Optionally, the patch 2920 is stiff enough to push itself against the skin of a subject as it unrolls and/or supple enough to remain on the skin of a subject even as the subject's skin deforms for example as he moves.

In some embodiments an elastic patch 4020 will have a uniform unstressed curvature of less than zero (for example ranging between 0 to $-0.01$ mm$^{-1}$ and/or between $-0.01$ to $-0.05$ mm$^{-1}$ and/or between $-0.05$ to $-0.1$ mm$^{-1}$ and/or between $-0.1$ to $-0.5$ mm$^{-1}$ (for example as illustrated in FIG. 30A) and an unstressed concave downward form (for example as illustrated in FIG. 30B). Optionally, the patch 4020 is stiff enough to push itself against the skin of a subject as it unrolls and/or supple enough to remain stuck to the skin of a subject for example in the central region of the patch 4020 even as the subject's skin deforms for example as he moves.

In some embodiments an elastic patch 3120 will have a uniform unstressed curvature of less than zero (for example ranging between 0 to $-0.01$ mm$^{-1}$ and/or between $-0.01$ to $-0.05$ mm$^{-1}$ and/or between $-0.05$ to $-0.1$ mm$^{-1}$ and/or between $-0.1$ to $-0.5$ mm$^{-1}$ near the edges (for example on a skirt for example to inhibit pealing of the edges from the subject) and/or a positive curvature in a central region (for example in an active zone for example to keep good contact and/or facilitate drug delivery), (for example as illustrated in FIG. 31A). Optionally an unstressed form would be concave downward on the sides and concave upward in the central region (for example as illustrated in FIG. 31B).

It is expected that during the life of a patent maturing from this application many relevant technologies will be developed and the scope of the terms for example patch is intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed:

1. A dosage control system for transdermal administration of a drug to a subject comprising:
   a. a housing including a skin attachment surface on a ventral side thereof;
   b. an opening in said ventral side of said housing for engaging a transdermal patch there through;
   c. a roller passing along said opening,
   and a guide directing said passing of said roller and changing a rate of rotation of said roller per linear movement on said guide, wherein said roller includes a toothed gear rotated by a toothed track of said guide and wherein a distance between teeth of said track varies to vary said rate of rotation; optionally, wherein said distance between teeth of said track varies non-uniformly.

* * * * *